US012753207B2

(12) United States Patent
Beau et al.

(10) Patent No.: US 12,753,207 B2
(45) Date of Patent: Oct. 6, 2026

(54) ***PAENIBACILLUS* STRAIN, ANTIFUNGAL COMPOUNDS, AND METHODS FOR THEIR USE**

(71) Applicant: Bayer CropScience LLC, St. Louis, MO (US)

(72) Inventors: Jeremy Beau, Woodland, CA (US); Daniel M. Joo, Raleigh, NC (US); Patrick Schwientek, Davis, CA (US); Colleen S. Taylor, Folsom, CA (US); Bjorn A. Traag, Walnut Creek, CA (US)

(73) Assignee: Bayer CropScience LLC, St. Louis, MO (US)

( * ) Notice: Subject to any disclaimer, the term of this patent is extended or adjusted under 35 U.S.C. 154(b) by 728 days.

(21) Appl. No.: 18/175,114

(22) Filed: Feb. 27, 2023

(65) Prior Publication Data

US 2023/0234988 A1 Jul. 27, 2023

Related U.S. Application Data

(63) Continuation of application No. 16/669,783, filed on Oct. 31, 2019, now Pat. No. 11,623,944, which is a continuation of application No. 16/190,556, filed on Nov. 14, 2018, now Pat. No. 10,499,656, which is a continuation of application No. 15/874,577, filed on Jan. 18, 2018, now Pat. No. 10,159,257, which is a continuation of application No. 15/078,670, filed on Mar. 23, 2016, now Pat. No. 9,883,676.

(60) Provisional application No. 62/232,205, filed on Sep. 24, 2015, provisional application No. 62/138,765, filed on Mar. 26, 2015.

(51) Int. Cl.

| | |
|---|---|
| ***C07K 11/02*** | (2006.01) |
| ***A01N 63/25*** | (2020.01) |
| ***C07K 14/195*** | (2006.01) |
| ***C12N 1/205*** | (2026.01) |
| ***C12N 9/00*** | (2006.01) |
| ***C12N 9/90*** | (2006.01) |
| *C12R 1/01* | (2006.01) |

(52) U.S. Cl.

CPC .............. *C07K 11/02* (2013.01); *A01N 63/25* (2020.01); *C07K 14/195* (2013.01); *C12N 1/205* (2021.05); *C12N 9/90* (2013.01); *C12N 9/93* (2013.01); *C12R 2001/01* (2021.05)

(58) Field of Classification Search

CPC . C12N 9/93; C12N 1/205; C12N 9/90; C07K 14/195

See application file for complete search history.

(56) References Cited

FOREIGN PATENT DOCUMENTS

WO WO-2007086645 A1 * 8/2007 .............. C12P 21/02

OTHER PUBLICATIONS

Kaneda, M. & Kajimura, Y., "New Antifungal Antibiotics, Bacillopeptins and Fusaricidins" Yakugaku Zasshi vol. 122, No. 9. (Year:2002).
Bernstein, J. "Polymorphism of Molecular Crystals." Moscow, Nauka, 2007, chapter 7.3.2. Bioavailability, pp. 324-330.
Braun, D. et al., "Solid state characterization of four solvates of R-cinacalcet hydrochloride" CrystEngComm, 2008, v.10, No. 11, 1617.
Nguyen, L.A. et al., "Chiral Drugs: An Overview" International journal of biomedical science: IJBS, 2006, v.2,2, p. 85-100.

* cited by examiner

*Primary Examiner* — Tekchand Saidha
(74) *Attorney, Agent, or Firm* — Michelle L. Samonek

(57) ABSTRACT

The present invention relates to a composition comprising a biologically pure culture of a fungicidal *Paenibacillus* sp. strain comprising a variant fusaricidin synthetase lacking a functional adenylation domain in the third module. The present invention also provides a composition comprising a biologically pure culture of a fungicidal *Paenibacillus* sp. strain or a cell-free extract thereof comprising at least one Paeniserine and at least one Paeniprolixin. Also provided are isolated compounds and methods of treating a plant to control a plant disease with the disclosed compositions and compounds.

2 Claims, 41 Drawing Sheets

Specification includes a Sequence Listing.

FIG. 2

| Sample | | ALTE AL | BOTR CI | FUSA CU | LEPTN O | SEPPT R | PHYT CR | PHYTI N | PYTH UL | PYRIO R | RHIZS O | USTI AV | UROMA P |
|---|---|---|---|---|---|---|---|---|---|---|---|---|---|
| Strain X | $ED_{50}$ | >100 | >100 | >100 | >100 | >100 | >100 | >100 | >100 | >100 | >100 | >100 | >100 |
| Fraction 1 | $ED_{80}$ | >100 | >100 | >100 | >100 | >100 | >100 | >100 | >100 | >100 | >100 | >100 | >100 |
| Strain X | $ED_{50}$ | >100 | >100 | >100 | >100 | >100 | >100 | >100 | >100 | 42 | >100 | >100 | >100 |
| Fraction 2 | $ED_{80}$ | >100 | >100 | >100 | >100 | >100 | >100 | >100 | >100 | 54 | >100 | >100 | >100 |
| Strain X | $ED_{50}$ | 15 | 32 | 44 | 22 | 4.7 | >100 | 1.1 | 43 | 36 | 7.8 | 34 | >100 |
| Fraction 3 | $ED_{80}$ | 43 | 98 | >100 | >100 | 24 | >100 | 4.8 | >100 | >100 | 20 | >100 | >100 |
| NRRL B-50972 | $ED_{50}$ | 1.2 | 1.2 | 3.3 | 1.6 | 1.4 | 1.6 | 0.1 | 1.3 | 3.5 | 0.7 | 2.5 | 0.9 |
| Fraction 1 | $ED_{80}$ | 2.4 | 1.7 | 4.2 | 6.4 | 1.6 | 2.1 | 0.2 | 1.6 | 7 | 1.5 | 2.8 | 1.2 |

LiF04a "fusaricidin A"
cyclic compound

LiF04c
acyclic compound

FIG. 4C

| Compound | Cyclic or Acyclic | Molecular Formula | AA (2) | AA (3) | AA (5) | m/z | RT (min) |
|---|---|---|---|---|---|---|---|
| **"C" - LiF03a** | Cyclic | $C_{45}H_{74}N_{10}O_{12}$ | Val | Tyr | Asn | Not Detected | |
| **"D" - LiF03b** | Cyclic | $C_{46}H_{76}N_{10}O_{12}$ | Val | Tyr | Gln | Not Detected | |
| **LiF03c** | Acyclic | $C_{45}H_{76}N_{10}O_{13}$ | Val | Tyr | Asn | Not Detected | |
| **LiF03d** | Acyclic | $C_{46}H_{78}N_{10}O_{13}$ | Val | Tyr | Gln | Not Detected | |
| **"A" - LiF04a** | Cyclic | $C_{41}H_{74}N_{10}O_{11}$ | Val | Val | Asn | 883.5 | 13.64 |
| **"B" - LiF04b** | Cyclic | $C_{42}H_{76}N_{10}O_{11}$ | Val | Val | Gln | 897.6 | 13.57 |
| **LiF04c** | Acyclic | $C_{41}H_{76}N_{10}O_{12}$ | Val | Val | Asn | 901.6 | 9.33 |
| **LiF04d** | Acyclic | $C_{42}H_{78}N_{10}O_{12}$ | Val | Val | Gln | 915.6 | 9.35 |
| **LiF05a** | Cyclic | $C_{42}H_{76}N_{10}O_{11}$ | Val | Ile | Asn | 897.6 | 16.99 |
| **LiF05b** | Cyclic | $C_{43}H_{78}N_{10}O_{11}$ | Val | Ile | Gln | 911.6 | 16.90 |
| **LiF05c** | Acyclic | $C_{42}H_{78}N_{10}O_{12}$ | Val | Ile | Asn | 915.6 | 12.12 |
| **LiF05d** | Acyclic | $C_{43}H_{80}N_{10}O_{12}$ | Val | Ile | Gln | 929.6 | 12.11 |
| **LiF06a** | Cyclic | $C_{42}H_{76}N_{10}O_{11}$ | Ile | Val | Asn | 897.6 | 17.30 |
| **LiF06b** | Cyclic | $C_{43}H_{78}N_{10}O_{11}$ | Ile | Val | Gln | 911.6 | 17.35 |
| **LiF06c** | Acyclic | $C_{42}H_{78}N_{10}O_{12}$ | Ile | Val | Asn | 915.6 | 12.12 |
| **LiF06d** | Acyclic | $C_{43}H_{80}N_{10}O_{12}$ | Ile | Val | Gln | 929.6 | 12.11 |
| **LiF07a** | Cyclic | $C_{45}H_{74}N_{10}O_{11}$ | Val | Phe | Asn | Not Detected | |
| **LiF07b** | Cyclic | $C_{46}H_{76}N_{10}O_{11}$ | Val | Phe | Gln | Not Detected | |
| **LiF07c** | Acyclic | $C_{45}H_{76}N_{10}O_{12}$ | Val | Phe | Asn | Not Detected | |
| **LiF07d** | Acyclic | $C_{46}H_{78}N_{10}O_{12}$ | Val | Phe | Gln | Not Detected | |
| **LiF08a** | Cyclic | $C_{43}H_{78}N_{10}O_{11}$ | Ile | Ile | Asn | 911.6 | 19.99 |
| **LiF08b** | Cyclic | $C_{44}H_{80}N_{10}O_{11}$ | Ile | Ile | Gln | 925.6 | 20.02 |
| **LiF08c** | Acyclic | $C_{43}H_{80}N_{10}O_{12}$ | Ile | Ile | Asn | 929.6 | 12.11 |
| **LiF08d** | Acyclic | $C_{44}H_{82}N_{10}O_{12}$ | Ile | Ile | Gln | 943.6 | 12.11 |

FIG. 5C

| Compound | Cyclic or Acyclic | Molecular Formula | AA (1) | AA (4) | AA (5) | m/z | RT (min) |
|---|---|---|---|---|---|---|---|
| **Paeniserine A1** | Cyclic | $C_{40}H_{72}N_{10}O_{11}$ | Ser | Thr | Asn | 869.5 | 11.26 |
| **Paeniserine A2** | Cyclic | $C_{41}H_{74}N_{10}O_{11}$ | Ser | Thr | Gln | 883.5 | 11.12 |
| **Paeniserine A3** | Acyclic | $C_{40}H_{74}N_{10}O_{12}$ | Ser | Thr | Asn | 887.5 | 8.38 |
| **Paeniserine A4** | Acyclic | $C_{41}H_{76}N_{10}O_{12}$ | Ser | Thr | Gln | 901.6 | 8.41 |
| **Paeniserine B1** | Cyclic | $C_{40}H_{72}N_{10}O_{11}$ | Thr | Ser | Asn | 869.5 | 11.67 |
| **Paeniserine B2** | Cyclic | $C_{41}H_{74}N_{10}O_{11}$ | Thr | Ser | Gln | 883.5 | 11.16 |
| **Paeniserine B3** | Acyclic | $C_{40}H_{74}N_{10}O_{12}$ | Thr | Ser | Asn | 887.5 | 8.79 |
| **Paeniserine B4** | Acyclic | $C_{41}H_{76}N_{10}O_{12}$ | Thr | Ser | Gln | 901.6 | 8.67 |
| **Paeniserine C1** | Cyclic | $C_{39}H_{70}N_{10}O_{11}$ | Ser | Ser | Asn | 855.5 | 8.81 |
| **Paeniserine C2** | Cyclic | $C_{40}H_{72}N_{10}O_{11}$ | Ser | Ser | Gln | 869.5 | 8.62 |
| **Paeniserine C3** | Acyclic | $C_{39}H_{72}N_{10}O_{12}$ | Ser | Ser | Asn | 873.5 | 7.22 |
| **Paeniserine C4** | Acyclic | $C_{40}H_{74}N_{10}O_{12}$ | Ser | Ser | Gln | Not Detected | |

FIG. 8C

| Compound | Molecular Formula | AA (2) | AA (3) | AA (5) | Tail | m/z | RT (min) |
|---|---|---|---|---|---|---|---|
| **Paeniprolixin A1** | $C_{44}H_{80}N_{10}O_{11}$ | Val | Ile | Asn | GHPD+2$CH_2$ | 925.6 | 20.87 |
| **Paeniprolixin A2** | $C_{45}H_{82}N_{10}O_{11}$ | Val | Ile | Gln | GHPD+2$CH_2$ | 939.6 | 23.63 |
| **Paeniprolixin B1** | $C_{44}H_{80}N_{10}O_{11}$ | Ile | Val | Asn | GHPD+2$CH_2$ | 925.6 | 21.88 |
| **Paeniprolixin B2** | $C_{45}H_{82}N_{10}O_{11}$ | Ile | Val | Gln | GHPD+2$CH_2$ | 939.6 | 23.92 |
| **Paeniprolixin C1** | $C_{45}H_{82}N_{10}O_{11}$ | Ile | Ile | Asn | GHPD+2$CH_2$ | 939.6 | 24.56 |
| **Paeniprolixin C2** | $C_{45}H_{82}N_{10}O_{11}$ | Ile | Ile | Gln | GHPD+2$CH_2$ | Not Detected | |
| **Paeniprolixin D1** | $C_{45}H_{82}N_{10}O_{11}$ | Val | Val | Asn | GHPD+4$CH_2$ | 939.6 | 27.22 |
| **Paeniprolixin D2** | $C_{45}H_{82}N_{10}O_{11}$ | Val | Val | Gln | GHPD+4$CH_2$ | Not Detected | |
| **Paeniprolixin E1** | $C_{46}H_{84}N_{10}O_{11}$ | Val | Ile | Asn | GHPD+4$CH_2$ | 953.6 | 25.54 |
| **Paeniprolixin E2** | $C_{47}H_{86}N_{10}O_{11}$ | Val | Ile | Gln | GHPD+4$CH_2$ | 967.6 | 28.60 |
| **Paeniprolixin F1** | $C_{46}H_{84}N_{10}O_{11}$ | Ile | Val | Asn | GHPD+4$CH_2$ | 953.6 | 26.17 |
| **Paeniprolixin F2** | $C_{47}H_{86}N_{10}O_{11}$ | Ile | Val | Gln | GHPD+4$CH_2$ | 967.6 | 30.26 |
| **Paeniprolixin G1** | $C_{47}H_{86}N_{10}O_{11}$ | Ile | Ile | Asn | GHPD+4$CH_2$ | 966.6 | 31.02 |
| **Paeniprolixin G2** | $C_{48}H_{88}N_{10}O_{11}$ | Ile | Ile | Gln | GHPD+4$CH_2$ | Not Detected | |

| Sample Code | Name | COLLLA |
|---|---|---|
| **AB** | Fusaricidin A and B | 10 mm |
| **868** | Paeniserines A1 and B1 | 9 mm |
| **938** | Paeniprolixin A2 and B2 | 7 mm |
| **868/938** | Combination of 868 and 938 | 12 mm |

FIG. 12A
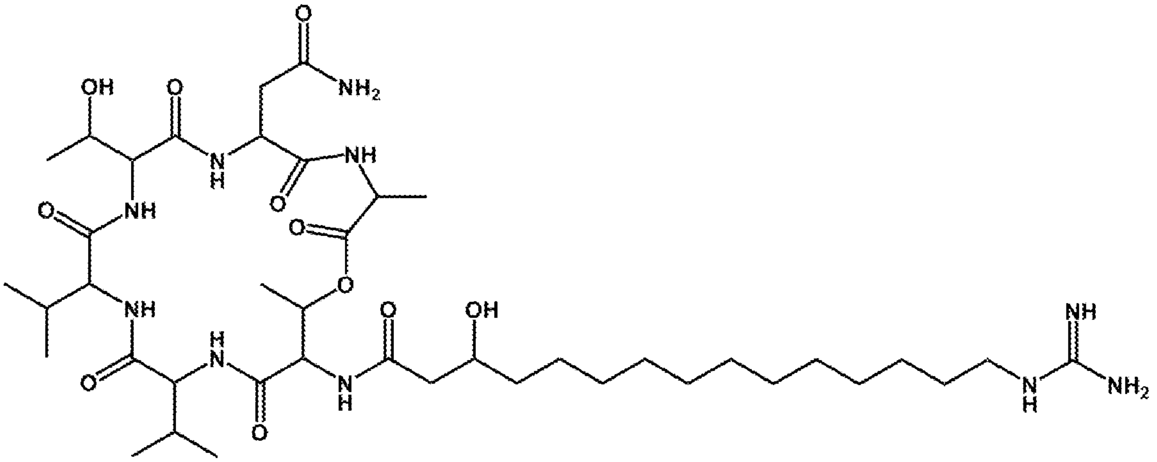
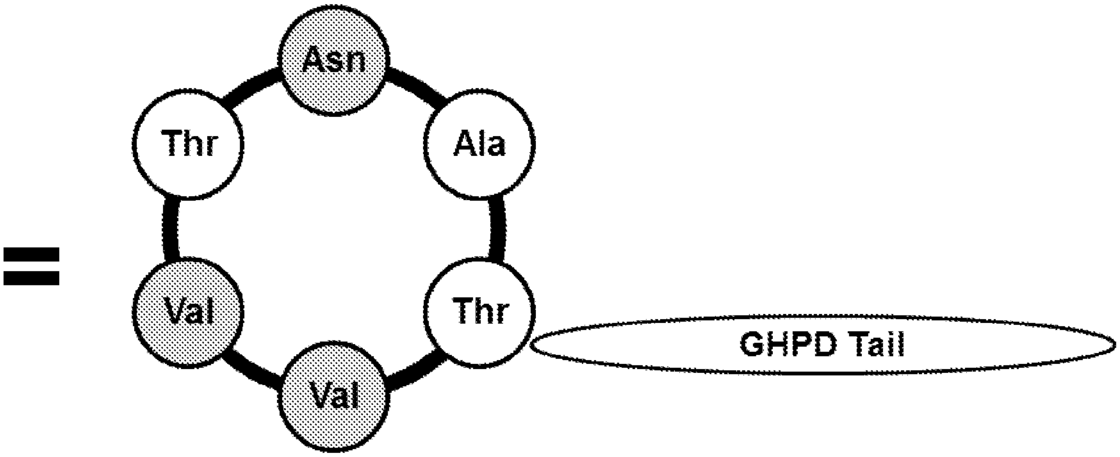

FIG. 12E
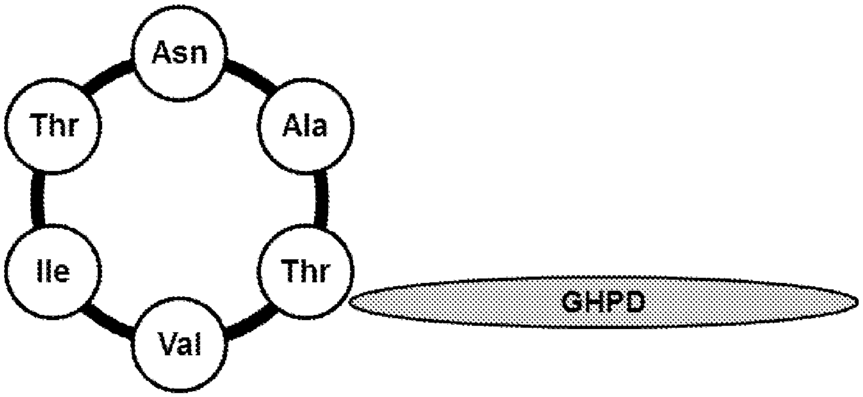
LiF05a
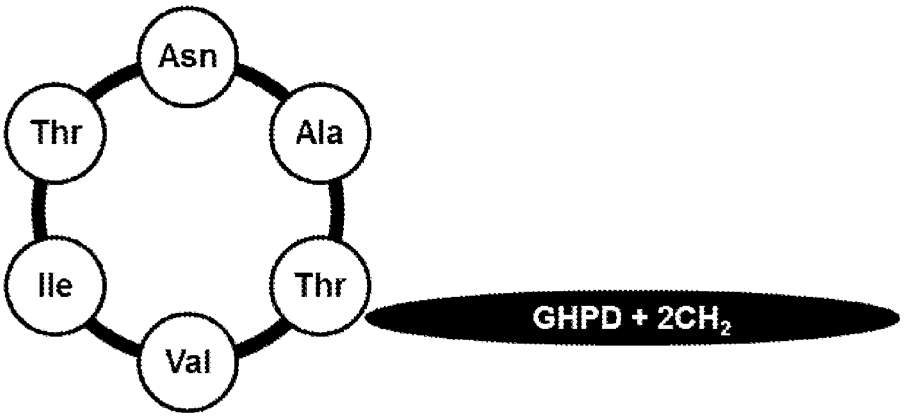
Paeniprolixin A2
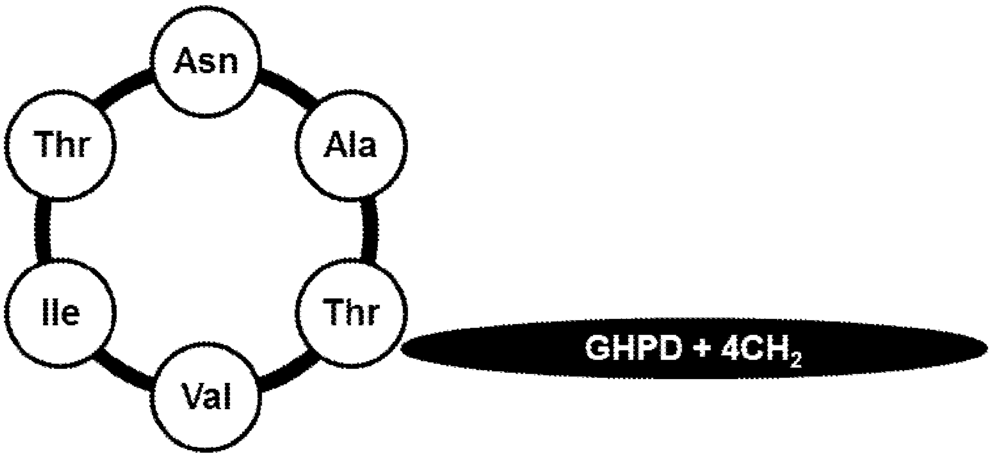
Paeniprolixin E1

FIG. 13

```
Paenibacillus_peoriae_A            NALVYDPVTIEQIKGHLVHLMEQIVENPAISVDALELVTPQEREQILNVW 2999
Paenibacillus_polymyxa_A           NALVYDQVTIGQIKGHLVHLMEQIVENPAISVDALELVTPQEREQILNVW 2999
Paenibacillus_polymyxa_PKB1        NALVYDPVTIEQIKGHLVHLMEQIVENPAISVDALELVTPQEREQILNVW 2999
Paenibacillus_polymyxa_E681        NALVYDPVTIGQIKGHLVHLMEQIVENPAISVDALELITPQEREQILNVW 2999
Paenibacillus_polymyxa_B           NALVYDQVTIEQIKEHLVHLMEQIIENPATSVDALELVTPQEREQILNVW 2999
Paenibacillus_polymyxa_SQR         NALVYDPATIEQIKGHLFHLMEQIVENPAISVDALELVTPQEREQILSVW 3000
Paenibacillus_polymyxa_C           NALVYDPSTIEQIKGHLFHLMEQIVENPAISVDALELVTPQEREQILNVW 3000
Paenibacillus_polymyxa_M1          NALVYDPATIEQIKGHLFHLMEQIVENPAISVDALELVTPQEREQILNVW 3000
Paenibacillus_polymyxa_SC2         NALVYDPATIEQIKGHLFHLMEQIVENPAISVDALELVTPQEREQILNVW 3000
Paenibacillus_sp_NRRL B-50972      NTLVYDSSNIERIRGHLVHLMEQIVKNPGISVDALELVTPQERDHILNIW 2999
Paenibacillus_sp_A                 NALVYDQVTIEQIKGHLVHLMEQIVENPAISVDALELVTPQERELILDVW 2999
                                   *:****  .* :*: **.******::**. *******:*****: **.:*

Paenibacillus_peoriae_A            GNTKGIYEHCNTFHGLLEEQAGRTPDATAIWFEDESLTYAELNAKANGLA 3049
Paenibacillus_polymyxa_A           GNMKGIYEHCNTFHGLLEEQAGRTPDATAIWFEDESLTYAELNAKANGLA 3049
Paenibacillus_polymyxa_PKB1        GNTKGIYEHCNTFHGLLEEQAGRTPDATAIWFEDESLTYAELNAKANGLA 3049
Paenibacillus_polymyxa_E681        GNTKAIYEHYNTFHGLLEEQAGRTPDAAAIWFEDESLTYAELNAKANGLA 3049
Paenibacillus_polymyxa_B           GNTNVCYEHNSTFHGLLEEQAGRTPDATALLFGDEMLTYAELNAKANGLA 3049
Paenibacillus_polymyxa_SQR         GETEASSKHRTTFHGLLEEQAARTPDATAILFENEMLTYAELNAKANGLA 3050
Paenibacillus_polymyxa_C           GETEASSKHRTTFHGLLEEQAARTPDATAILFENEMLTYAELNAKANGLA 3050
Paenibacillus_polymyxa_M1          GDTGASSKHRTTFHGLLEEQAGRTPDATAIVFENEVLTYAELNAKANGLA 3050
Paenibacillus_polymyxa_SC2         GDTGASSKHRTTFHGLLEEQAGRTPDATAIVFENEVLTYAELNAKANGLA 3050
Paenibacillus_sp_NRRL B-50972      KDIAVPYEH-----------------------------YAELHAQAQ--- 3017
Paenibacillus_sp_A                 GNTKVSYEHCNTFHGLLEEQAGRTPEATAIVFEDEMLTYAELNAKANGLA 3049
                                    :     :*                             ****:*:*:
```

FIG. 13 (continued)

```
Paenibacillus_peoriae_A           RRLRTQGIKTGDLVGLIAERSLEMIVGIYGIMKAGGAYVPIDPEYPKERI 3099
Paenibacillus_polymyxa_A          RRLRTQGIKTGDLVGLIAERSLEMIVGIYGIMKAGGAYVPIDPEYPKERI 3099
Paenibacillus_polymyxa_PKB1       RRLRTQGIKTGDLVGLIAERSLEMIVGIYGIMKAGGAYVPIDPEYPKERI 3099
Paenibacillus_polymyxa_E681       RRLRTQGIKTGDLVGLIAERSLEMIVGIYGIMKAGGAYVPIDPEYPQERI 3099
Paenibacillus_polymyxa_B          RRLRTQGIKTGDLVGLIAERSLEMIVGIYGIMKAGGAYVPIDPEYPKERI 3099
Paenibacillus_polymyxa_SQR        RRLRAEGIKTGDLVGLLVERSTDMIVGMYGIMKAGGAYVPIDPEYPKERI 3100
Paenibacillus_polymyxa_C          RRLRAEGIKTGDLVGLLVERSTDMIVGMYGIMKAGGAYVPMDPEYPKERI 3100
Paenibacillus_polymyxa_M1         RRLRAEGIKTGDLVGLIVERSTDMIVGMYGIMKAGGAYVPIDPEYPKERI 3100
Paenibacillus_polymyxa_SC2        RRLRAEGIKTGDLVGLIVERSTDMIVGMYGIMKAGGAYVPIDPEYPKERI 3100
Paenibacillus_sp_NRRL B-50972     --------------------------------------------------
Paenibacillus_sp_A                RKLRNQGIQTGDLVGLIADRSSEMIVGIYGIMKAGGAYVPIDPEYPKERI 3099

Paenibacillus_peoriae_A           SYMLEDSGAKLILTQAHFLEHLGWTENVLLLDESSTYDADTSNLEDTAGP 3149
Paenibacillus_polymyxa_A          SYMLEDSGAKLILTQAHLLEHLGWTENVLLLDESSTYDADTSNLEDTAGP 3149
Paenibacillus_polymyxa_PKB1       SYMLEDSGAKLILTQAHLLEHLGWTENVLLLDESSTYDADTSNLEDTAGP 3149
Paenibacillus_polymyxa_E681       SYMLEDSGAKLILTQAHLLEHLGWTENVLLLDESSTYDADTSNLEDTAGP 3149
Paenibacillus_polymyxa_B          SYMLEDSGAKLILTQAHLLEHLGWTESVLLLDESSTYDADTSKLEDTAGP 3149
Paenibacillus_polymyxa_SQR        NYMLEDSGTKMILTQAHLLEHIGWMGNVLLLEEPSTYDADESNLKDTADS 3150
Paenibacillus_polymyxa_C          NYMLEDSGTKMILAQAHLLEHIDWMGNVLLLEEPSTYDADESNLKDTANS 3150
Paenibacillus_polymyxa_M1         NYMLEDSGTKMILAQAHLLEHRGWTGNVLLLDEPSTYDADTSNLKDTADP 3150
Paenibacillus_polymyxa_SC2        NYMLEDSGTKMILAQAHLLEHRGWTGNVLLLDEPSTYDADTSNLKDTADP 3150
Paenibacillus_sp_NRRL B-50972     --------------------------------------------------
Paenibacillus_sp_A                SYMLEDSGAKLVLTQARLLEHLGWTENVLLLDEPSTYDADTSNLKDTVGP 3149
```

FIG. 13 (continued)

```
Paenibacillus_peoriae_A          DDLAYVIYTSGTTGQPKGVLVEHRGLPNLSDVYGAHFEVTPQDRIVQFAS 3199
Paenibacillus_polymyxa_A         DDLAYVIYTSGTTGQPKGVLVEHRGLPNLSNVYGAHFEVTPQDRIVQFAS 3199
Paenibacillus_polymyxa_PKB1      DDLAYVIYTSGTTGQPKGVLVEHRGLPNLSDVYGTHFEVTPQDRIVQFAS 3199
Paenibacillus_polymyxa_E681      DDLAYVIYTSGTTGQPKGVLVEHRGLPNLSDVYGAHFEVTPQDRIVQFAS 3199
Paenibacillus_polymyxa_B         DDLAYVIYTSGTTGQPKGVLVEHRGLPNLSDVYGAHFEVTPQDRIVQFAS 3199
Paenibacillus_polymyxa_SQR       DDLAYVIYTSGTTGQPKGVLVEHRGLRNLSDVYRGLFEVTPQDRIVQFAS 3200
Paenibacillus_polymyxa_C         DDLAYVIYTSGTTGQPKGVLVEHRGLRNLSDVYRGLFEVTPQDRIVQFAS 3200
Paenibacillus_polymyxa_M1        DDLAYVIYTSGTTGRPKGVLVEHRGLQNLSDVYRGLFEVTPQDRIVQFAS 3200
Paenibacillus_polymyxa_SC2       DDLAYVIYTSGTTGRPKGVLVEHRGLQNLSDVYRGLFEVTPQDRIVQFAS 3200
Paenibacillus_sp_NRRL B-50972    --------------------------------------------------
Paenibacillus_sp_A               DNLAYVIYTSGTTGQPKGVLVEHRGLQNLSDVYGTYFEVTPQDRIVQFAS 3199

Paenibacillus_peoriae_A          LSFDASVSEILTALSHGGVLCIPSTEDILDHALFEQFMNDKGVTVATLPP 3249
Paenibacillus_polymyxa_A         LSFDASVSEILTALSHGGVLCIPSTEDILDHALFEQFMNDKGITVATLPP 3249
Paenibacillus_polymyxa_PKB1      LSFDASVSEILTALSHGGVLCIPSTQDILDHALFEQFMNDKGITVATLPP 3249
Paenibacillus_polymyxa_E681      LSFDASVSEILTALSHGGVLCIPSAQDILDHALFEQFMNDKGITVATLPP 3249
Paenibacillus_polymyxa_B         LSFDASVSEILTALSHGGVLCIPSTQDILDHVLFEQFMNDKGITVATLPP 3249
Paenibacillus_polymyxa_SQR       LSFDASVSEIITALSHGATLCIPSTQDILDHALFEQFMNSKAITIATLPP 3250
Paenibacillus_polymyxa_C         LSFDASVSEIITALSHGATLCIPSTQDILDHALFEQFMNSKAITIATLPP 3250
Paenibacillus_polymyxa_M1        LSFDASVSEILTTLSHGATLCIPSTQEILDHALFEQFMNDKGITVATLPP 3250
Paenibacillus_polymyxa_SC2       LSFDASVSEILTTLSHGATLCIPSTQEILDHALFEQFMNDKGITVATLPP 3250
Paenibacillus_sp_NRRL B-50972    --------------------------------------------------
Paenibacillus_sp_A               LSFDASVSEVLTALSHGAALCIPSTQDILDYALFEQFINDKGITIATLPP 3249
```

FIG. 13 (continued)

```
Paenibacillus_peoriae_A          AYAIHLDPERLPTLRCLLTAGSAASVELIEEWRKHVRYSNGYGPTEDSVC 3299
Paenibacillus_polymyxa_A         AYAIHLDPERLPTLRCLLTAGSAASVELIEEWRKHVRYSNGYGPTEDSVC 3299
Paenibacillus_polymyxa_PKB1      AYAIHLDPERLPTLRCLLTAGSAASVELIEEWRKHVRYSNGYGPTEDSVC 3299
Paenibacillus_polymyxa_E681      AYAIHLDPERLPTLRCLLTAGSTASIELIEEWRKHVRYSNGYGPTEDSVC 3299
Paenibacillus_polymyxa_B         AYAIHLDPERLPTLRCLLTAGSAASVELIEEWRKHVRYSNGYGPTEDSVC 3299
Paenibacillus_polymyxa_SQR       AYIIHLEPERLPALRCLLTAGSATSVELIEKWRKHVQYFNGYGPTEDSVC 3300
Paenibacillus_polymyxa_C         AYIIHLEPERLPALRCLLTAGSATSVELIEKWRKHVQYFNGYGPTEDSVC 3300
Paenibacillus_polymyxa_M1        AYAIHLEPERLPTLRCLLTAGSATSVELIEKWRKHVQYFNAYGPTEDSVC 3300
Paenibacillus_polymyxa_SC2       AYAIHLEPERLPTLRCLLTAGSATSVELIEKWRKHVQYFNAYGPTEDSVC 3300
Paenibacillus_sp_NRRL B-50972    --------------------------------------------------
Paenibacillus_sp_A               AYAIHLEPERLPALRCLLTAGSAASVELIEKWRKHVRYSNGYGPTEDSIC 3299

Paenibacillus_peoriae_A          TTIWSVPDSEEATDIVSIGRPIANHSVYILDDHFRLQPVGVAGELCISSI 3349
Paenibacillus_polymyxa_A         TTIWSVPDSEEATDIVSIGRPIANHSVYILDDHFRLQPVGVAGELCISSI 3349
Paenibacillus_polymyxa_PKB1      TTIWSVPDSEEATDIVSIGRPIANHSVYILDDHFRLQPVGVAGELCISSI 3349
Paenibacillus_polymyxa_E681      TTIWSVPDSEEATNIVSIGRPIANHSVYILDDHFRLQPVGVAGELCISSI 3349
Paenibacillus_polymyxa_B         TTIWSVPDSEGATDIVSIGRPIANHSVYILDDHFRLQPVGVAGELCISGI 3349
Paenibacillus_polymyxa_SQR       TTMWTVPDSEETMERVSIGQPIANHRVYILDDHFRVLPVGVAGELCISGI 3350
Paenibacillus_polymyxa_C         TTMWTVPDSEETMERVSIGQPIANHRVYILDDHFRVLPVGVAGELCISGI 3350
Paenibacillus_polymyxa_M1        TTIWNAQNSEETVGIVSIGQPIANHRVYILDEHFRLLPVGVAGELCISGI 3350
Paenibacillus_polymyxa_SC2       TTIWNAQNSEETVGIVSIGQPIANHRVYILDEHFRLLPVGVAGELCISGI 3350
Paenibacillus_sp_NRRL B-50972    ------------------TAPIGQPNVYIVDDHFRLLPVGVAGELCIAGV 3049
Paenibacillus_sp_A               TTIWSVPDSEETLETVSIGRPIANHSVYVLDEHLRLQPVGVVGELCISGI 3349
                                                     **.:  **::*:*:*: ****.*****:.:
```

FIG. 13 (continued)

```
Paenibacillus_peoriae_A          GLARGYHNQPELMDEKFVDNPFAPGERMYRTGDLVRWLPNGTIEYLGRID 3399
Paenibacillus_polymyxa_A         GLARGYHNRPELMDEKFVDNPFAPGERMYRTGDLVRWLPNGTIEYLGRID 3399
Paenibacillus_polymyxa_PKB1      GLARGYHNRPELMDEKFVDNPFAPGERMYRTGDLVRWLPNGTIEYLGRID 3399
Paenibacillus_polymyxa_E681      GLARGYHNRPELMDEKFVDNPFAPGERMYRTGDLVRWLPNGNIEYLGRID 3399
Paenibacillus_polymyxa_B         GLARGYHNQPELMDEKFVDNPFAPGERMYRTGDLVRWLPNGTIEYLGRID 3399
Paenibacillus_polymyxa_SQR       GLARGYHNQPALMDEKFVDNPFTPGERMYRTGDLVRWLPDGTIEYLGRID 3400
Paenibacillus_polymyxa_C         GLARGYHNQPALMDEKFVDNPFTPGERMYRTGDLVRWLPDGTIEYLGRID 3400
Paenibacillus_polymyxa_M1        GLARGYHNRPELMDEKFVDNPYAPGERMYRTGDLVRWLSNGTIEYLGRID 3400
Paenibacillus_polymyxa_SC2       GLARGYHNRPELMDEKFVDNPYAPGERMYRTGDLVRWLSNGTIEYLGRID 3400
Paenibacillus_sp_NRRL B-50972    GFTREHHNHPELTDEKFVDNPFAPGERMYRTGDLARWLPDGTIQYLGRVD 3099
Paenibacillus_sp_A               GLARGYHNRPALMDEKFVENPFTPGERMYRTGDLVRWLPNGTIEYVGRID 3399
                                 *::* :**:* * *****:**::***********.***.:*.*:*:**:*

Paenibacillus_peoriae_A          HQVKIRGYRIELGEVEAQMLRVPSVQEVVAMAAEGEDGYKDLVAYFVAAQ 3449
Paenibacillus_polymyxa_A         HQVKIRGYRIELGEVEAQMLRVPSVQEVVAMAVEGDDGYKDLVAYFVAAQ 3449
Paenibacillus_polymyxa_PKB1      HQVKIRGYRIELGEVEAQMLRVPSVQEVVAMAVEGDDGYKDLVAYFVAAQ 3449
Paenibacillus_polymyxa_E681      HQVKIRGYRIELGEVEAQMLRVPSVQEVVAMAVEGDDGYKDLVAYFVAAQ 3449
Paenibacillus_polymyxa_B         HQVKIRGYRIELGEVEAQILRVPSVQEVVAMAVEGDDGYKDLVAYFVAAQ 3449
Paenibacillus_polymyxa_SQR       HQVKIRGYRIELGEVEAHMLRVPFVQEVVALAVESEDGYKDLVAYFVAAQ 3450
Paenibacillus_polymyxa_C         HQVKIRGYRIELGEVEAHMLRVPFVQEVVALAVESEDGYKDLVAYFVAAQ 3450
Paenibacillus_polymyxa_M1        HQVKIRGYRIELGEVEAHMLRVPSVQEVVVLAVESDDGYKDLVAYFVAAQ 3450
Paenibacillus_polymyxa_SC2       HQVKIRGYRIELGEVEAHMLRVPSVQEVVVLAVESDDGYKDLVAYFVAAQ 3450
Paenibacillus_sp_NRRL B-50972    HQVKIRGYRVELSEVEAQMLKVQSVQDVVVMAVEGDDGHKDLFAYFVADQ 3149
Paenibacillus_sp_A               HQVKIRGYRIELGEVEAQMLRVQSVQEVVAMAVEGDDGQKDLVAYFVAAR 3449
                                 *********:**.****::*:*  **:**.:*.*.:** ***.***** :
```

FIG. 13 (continued)

```
Paenibacillus_peoriae_A          KLEVSELRAVLSEMLPGYMIPSRFIQLEDMPLTSNGKIDRKALQGERGWA 3499
Paenibacillus_polymyxa_A         KLEVSELRAVLSEILPGYMIPSRFIQLEDMPLTSNGKIDRKALQGERGWA 3499
Paenibacillus_polymyxa_PKB1      KLEVSELRAVLSEMLPGYMIPSRFIQLEDMPLTSNGKIDRKALKGERGWA 3499
Paenibacillus_polymyxa_E681      KLEVSELRAVLSEMLPGYMIPSRFIQLEDMLLTSNGKIDRKALQGERGWA 3499
Paenibacillus_polymyxa_B         KLEVSELRAVLSEMLPGYMIPSRFIQLDDMPLTSNGKVDRKALQGERGWA 3499
Paenibacillus_polymyxa_SQR       KLEVSELRAVLSEMLPGYMIPSRFVQLEDMPLTSNGKIDRKALQGEQGWA 3500
Paenibacillus_polymyxa_C         KLEVSELRAVLSEMLPGYMIPSRFVQLEDMPLTSNGKIDRKALQGEQGWA 3500
Paenibacillus_polymyxa_M1        KLEVSELRADLSEMLPGYMIPSRFIQLEDMPLTSNGKIDRKALQGERGWA 3500
Paenibacillus_polymyxa_SC2       KLEVSELRADLSEMLPGYMIPSRFIQLEDMPLTSNGKIDRKALQGERGWA 3500
Paenibacillus_sp_NRRL B-50972    TIEISELRAVLSELLPVYMIPSHFVQLENPLLTPSGKIDRKALQGERGWA 3199
Paenibacillus_sp_A               ELEVSELQTVLSEMLPGYMIPSRFIQLEDMPLTSNGKINRKALQGERGWA 3499
                                  :*:***:: ***:** *****:*:**::  **..**::****:**:***
```

FIG. 15

```
                                       20                      40                      60
                                        |                       |                       |
NRRL B-50972  TTGCAAAAAA  TTGAGGTATT  GTTGGCTGAT  GACAACCGGG  AATTTACGAA  TCTGCTTGCC  60
NRRL B-67129  TTGCAAAAAA  TTGAGGTATT  GTTGGCTGAT  GACAACCGGG  AATTTACGAA  TCTGCTTGCC  60
                                       80                     100                     120
                                        |                       |                       |
NRRL B-50972  GAATATATTT  CCGATCAGGA  GGATATGGAA  GTTACAGGAA  TCGCCTATAA  TGGTGAAGAA  120
NRRL B-67129  GAATATATTT  CCGATCAGGA  GGATATGGAA  GTTACAGGAA  TCGCCTATAA  TGGTGAAGAA  120
                                      140                     160                     180
                                        |                       |                       |
NRRL B-50972  GTGCTCCAAC  ACATCGCAGA  ATCCCGCAAC  GTACCTGATG  TACTTATTTT  AGATATTATC  180
NRRL B-67129  GTGCTCCAAC  ACATCGCAGA  ATCCCGCAAC  GTACCTGATG  TACTTATTTT  AGATATTATC  180
                                      200                     220                     240
                                        |                       |                       |
NRRL B-50972  ATGCCTCATC  TGGATGGTCT  CGGCGTATTG  GAGCGCTTGA  GAGAAATGAA  CCTGTCTCCA  240
NRRL B-67129  ATGCCTCATC  TGGATGGTCT  CGGCGTATTG  GAGCGCTTGA  GAGAAATGAA  CCTGTCTCCA  240
                                      260                     280                     300
                                        |                       |                       |
NRRL B-50972  CAGCCGAAAA  TCATTATGCT  GACTGCATTC  GGTCAAGAAA  ATATTACGCA  AAGAGCCGTA  300
NRRL B-67129  CAGCCGAAAA  TCATTATGCT  GACTGCATTC  GGTCAAGAAA  ATATTACGCA  AAGAGCCGTA  300
                                      320                     340                     360
                                        |                       |                       |
NRRL B-50972  CAGCTCGGGG  CATCTTATTA  TATTTTGAAG  CCGTTTGACA  TGGAAGTGCT  TGCCAACCGT  360
NRRL B-67129  CAGCTCGGGG  CATCTTATTA  TATTTTGAAG  CCGTTTGACA  TGGAAGTGCT  TGCCAACCGT  360
                                      380                     400                     420
                                        |                       |                       |
NRRL B-50972  GTTCGTCAAT  TGGTGGGACC  ACAATTAGTC  AGCAGCAGTC  CGGTGACGGT  TTCTTCCATG  420
NRRL B-67129  GTTCGTCAAT  TGGTGGGACC  ACAATTAGTC  AGCAGCAGTC  CGGTGACGGT  TTCTTCCATG  420
```

FIG. 15 (continued)

```
                                              440                                    460                                    480
                                                |                                      |                                      |
NRRL B-50972  CGGTCTAATG  TGGTGCCAAT  GGGCAAAACG  AAAAACCTGG  ATGCCAGTAT  TACGGCCATT 480
NRRL B-67129  CGGTCTAATG  TGGTGCCAAT  GGGCAAAACG  AAAAACCTGG  ATGCCAGTAT  TACGGCCATT 480
                                              500                                    520                                    540
                                                |                                      |                                      |
NRRL B-50972  ATCCATGAAA  TCGGTGTGCC  AGCTCATATT  AAGGGCTATC  AATATTTACG  CGAAGCCATT 540
NRRL B-67129  ATCCATGAAA  TCGGTGTGCC  AGCTCATATT  AAGGGCTATC  AATATTTACG  CGAAGCCATT 540
                                              560                                    580                                    600
                                                |                                      |                                      |
NRRL B-50972  ACTATGGTGT  ACAATAATAT  CGAAATTTTG  GGTGCCATCA  CCAAAACATT  ATATCCCGCA 600
NRRL B-67129  ACTATGGTGT  ACAATAATAT  CGAAATTTTG  GGTGCCATCA  CCAAAACATT  ATATCCCGCA 600
                                              620                                    640                                    660
                                                |                                      |                                      |
NRRL B-50972  ATCGCCGAAA  AATTTAAAAC  GACGGCATCC  CGCGTGGAAC  GCGCCATTCG  TCATGCCATC 660
NRRL B-67129  ATCGCCGAAA  AATTTAAAAC  GACGGCATCC  CGCGTGGAAC  GCGCCATTCG  TCATGCCATC 660
                                              680                                    700                                    720
                                                |                                      |                                      |
NRRL B-50972  GAGGTAGCAT  GGACACGTGG  CAACATCGAC  AGCATCTCTC  ATCTGTTCGG  CTACACCATT 720
NRRL B-67129  GAGGTAGCAT  GGACACGTGG  CAACATCGAC  AGCATCTCTC  ATCTGTTCGG  CTACACCATT 720
                                              740                                    760                                    780
                                                |                                      |                                      |
NRRL B-50972  AATATCTCCA  AATCCAAGCC  GACCAACTCA  GAGTTTATTG  CGATGGTAGC  TGACAAGCTT 780
NRRL B-67129  AATATCTCCA  AATCCAAGCC  GACCAACTCA  GAGTTTATTG  CGATGGTAGT  TGACAAGCTT 780
                                              800
                                                |
NRRL B-50972  CGGATTGAGA  ATAAGGTGTC  CTGA 804
NRRL B-67129  CGGATTGAGA  ATAAGGTGTC  CTGA 804
```

FIG. 17 (continued)
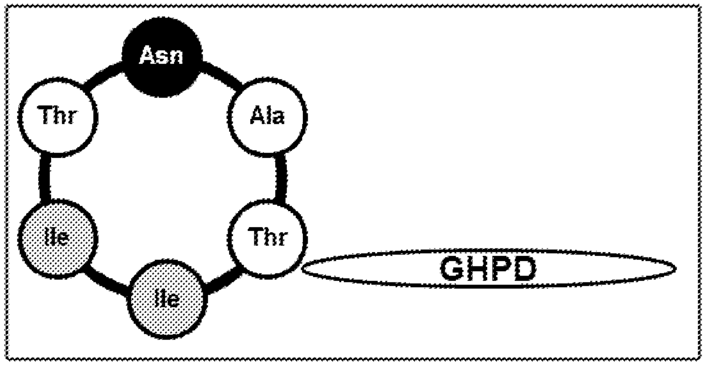
LiF08a
ALTESO $MIC_{80}$: 1.6 µg/mL
COLLLA $MIC_{80}$: 11 µg/mL
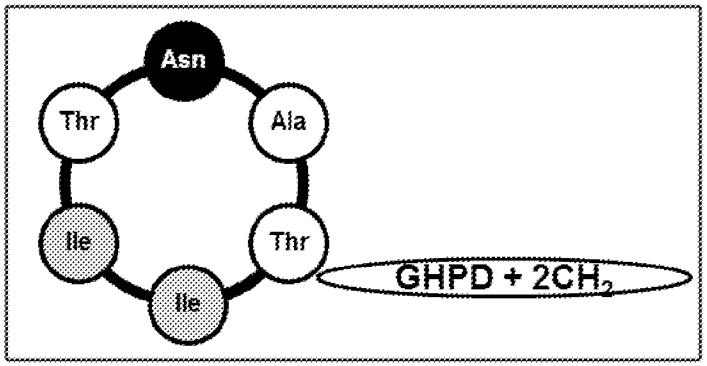
Paeniprolixin C1
ALTESO $MIC_{80}$: 4.8 µg/mL
COLLLA $MIC_{80}$: 5.5 µg/mL
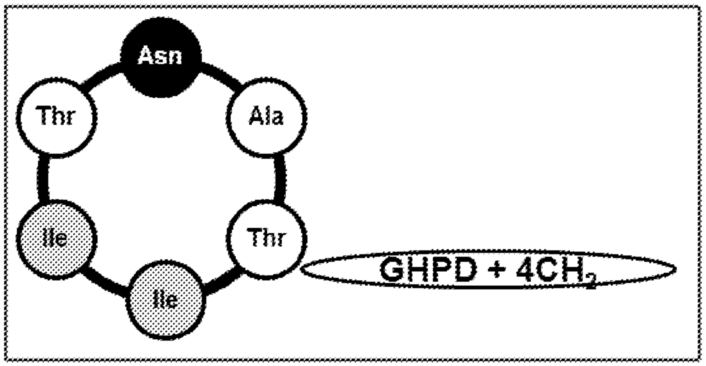
Paeniprolixin G1
ALTESO $MIC_{80}$: 33 µg/mL
COLLLA $MIC_{80}$: >50 µg/mL

SEQUENCE LISTING

```
Sequence total quantity: 20
SEQ ID NO: 1            moltype = AA  length = 550
FEATURE                 Location/Qualifiers
source                  1..550
                        mol_type = protein
                        organism = Paenibacillus peoriae
SEQUENCE: 1
NALVYDPVTI EQIKGHLVHL MEQIVENPAI SVDALELVTP QEREQILNVW GNTKGIYEHC  60
NTFHGLLEEQ AGRTPDATAI WFEDESLTYA ELNAKANGLA RRLRTQGIKT GDLVGLIAER  120
SLEMIVGIYG IMKAGGAYVP IDPEYPKERI SYMLEDSGAK LILTQAHFLE HLGWTENVLL  180
LDESSTYDAD TSNLEDTAGP DDLAYVIYTS GTTGQPKGVL VEHRGLPNLS DVYGAHFEVT  240
PQDRIVQFAS LSFDASVSEI LTALSHGGVL CIPSTEDILD HALFEQFMND KGVTVATLPP  300
AYAIHLDPER LPTLRCLLTA GSAASVELIE EWRKHVRYSN GYGPTEDSVC TTIWSVPDSE  360
EATDIVSIGR PIANHSVYIL DDHFRLQPVG VAGELCISSI GLARGYHNQP ELMDEKFVDN  420
PFAPGERMYR TGDLVRWLPN GTIEYLGRID HQVKIRGYRI ELGEVEAQML RVPSVQEVVA  480
MAAEGEDGYK DLVAYFVAAQ KLEVSELRAV LSEMLPGYMI PSRFIQLEDM PLTSNGKIDR  540
KALQGERGWA                                                       550

SEQ ID NO: 2            moltype = AA  length = 550
FEATURE                 Location/Qualifiers
source                  1..550
                        mol_type = protein
                        organism = Paenibacillus polymyxa
SEQUENCE: 2
NALVYDQVTI GQIKGHLVHL MEQIVENPAI SVDALELVTP QEREQILNVW GNMKGIYEHC  60
NTFHGLLEEQ AGRTPDATAI WFEDESLTYA ELNAKANGLA RRLRTQGIKT GDLVGLIAER  120
SLEMIVGIYG IMKAGGAYVP IDPEYPKERI SYMLEDSGAK LILTQAHLLE HLGWTENVLL  180
LDESSTYDAD TSNLEDTAGP DDLAYVIYTS GTTGQPKGVL VEHRGLPNLS NVYGAHFEVT  240
PQDRIVQFAS LSFDASVSEI LTALSHGGVL CIPSTEDILD HALFEQFMND KGITVATLPP  300
AYAIHLDPER LPTLRCLLTA GSAASVELIE EWRKHVRYSN GYGPTEDSVC TTIWSVPDSE  360
EATDIVSIGR PIANHSVYIL DDHFRLQPVG VAGELCISSI GLARGYHNRP ELMDEKFVDN  420
PFAPGERMYR TGDLVRWLPN GTIEYLGRID HQVKIRGYRI ELGEVEAQML RVPSVQEVVA  480
MAVEGDDGYK DLVAYFVAAQ KLEVSELRAV LSEILPGYMI PSRFIQLEDM PLTSNGKIDR  540
KALQGERGWA                                                       550

SEQ ID NO: 3            moltype = AA  length = 550
FEATURE                 Location/Qualifiers
source                  1..550
                        mol_type = protein
```

```
                         organism = Paenibacillus polymyxa
SEQUENCE: 3
NALVYDPVTI EQIKGHLVHL MEQIVENPAI SVDALELVTP QEREQILNVW GNTKGIYEHC  60
NTFHGLLEEQ AGRTPDATAI WFEDESLTYA ELNAKANGLA RRLRTQGIKT GDLVGLIAER  120
SLEMIVGIYG IMKAGGAYVP IDPEYPKERI SYMLEDSGAK LILTQAHLLE HLGWTENVLL  180
LDESSTYDAD TSNLEDTAGP DDLAYVIYTS GTTGQPKGVL VEHRGLPNLS DVYGTHFEVT  240
PQDRIVQFAS LSFDASVSEI LTALSHGGVL CIPSTQDILD HALFEQFMND KGITVATLPP  300
AYAIHLDPER LPTLRCLLTA GSAASVELIE EWRKHVRYSN GYGPTEDSVC TTIWSVPDSE  360
EATDIVSIGR PIANHSVYIL DDHFRLQPVG VAGELCISSI GLARGYHNRP ELMDEKFVDN  420
PFAPGERMYR TGDLVRWLPN GTIEYLGRID HQVKIRGYRI ELGEVEAQML RVPSVQEVVA  480
MAVEGDDGYK DLVAYFVAAQ KLEVSELRAV LSEMLPGYMI PSRFIQLEDM PLTSNGKIDR  540
KALKGERGWA                                                     550

SEQ ID NO: 4             moltype = AA  length = 550
FEATURE                  Location/Qualifiers
source                   1..550
                         mol_type = protein
                         organism = Paenibacillus polymyxa
SEQUENCE: 4
NALVYDPVTI GQIKGHLVHL MEQIVENPAI SVDALELITP QEREQILNVW GNTKAIYEHY  60
NTFHGLLEEQ AGRTPDAAAI WFEDESLTYA ELNAKANGLA RRLRTQGIKT GDLVGLIAER  120
SLEMIVGIYG IMKAGGAYVP IDPEYPQERI SYMLEDSGAK LILTQAHLLE HLGWTENVLL  180
LDESSTYDAD TSNLEDTAGP DDLAYVIYTS GTTGQPKGVL VEHRGLPNLS DVYGAHFEVT  240
PQDRIVQFAS LSFDASVSEI LTALSHGGVL CIPSAQDILD HALFEQFMND KGITVATLPP  300
AYAIHLDPER LPTLRCLLTA GSTASIELIE EWRKHVRYSN GYGPTEDSVC TTIWSVPDSE  360
EATNIVSIGR PIANHSVYIL DDHFRLQPVG VAGELCISSI GLARGYHNRP ELMDEKFVDN  420
PFAPGERMYR TGDLVRWLPN GNIEYLGRID HQVKIRGYRI ELGEVEAQML RVPSVQEVVA  480
MAVEGDDGYK DLVAYFVAAQ KLEVSELRAV LSEMLPGYMI PSRFIQLEDM LLTSNGKIDR  540
KALQGERGWA                                                     550

SEQ ID NO: 5             moltype = AA  length = 550
FEATURE                  Location/Qualifiers
source                   1..550
                         mol_type = protein
                         organism = Paenibacillus polymyxa
SEQUENCE: 5
NALVYDQVTI EQIKEHLVHL MEQIIENPAT SVDALELVTP QEREQILNVW GNTNVCYEHN  60
STFHGLLEEQ AGRTPDATAL LFGDEMLTYA ELNAKANGLA RRLRTQGIKT GDLVGLIAER  120
SLEMIVGIYG IMKAGGAYVP IDPEYPKERI SYMLEDSGAK LILTQAHLLE HLGWTESVLL  180
LDESSTYDAD TSKLEDTAGP DDLAYVIYTS GTTGQPKGVL VEHRGLPNLS DVYGAHFEVT  240
PQDRIVQFAS LSFDASVSEI LTALSHGGVL CIPSTQDILD HVLFEQFMND KGITVATLPP  300
AYAIHLDPER LPTLRCLLTA GSAASVELIE EWRKHVRYSN GYGPTEDSVC TTIWSVPDSE  360
GATDIVSIGR PIANHSVYIL DDHFRLQPVG VAGELCISGI GLARGYHNQP ELMDEKFVDN  420
PFAPGERMYR TGDLVRWLPN GTIEYLGRID HQVKIRGYRI ELGEVEAQIL RVPSVQEVVA  480
MAVEGDDGYK DLVAYFVAAQ KLEVSELRAV LSEMLPGYMI PSRFIQLDDM PLTSNGKVDR  540
KALQGERGWA                                                     550

SEQ ID NO: 6             moltype = AA  length = 550
FEATURE                  Location/Qualifiers
source                   1..550
                         mol_type = protein
                         organism = Paenibacillus polymyxa
SEQUENCE: 6
NALVYDPATI EQIKGHLFHL MEQIVENPAI SVDALELVTP QEREQILSVW GETEASSKHR  60
TTFHGLLEEQ AARTPDATAI LFENEMLTYA ELNAKANGLA RRLRAEGIKT GDLVGLLVER  120
STDMIVGMYG IMKAGGAYVP IDPEYPKERI NYMLEDSGTK MILTQAHLLE HIGWMGNVLL  180
LEEPSTYDAD ESNLKDTADS DDLAYVIYTS GTTGQPKGVL VEHRGLRNLS DVYRGLFEVT  240
PQDRIVQFAS LSFDASVSEI ITALSHGATL CIPSTQDILD HALFEQFMNS KAITIATLPP  300
AYIIHLEPER LPALRCLLTA GSATSVELIE KWRKHVQYFN GYGPTEDSVC TTMWTVPDSE  360
ETMERVSIGQ PIANHRVYIL DDHFRVLPVG VAGELCISGI GLARGYHNQP ALMDEKFVDN  420
PFTPGERMYR TGDLVRWLPD GTIEYLGRID HQVKIRGYRI ELGEVEAHML RVPFVQEVVA  480
LAVESEDGYK DLVAYFVAAQ KLEVSELRAV LSEMLPGYMI PSRFVQLEDM PLTSNGKIDR  540
KALQGEQGWA                                                     550

SEQ ID NO: 7             moltype = AA  length = 550
FEATURE                  Location/Qualifiers
source                   1..550
                         mol_type = protein
                         organism = Paenibacillus polymyxa
SEQUENCE: 7
NALVYDPSTI EQIKGHLFHL MEQIVENPAI SVDALELVTP QEREQILNVW GETEASSKHR  60
TTFHGLLEEQ AARTPDATAI LFENEMLTYA ELNAKANGLA RRLRAEGIKT GDLVGLLVER  120
STDMIVGMYG IMKAGGAYVP MDPEYPKERI NYMLEDSGTK MILAQAHLLE HIDWMGNVLL  180
LEEPSTYDAD ESNLKDTANS DDLAYVIYTS GTTGQPKGVL VEHRGLRNLS DVYRGLFEVT  240
PQDRIVQFAS LSFDASVSEI ITALSHGATL CIPSTQDILD HALFEQFMNS KAITIATLPP  300
AYIIHLEPER LPALRCLLTA GSATSVELIE KWRKHVQYFN GYGPTEDSVC TTMWTVPDSE  360
ETMERVSIGQ PIANHRVYIL DDHFRVLPVG VAGELCISGI GLARGYHNQP ALMDEKFVDN  420
PFTPGERMYR TGDLVRWLPD GTIEYLGRID HQVKIRGYRI ELGEVEAHML RVPFVQEVVA  480
LAVESEDGYK DLVAYFVAAQ KLEVSELRAV LSEMLPGYMI PSRFVQLEDM PLTSNGKIDR  540
```

-continued

```
KALQGEQGWA                                                        550

SEQ ID NO: 8           moltype = AA  length = 550
FEATURE                Location/Qualifiers
source                 1..550
                       mol_type = protein
                       organism = Paenibacillus polymyxa
SEQUENCE: 8
NALVYDPATI EQIKGHLFHL MEQIVENPAI SVDALELVTP QEREQILNVW GDTGASSKHR  60
TTFHGLLEEQ AGRTPDATAI VFENEVLTYA ELNAKANGLA RRLRAEGIKT GDLVGLIVER  120
STDMIVGMYG IMKAGGAYVP IDPEYPKERI NYMLEDSGTK MILAQAHLLE HRGWTGNVLL  180
LDEPSTYDAD TSNLKDTADP DDLAYVIYTS GTTGRPKGVL VEHRGLQNLS DVYRGLFEVT  240
PQDRIVQFAS LSFDASVSEI LTTLSHGATL CIPSTQEILD HALFEQFMND KGITVATLPP  300
AYAIHLEPER LPTLRCLLTA GSATSVELIE KWRKHVQYFN AYGPTEDSVC TTIWNAQNSE  360
ETVGIVSIGQ PIANHRVYIL DEHFRLLPVG VAGELCISGI GLARGYHNRP ELMDEKFVDN  420
PYAPGERMYR TGDLVRWLSN GTIEYLGRID HQVKIRGYRI ELGEVEAHML RVPSVQEVVV  480
LAVESDDGYK DLVAYFVAAQ KLEVSELRAD LSEMLPGYMI PSRFIQLEDM PLTSNGKIDR  540
KALQGERGWA                                                        550

SEQ ID NO: 9           moltype = AA  length = 550
FEATURE                Location/Qualifiers
source                 1..550
                       mol_type = protein
                       organism = Paenibacillus polymyxa
SEQUENCE: 9
NALVYDPATI EQIKGHLFHL MEQIVENPAI SVDALELVTP QEREQILNVW GDTGASSKHR  60
TTFHGLLEEQ AGRTPDATAI VFENEVLTYA ELNAKANGLA RRLRAEGIKT GDLVGLIVER  120
STDMIVGMYG IMKAGGAYVP IDPEYPKERI NYMLEDSGTK MILAQAHLLE HRGWTGNVLL  180
LDEPSTYDAD TSNLKDTADP DDLAYVIYTS GTTGRPKGVL VEHRGLQNLS DVYRGLFEVT  240
PQDRIVQFAS LSFDASVSEI LTTLSHGATL CIPSTQEILD HALFEQFMND KGITVATLPP  300
AYAIHLEPER LPTLRCLLTA GSATSVELIE KWRKHVQYFN AYGPTEDSVC TTIWNAQNSE  360
ETVGIVSIGQ PIANHRVYIL DEHFRLLPVG VAGELCISGI GLARGYHNRP ELMDEKFVDN  420
PYAPGERMYR TGDLVRWLSN GTIEYLGRID HQVKIRGYRI ELGEVEAHML RVPSVQEVVV  480
LAVESDDGYK DLVAYFVAAQ KLEVSELRAD LSEMLPGYMI PSRFIQLEDM PLTSNGKIDR  540
KALQGERGWA                                                        550

SEQ ID NO: 10          moltype = AA  length = 250
FEATURE                Location/Qualifiers
source                 1..250
                       mol_type = protein
                       organism = Paenibacillus sp.
SEQUENCE: 10
NTLVYDSSNI ERIRGHLVHL MEQIVKNPGI SVDALELVTP QERDHILNIW KDIAVPYEHY  60
AELHAQAQTA PIGQPNVYIV DDHFRLLPVG VAGELCIAGV GFTREHHNHP ELTDEKFVDN  120
PFAPGERMYR TGDLARWLPD GTIQYLGRVD HQVKIRGYRV ELSEVEAQML KVQSVQDVVV  180
MAVEGDDGHK DLFAYFVADQ TIEISELRAV LSELLPVYMI PSHFVQLENP LLTPSGKIDR  240
KALQGERGWA                                                        250

SEQ ID NO: 11          moltype = AA  length = 550
FEATURE                Location/Qualifiers
source                 1..550
                       mol_type = protein
                       organism = Paenibacillus sp.
SEQUENCE: 11
NALVYDQVTI EQIKGHLVHL MEQIVENPAI SVDALELVTP QERELILDVW GNTKVSYEHC  60
NTFHGLLEEQ AGRTPEATAI VFEDEMLTYA ELNAKANGLA RKLRNQGIQT GDLVGLIADR  120
SSEMIVGIYG IMKAGGAYVP IDPEYPKERI SYMLEDSGAK LVLTQARLLE HLGWTENVLL  180
LDEPSTYDAD TSNLKDTVGP DNLAYVIYTS GTTGQPKGVL VEHRGLQNLS DVYGTYFEVT  240
PQDRIVQFAS LSFDASVSEV LTALSHGAAL CIPSTQDILD YALFEQFIND KGITIATLPP  300
AYAIHLEPER LPALRCLLTA GSAASVELIE KWRKHVRYSN GYGPTEDSIC TTIWSVPDSE  360
ETLETVSIGR PIANHSVYVL DEHLRLQPVG VVGELCISGI GLARGYHNRP ALMDEKFVEN  420
PFTPGERMYR TGDLVRWLPN GTIEYVGRID HQVKIRGYRI ELGEVEAQML RVQSVQEVVA  480
MAVEGDDGQK DLVAYFVAAR ELEVSELQTV LSEMLPGYMI PSRFIQLEDM PLTSNGKINR  540
KALQGERGWA                                                        550

SEQ ID NO: 12          moltype = DNA  length = 804
FEATURE                Location/Qualifiers
source                 1..804
                       mol_type = genomic DNA
                       organism = Paenibacillus sp.
SEQUENCE: 12
ttgcaaaaaa ttgaggtatt gttggctgat gacaaccggg aatttacgaa tctgcttgcc  60
gaatatattt ccgatcagga gcatatggaa gttacaggaa tcgcctataa tggtgaagaa  120
gtgctccaac acatcgcaga atcccgcaac gtacctgatg tacttatttt agatattatc  180
atgcctcatc tggatggtct cggcgtattg gagcgcttga gagaaatgaa cctgtctcca  240
cagccgaaaa tcattatgct gactgcattc ggtcaagaaa atattacgca aagagccgta  300
cagctcgggg catcttatta tattttgaag ccgtttgaca tggaagtgct tcccaaccgt  360
gttcgtcaat tggtgggacc acaattagtc agcagcagtc cggtgacggt ttcttccatg  420
cggtctaatg tggtgccaat cggcaaaacg aaaaacctgg atgccagtat tacggccatt  480
```

```
atccatgaaa tcggtgtgcc agctcatatt aagggctatc aatatttacg cgaagccatt  540
actatcgtgt acaataatat cgaaattttg ggtgccatca ccaaaacatt atatcccgca  600
atcgccgaaa aatttaaaac gacggcatcc cgcgtggaac gcgccattcg tcatgccatc  660
gaggtagcat ggacacgtgg caacatcgac agcatctctc atctgttcgg ctacaccatt  720
aatatctcca aatccaagcc gaccaactca gagtttattg cgatggtagc tgacaagctt  780
cggattgaga ataaggtgtc ctga                                          804

SEQ ID NO: 13          moltype = DNA  length = 804
FEATURE                Location/Qualifiers
source                 1..804
                       mol_type = genomic DNA
                       organism = Paenibacillus sp.
SEQUENCE: 13
ttgcaaaaaa ttgaggtatt gttggctgat gacaaccggg aatttacgaa tctgcttgcc  60
gaatatattt ccgatcagga gcatatggaa gttacaggaa tcgcctataa tggtgaagaa  120
gtgctccaac acatcgcaga atcccgcaac gtacctgatg tacttatttt agatattatc  180
atgcctcatc tggatggtct cggcgtattg gagcgcttga gagaaatgaa cctgtctcca  240
cagccgaaaa tcattatgct gactgcattc ggtcaagaaa atattacgca aagagccgta  300
cagctcgggg catcttatta tattttgaag ccgtttgaca tggaagtgct tcccaaccgt  360
gttcgtcaat tggtgggacc acaattagtc agcagcagtc cggtgacggt ttcttccatg  420
cggtctaatg tggtgccaat cggcaaaacg aaaaacctgg atgccagtat tacggccatt  480
atccatgaaa tcggtgtgcc agctcatatt aagggctatc aatatttacg cgaagccatt  540
actatcgtgt acaataatat cgaaattttg ggtgccatca ccaaaacatt atatcccgca  600
atcgccgaaa aatttaaaac gacggcatcc cgcgtggaac gcgccattcg tcatgccatc  660
gaggtagcat ggacacgtgg caacatcgac agcatctctc atctgttcgg ctacaccatt  720
aatatctcca aatccaagcc gaccaactca gagtttattg cgatggtagt tgacaagctt  780
cggattgaga ataaggtgtc ctga                                          804

SEQ ID NO: 14          moltype = AA  length = 267
FEATURE                Location/Qualifiers
source                 1..267
                       mol_type = protein
                       organism = Paenibaciluss terrae
SEQUENCE: 14
MQKIEVLLAD DNREFTNLLA EYISDQEDME VTGIAYNGEE VLQHIAESRN VPDVLILDII  60
MPHLDGLGVL ERLREMNLSP QPKIIMLTAF GQENITQRAV QLGASYYILK PFDMEVLANR  120
VRQLVGPQLV SSSPLTVSSM RSNVVPMGKT KNLDASITAI IHEIGVPAHI KGYQYLREAI  180
TMVYNNIEIL GAITKTLYPA IAEKFKTTAS RVERAIRHAI EVAWTRGNID SISHLFGYTI  240
NISKSKPTNS EFIAMVADKL RIENKVS                                       267

SEQ ID NO: 15          moltype = AA  length = 267
FEATURE                Location/Qualifiers
source                 1..267
                       mol_type = protein
                       organism = Paenibacillus sp.
SEQUENCE: 15
LQKIEVLLAD DNREFTNLLA EYISDQEDME VTGIAYNGEE VLQHIAESRN VPDVLILDII  60
MPHLDGLGVL ERLREMNLSP QPKIIMLTAF GQENITQRAV QLGASYYILK PFDMEVLANR  120
VRQLVGPQLV SSSPVTVSSM RSNVVPMGKT KNLDASITAI IHEIGVPAHI KGYQYLREAI  180
TMVYNNIEIL GAITKTLYPA IAEKFKTTAS RVERAIRHAI EVAWTRGNID SISHLFGYTI  240
NISKSKPTNS EFIAMVADKL RIENKVS                                       267

SEQ ID NO: 16          moltype = AA  length = 267
FEATURE                Location/Qualifiers
source                 1..267
                       mol_type = protein
                       organism = Paenibacillus sp.
SEQUENCE: 16
LQKIEVLLAD DNREFTNLLA EYISDQEDME VTGIAYNGEE VLQHIAESRN VPDVLILDII  60
MPHLDGLGVL ERLREMNLSP QPKIIMLTAF GQENITQRAV QLGASYYILK PFDMEVLANR  120
VRQLVGPQLV SSSPVTVSSM RSNVVPMGKT KNLDASITAI IHEIGVPAHI KGYQYLREAI  180
TMVYNNIEIL GAITKTLYPA IAEKFKTTAS RVERAIRHAI EVAWTRGNID SISHLFGYTI  240
NISKSKPTNS EFIAMVVDKL RIENKVS                                       267

SEQ ID NO: 17          moltype = AA  length = 267
FEATURE                Location/Qualifiers
source                 1..267
                       mol_type = protein
                       organism = Paenibacillus polymyxa
SEQUENCE: 17
MQKIEVLLAD DNREFTNLLA EYISDQEDME VTGIAYNGEE VLQRIAESRN VPDVLILDII  60
MPHLDGLGVL ERLREMNLTP QPKIIMLTAF GQENITQRAV QLGASYYILK PFDMEVLANR  120
VRQLVGPQLV SSSPVTVSSM RSNVVPMGKT KNLDASITAI IHEIGVPAHI KGYQYLREAI  180
TMVYNNIEIL GAITKTLYPA IAEKFKTTAS RVERAIRHAI EVAWTRGNID SISHLFGYTI  240
NISKSKPTNS EFIAMVVDKL RIENKVS                                       267

SEQ ID NO: 18          moltype = AA  length = 267
FEATURE                Location/Qualifiers
source                 1..267
```

-continued

```
                        mol_type = protein
                        organism = Bacillus subtilis
SEQUENCE: 18
MEKIKVCVAD DNRELVSLLS EYIEGQEDME VIGVAYNGQE CLSLFKEKDP DVLVLDIIMP  60
HLDGLAVLER LRESDLKKQP NVIMLTAFGQ EDVTKKAVDL GASYFILKPF DMENLVGHIR  120
QVSGNASSVT HRAPSSQSSI IRSSQPEPKK KNLDASITSI IHEIGVPAHI KGYLYLREAI  180
SMVYNDIELL GSITKVLYPD IAKKFNTTAS RVERAIRHAI EVAWSRGNID SISSLFGYTV  240
SMTKAKPTNS EFIAMVADKL RLEHKAS                                     267

SEQ ID NO: 19           moltype = AA  length = 264
FEATURE                 Location/Qualifiers
source                  1..264
                        mol_type = protein
                        organism = Bacillus cereus
SEQUENCE: 19
MEKIKVCLVD DNKELVSMLE SYVAAQDDME VIGTAYNGQE CLNLLKDKQP DVLVLDIIMP  60
HLDGLAVLEK MRHIERLRQP SVIMLTAFGQ EDVTKKAVDL GASYFILKPF DMENLTSHIR  120
QVSGKANATI KRPLPSFRSA TTVDGKPKNL DASITSIIHE IGVPAHIKGY MYLREAISMV  180
YNDIELLGSI TKVLYPDIAK KYNTTASRVE RAIRHAIEVA WSRGNIDSIS SLFGYTVSMS  240
KAKPTNSEFI AMVADKLRLE HKAS                                        264

SEQ ID NO: 20           moltype = AA  length = 273
FEATURE                 Location/Qualifiers
source                  1..273
                        mol_type = protein
                        organism = Clostridium pasteurianum
SEQUENCE: 20
MEYSKISVLI ADDNKEFCNI LNDYLLNQSD IVVVGIAKDG IEALKLIEEK KPDLVILDII  60
MPNMDGLVVL EKLANINIDP VPNVIVLSAV GQDKITQRAI TLGADYYVVK PFDMDVFTKR  120
IRQMFNNTIL DSETKKTMPI SEKAADVKIS QSVPLDLEDE SIIHEIGVPA HIKGYMYLRE  180
AINMVVDNIE LLSAVTKELY PSIAKKYNTT ASRVERAIRH AIEVAWSRGQ VDTINKLFGY  240
TIHNGKGKPT NSEFIAMIAD KLRLKNKVKN VAQ                              273
```

*PAENIBACILLUS* STRAIN, ANTIFUNGAL COMPOUNDS, AND METHODS FOR THEIR USE

CROSS REFERENCE TO RELATED APPLICATIONS

This application is a continuation of U.S. patent application Ser. No. 16/669,783, filed Oct. 31, 2019, which in turn is a continuation of U.S. patent application Ser. No. 16/190,556, filed Nov. 14, 2018, and issued as U.S. Pat. No. 10,499,656, which in turn is a continuation of U.S. patent application Ser. No. 15/874,577, filed Jan. 18, 2018, and issued as U.S. Pat. No. 10,159,257, which in turn is a continuation of U.S. patent application Ser. No. 15/078,670, filed Mar. 23, 2016, and issued as U.S. Pat. No. 9,883,676, which claims priority to U.S. Provisional Patent Application No. 62/138,765, filed Mar. 26, 2015, and U.S. Provisional Patent Application No. 62/232,205, filed Sep. 24, 2015, the contents of all of which are incorporated herein by reference in their entireties.

REFERENCE TO SEQUENCE LISTING SUBMITTED ELECTRONICALLY

The official copy of the sequence listing is submitted electronically via EFS-Web as an XML-formatted sequence listing with a file named "BCS159002 US02 N N N N.xml" created on Feb. 21, 2023, and having a size of 27 kilobytes, and is filed concurrently with the specification. The sequence listing contained in this XML-formatted document is part of the specification and is herein incorporated by reference in its entirety.

TECHNICAL FIELD

The present invention relates to the field of bacterial strains and their ability to control plant diseases. In particular, the present invention is directed to a *Paenibacillus* sp. strain with a relatively high level of broad spectrum antifungal activity.

BACKGROUND

Fungicides have myriad uses, including for crop protection; as food, feed, and cosmetics preservatives; and as therapeutic agents for both human and veterinary applications. Crop yield reduction, foodborne diseases and fungal infections of both humans and animals are a problem in both developed and developing countries.

Synthetic insecticides or fungicides often are non-specific and therefore can act on organisms other than the target ones, including other naturally occurring beneficial organisms. Because of their chemical nature, they may also be toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i.e., synthetic) pesticides. Thus, there is a need to manage food chain requirements while still allowing effective pest control.

A further problem arising with the use of synthetic insecticides or fungicides is that the repeated and exclusive application of an insecticide or fungicides often leads to selection of resistant pathogenic microorganisms. Normally, such strains are also cross-resistant against other active ingredients having the same mode of action. An effective control of the pathogens with said active compounds is then not possible any longer. However, active ingredients having new mechanisms of action are difficult and expensive to develop.

The risk of resistance development in pathogen populations as well as environmental and human health concerns have fostered interest in identifying alternatives to synthetic insecticides and fungicides for managing plant diseases. The use of biological control agents is one alternative.

Non-ribosomal peptides, such as the fusaricidins, are well-recognized for their antimicrobial properties and have been used in the field of crop protection. Because of their mode of action, they also have potential uses in biopharmaceutical and other biotechnology applications. Fusaricidins can be isolated from *Paenibacillus* sp. and have a ring structure composed of 6 amino acid residues in addition to 15-guanidino-3-hydroxypentadecanoic acid. Fusaricidins isolated from *Paenibacillus polymyxa* include LI-F03, LI-F04, LI-F05, LI-F07 and LI-F08 (Kurusu K, Ohba K, Arai T and Fukushima K., J. Antibiotics, 40:1506-1514, 1987) and additional fusaricidins A, B, C and D have been reported (Kajimura Y and Kaneda M., J. Antibiotics, 49:129-135, 1996; Kajimura Y and Kaneda M., J. Antibiotics, 50:220-228, 1997).

Certain fusaricidins are known to have germicidal activity against plant pathogenic fungi such as *Fusarium oxysporum, Aspergillus niger, Aspergillus oryzae* and *Penicillium thomii*. Some fusaricidins also have germicidal activity against Gram-positive bacteria including *Staphylococcus aureus* (Kajimura Y and Kaneda M., J. Antibiotics, 49:129-135, 1996; Kajimura Y and Kaneda M., J. Antibiotics, 50:220-228, 1997). In addition, it has been found that specific fusaricidins have antifungal activity against *Leptosphaeria maculans* which causes black root rot of canola (Beatty PH and Jensen SE., Can. J. Microbiol., 48:159-169, 2002). There is a need to further characterize the fusaricidin compounds and identify strains of *Paenibacillus* sp. that produce those fusaricidins providing a broad spectrum of antifungal activity at relatively low application rates.

Fusaricidins and other antifungal metabolites may be obtained through fermentation of *Paenibacillus* sp. However, many *Paenibacillus* sp. strains also produce antibiotics known as polymyxins. Polymyxins are selectively toxic to Gram-negative bacteria and may have a neurotoxic or nephrotoxic effect when given to human patients. The global problem of advancing antimicrobial resistance and the relative toxicity of the polymyxins require careful use and administration of these antibiotics. For this reason it is highly desirable that a *Paenibacillus* sp. strain developed for use in agriculture express relatively high levels of the fusaricidins and no detectable polymyxins. Such a strain would pose little or no risk to workers and consumers. In addition, there is a need to identify *Paenibacillus* sp. strains that exhibit a broad spectrum of activity. Improvements to the efficacy of existing fungicides, especially those that are not susceptible to development of fungal resistance, are highly desirable.

SUMMARY

The present invention is directed to a composition comprising a biologically pure culture of a fungicidal *Paenibacillus* sp. strain comprising a variant fusaricidin synthetase lacking a functional adenylation domain in the third module (FusA-A3), wherein the lack of a functional FusA-A3 inhibits synthesis of fusaricidins with a tyrosine or a phenylalanine at amino acid residue (3) compared to synthesis of fusaricidins by a *Paenibacillus* sp. strain comprising a wild-type fusaricidin synthetase. In certain aspects, the variant fusaricidin synthetase comprises a deletion in FusA-A3 of at least one, at least two, at least three, at least four, at least five, at least six, at least seven, at least eight, at least nine, or ten amino acid residues that determine substrate specificity. In other aspects, the amino acid residues are selected from the group consisting of Asp235, Ala236, Ser239, Thr278, Leu299, Ala301, Ala/Gly322, Val330, Cys331, Lys517, and combinations thereof.

In one embodiment, the amino acid residues are located at positions 3203, 3204, 3207, 3246, 3267, 3269, 3290, 3298, 3299, and/or 3486 of SEQ ID NO: 11. In another embodiment, the variant fusaricidin synthetase comprises a deletion in FusA-A3 of Asp235, Ala236, Ser239, Thr278, Leu299, Ala301, Ala/Gly322, Val330, and Cys331. In some embodiments, the variant fusaricidin synthetase comprises SEQ ID NO: 10.

The present invention also provides a composition comprising a biologically pure culture of a fungicidal *Paenibacillus* sp. strain or a cell-free extract thereof comprising at least one Paeniserine and at least one Paeniprolixin.

In certain aspects, the at least one Paeniserine is selected from the group consisting of Paeniserine A1, Paeniserine A2, Paeniserine A3, Paeniserine A4, Paeniserine B1, Paeniserine B2, Paeniserine B3, Paeniserine B4, Paeniserine C1, Paeniserine C2, and Paeniserine C3.

In other aspects, the at least one Paeniprolixin is selected from the group consisting of Paeniprolixin A1, Paeniprolixin A2, Paeniprolixin B1, Paeniprolixin B2, Paeniprolixin C1, Paeniprolixin D1, Paeniprolixin E1, Paeniprolixin E2, Paeniprolixin F1, Paeniprolixin F2, Paeniprolixin G1, and Paeniprolixin G2.

In certain embodiments, the composition comprises fusaricidin A, LiF08a, Paeniserine A1, Paeniserine B1, Paeniprolixin A2, and Paeniprolixin B2.

In some embodiments, the composition does not comprise LiF03a, LiF03b, LiF03c, LiF03d, LiF07a, LiF07b, LiF07c, and/or LiF07d. In other embodiments, the composition comprises Paeniserine A1, Paeniserine B1, Paeniprolixin A2, and Paeniprolixin B2 in a synergistically effective amount.

In certain aspects, the present invention is directed to a composition wherein the *Paenibacillus* sp. strain is *Paenibacillus* sp. strain NRRL B-50972, *Paenibacillus* sp. strain NRRL B-67129, or a fungicidal mutant strain thereof. The composition may comprise a fermentation product of *Paenibacillus* sp. strain NRRL B-50972, *Paenibacillus* sp. strain NRRL B-67129, or a fungicidal mutant strain thereof.

In some embodiments, the fungicidal mutant strain has a genomic sequence with greater than about 90% sequence identity to *Paenibacillus* sp. NRRL B-50972. In other embodiments, the fungicidal mutant strain has fungicidal activity and/or levels of a fusaricidin, Paeniserine, and/or Paeniprolixin that are comparable or better than that of *Paenibacillus* sp. NRRL B-50972. In yet other embodiments, the fermentation product does not comprise a polymyxin.

In some aspects, the fermentation product is a liquid formulation. The liquid formulation may be a suspension concentrate or an oil dispersion. In one embodiment, the composition comprises at least about $1\times10^4$ CFU of the strain/mL of the liquid formulation. In another embodiment, the composition comprises about 1% to about 25% fermentations solids.

In other aspects, the present invention relates to a composition comprising: a) at least one fusaricidin; and b) at least one Paeniserine or at least one Paeniprolixin in a synergistically effective amount. In one embodiment, the Paeniserine is at least one of Paeniserine A1, Paeniserine A2, Paeniserine A3, Paeniserine A4, Paeniserine B1, Paeniserine B2, Paeniserine B3, Paeniserine B4, Paeniserine C1, Paeniserine C2, and Paeniserine C3. In another embodiment, the Paeniprolixin is at least one of Paeniprolixin A1, Paeniprolixin A2, Paeniprolixin B1, Paeniprolixin B2, Paeniprolixin C1, Paeniprolixin D1, Paeniprolixin E1, Paeniprolixin E2, Paeniprolixin F1, Paeniprolixin F2, Paeniprolixin G1, and Paeniprolixin G2.

In particular, in one embodiment the synergistic ratio of the at least one fusaricidin and the at least one Paeniserine or at least one Paeniprolixin lies in the range of 1:1000 to 1000:1, preferably in the range of 1:500 to 500:1, more preferably in the range of 1:250 to 250:1. In another embodiment, the synergistic weight ratio of the at least one fusaricidin and the at least one Paeniserine or at least one Paeniprolixin is in the range of 1:100 to 100:1, preferably in the range of 1:100 to 10:1 or even in the range of 1:50 to 25:1. In one aspect, the fusaricidin is Fusaricidin A. In another aspect, the Paeniserine is Paeniserine A1. In yet another aspect, the Paeniprolixin is Paeniprolixin C1.

In other aspects, the present invention relates to an isolated compound having the structure (I):

(I)

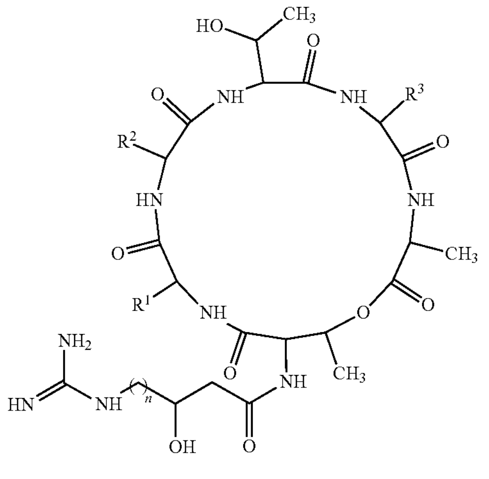

wherein $R^1$ and $R^2$ are each independently $—CH(CH_3)_2$ or $—CH(CH_3)CH_2CH_3$;

$R^3$ is $—CH_2C(O)NH_2$ or $—(CH_2)_2C(O)NH_2$; and n is an integer between 13 and 20;

including salts, hydrates, solvates, polymorphs, optical isomers, geometrical isomers, enantiomers, diastereomers, acyclic analogs, and mixtures thereof.

In some embodiments, $R^3$ is $—CH_2C(O)NH_2$. In other embodiments, $R^3$ is $—(CH_2)_2C(O)NH_2$. In one aspect, $R^1$ is $—CH(CH_3)_2$. In another aspect, $R^1$ is $—CH(CH_3)CH_2CH_3$. In one aspect, $R^2$ is $—CH(CH_3)_2$. In yet another aspect, $R^2$ is $—CH(CH_3)CH_2CH_3$.

In yet other aspects, the present invention relates an isolated compound having the structure (II):

(II)

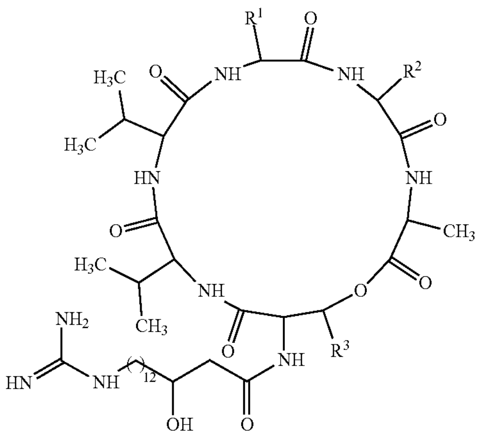

wherein $R^1$ is —$CH_2OH$ or —$CH(OH)CH_3$;

$R^2$ is —$CH_2C(O)NH_2$ or —$(CH_2)_2C(O)NH_2$; and $R^3$ is H or $CH_3$;

with the proviso that if $R^1$ is —$CH_2OH$ and $R^2$ is —$CH_2C(O)NH_2$ then $R^3$ is H;

including salts, hydrates, solvates, polymorphs, optical isomers, geometrical isomers, enantiomers, diastereomers, acyclic analogs, and mixtures thereof.

In some embodiments, $R^3$ is $CH_3$. In other embodiments, $R^3$ is H. In one aspect, $R^1$ is —$CH_2OH$. In another aspect, $R^1$ is —$CH(OH)CH_3$. In one aspect, $R^2$ is —$CH_2C(O)NH_2$. In yet another aspect, $R^2$ is —$(CH_2)_2C(O)NH_2$.

In one embodiment, the present invention is directed to a composition comprising an isolated compound disclosed herein and an agriculturally acceptable carrier.

In certain embodiments, the present invention is directed to a solution comprising a compound of structure (I) wherein the concentration of the compound is at least 0.001 mg/mL, at least 0.01 mg/mL, or at least 0.1 mg/mL. In another embodiment, the present invention is directed to a solution comprising a compound of structure (II) wherein the concentration of the compound is at least 0.001 mg/mL, at least 0.01 mg/mL, or at least 0.1 mg/mL. In certain aspects, the disclosed solutions further comprise an agriculturally acceptable carrier.

In yet another embodiment, the present invention relates to a method of treating a plant to control a disease, wherein the method comprises applying an effective amount of a composition disclosed herein to the plant, to a part of the plant and/or to a locus of the plant. In certain aspects, the composition is a fermentation product of the *Paenibacillus* sp. strain NRRL B-50972, *Paenibacillus* sp. strain NRRL B-67129, or a fungicidal mutant strain thereof. In other aspects, the method comprises applying the composition to foliar plant parts. In yet other aspects, the composition is applied at about $1\times10^{10}$ to about $1\times10^{12}$ colony forming units (CFU) of *Paenibacillus* sp. strain NRRL B-50972, *Paenibacillus* sp. strain NRRL B-67129, or a fungicidal mutant strain thereof per hectare. In one embodiment, the composition is applied at about 0.5 kg to about 5 kg fermentation solids per hectare.

In some aspects, the plant disease is caused by a fungus. In other aspects the plant disease is mildew or a rust disease. In one embodiment, the mildew is powdery mildew or downy mildew. In another embodiment, the rust disease is selected from the group consisting of wheat leaf rust, leaf rust of barley, leaf rust of rye, brown leaf rust, crown rust, and stem rust.

In some embodiments, the fungus is selected from the group consisting of *Alternaria alternata, Alternaria solani, Botrytis cinerea, Colletotrichum lagenarium, Fusarium culmorum, Phaeosphaeria nodorum, Zymoseptoria tritici, Phytophthora cryptogea, Phytophthora infestans, Pythium ultimum, Magnaporthe oryzae, Thanatephorus cucumeris, Ustilago segetum* var. *avenae, Uromyces appendiculatus*, and *Puccinia triticina.*

In other embodiments, the plant disease is caused by bacteria. In one aspect, the bacteria are selected from the group consisting of *Xanthomonas campestris, Pseudomonas syringae*, and *Erwinia carotovora.*

The present invention also relates to the use of the discloses compositions for controlling a phytopathogenic organism in useful plants. In certain aspects, the phytopathogenic organism is selected from the group consisting of *Alternaria alternata, Alternaria solani, Botrytis cinerea, Colletotrichum lagenarium, Fusarium culmorum, Phaeosphaeria nodorum, Zymoseptoria tritici, Phytophthora cryptogea, Phytophthora infestans, Pythium ultimum, Magnaporthe oryzae, Thanatephorus cucumeris, Ustilago segetum* var. *avenae, Uromyces appendiculatus*, and *Puccinia* triticina. In other aspects, the phytopathogenic organism is selected from the group consisting of *Xanthomonas campestris, Pseudomonas syringae*, and *Erwinia carotovora.*

In yet other aspects, the useful plants are selected from the group consisting of apples, bananas, citrus, kiwi, melons, peaches, pears, pineapple, pome fruit, pomegranate, cabbage, cauliflower, cucumbers, cucurbits, tomatoes, potatoes, wheat, rice and soybeans.

BRIEF DESCRIPTION OF THE DRAWINGS

FIG. 2 depicts the in vitro antifungal activity of fusaricidin extracts from the whole broths of *Paenibacillus* sp. strains against *Alternaria alternata* (ALTEAL), *Botrytis cinerea* (BOTRCI), *Fusarium culmorum* (FUSACU), Phaeosphaeria *nodorum* (LEPTNO), Zymoseptoria *tritici* (SEPPTR), *Phytophthora cryptogea* (PHYTCR), *Phytophthora infestans* (PHYTIN), *Pythium ultimum* (PYTHUL), *Magnaporthe oryzae* (PYRIOR), *Thanatephorus cucumeris* (RHIZSO), *Ustilago segetum* var. *avenae* (USTIAV), and *Uromyces appendiculatus* (UROMAP).

FIG. 4C depicts the known fusaricidins detectable in a cell extract from *Paenibacillus* sp. strain NRRL B-50972 and/or strains derived therefrom.

FIG. 5C depicts the Paeniserines detectable in a cell extract from *Paenibacillus* sp. strain NRRL B-50972 and/or strains derived therefrom. The m/z values and retention times (RT) are shown for all detected compounds.

FIG. 8C depicts the Paeniprolixins detectable in a cell extract from *Paenibacillus* sp. strain NRRL B-50972 and/or strains derived therefrom. The m/z values and retention times (RT) are shown for all detected compounds.

FIG. 12A shows the chemical structure of fusaricidin A and a simplified depiction of this structure. FIGS. 12B-12E depict simplified depictions of combinations of fusaricidins, Paeniserines, and/or Paeniprolixins produced by *Paenibacillus* sp. strain NRRL B-50972 and strains derived therefrom. Combinations such as these may produce a synergistic antifungal effect and are responsible for the relatively high efficacy and broad spectrum antifungal activity observed with *Paenibacillus* sp. strain NRRL B-50972 and strains derived therefrom.

FIG. 13 presents a multiple sequence alignment of a segment of the FusA fusaricidin synthetase expressed by the following *Paenibacillus* strains: *Paenibacillus peoriae* A (SEQ ID NO: 1); *Paenibacillus polymyxa* A (SEQ ID NO: 2); *Paenibacillus polymyxa* PKB1 (GenBank ABQ96384.2; SEQ ID NO: 3); *Paenibacillus polymyxa* E681 (GenBank ADM67985.1; SEQ ID NO: 4); *Paenibacillus polymyxa* B (SEQ ID NO: 5); *Paenibacillus polymyxa* SQR (GenBank AHM63812.1; SEQ ID NO: 6); *Paenibacillus polymyxa* C (SEQ ID NO: 7); *Paenibacillus polymyxa* M1 (GenBank CCC83015.1; SEQ ID NO: 8); *Paenibacillus polymyxa* SC2 (GenBank ACA09733.2; SEQ ID NO: 9); *Paenibacillus* sp. strain NRRL B-50972 (SEQ ID NO: 10); and *Paenibacillus* sp. strain A (SEQ ID NO: 11). The amino acid residues that determine substrate specificity are identified with a black outline (see also Table 1). These amino acid residues are located at positions 3203, 3204, 3207, 3246, 3267, 3269, 3290, 3298, 3299, and 3486 of SEQ ID NOs: 1-5 and 11 and at positions 3204, 3205, 3208, 3247, 3268, 3270, 3291, 3299, 3300, and 3487 of SEQ ID NOs: 6-9.

FIG. 15 depicts a sequence alignment of the spo0A gene in *Paenibacillus* sp. strain NRRL B-50972 (SEQ ID NO: 12) and *Paenibacillus* sp. strain NRRL B-67129 (SEQ ID NO: 13).

DETAILED DESCRIPTION

Figure 1:
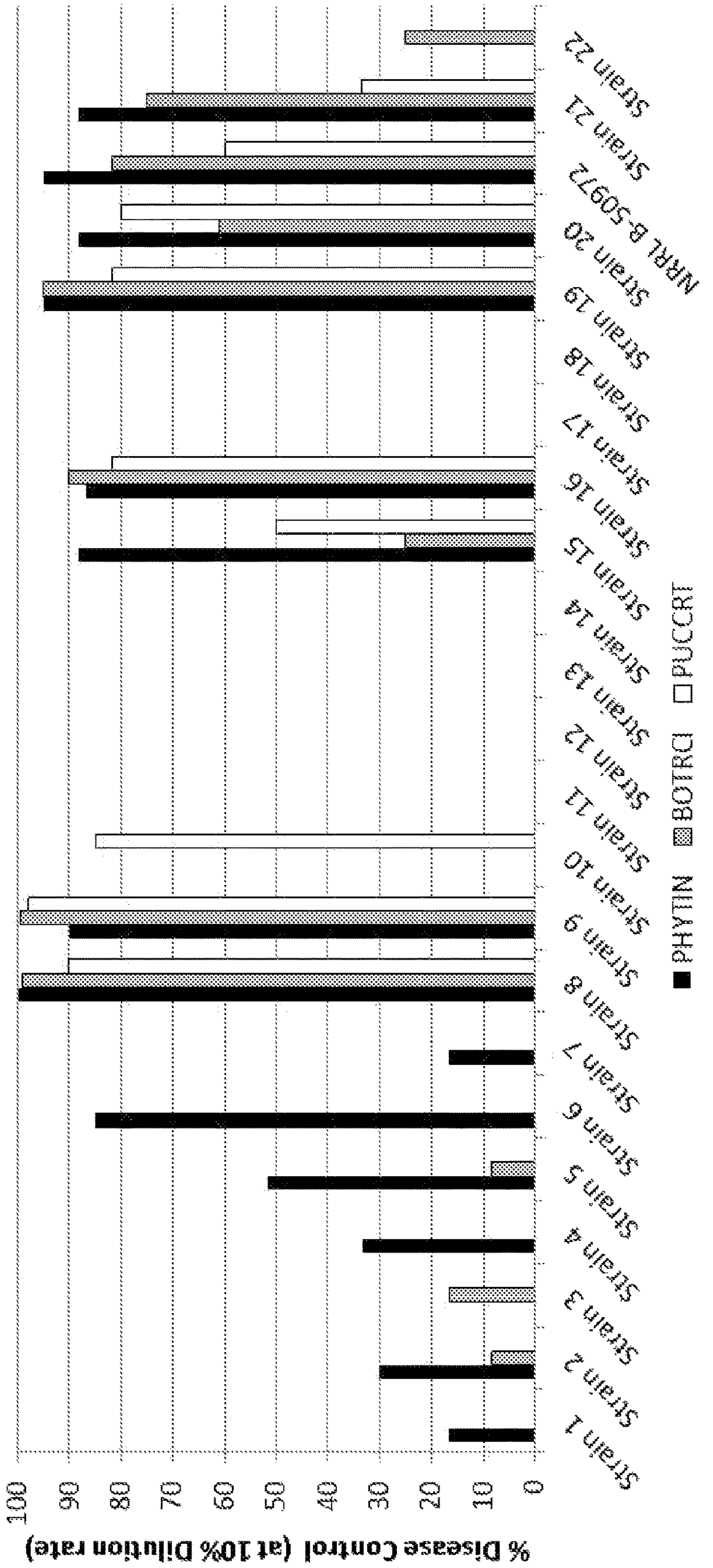
FIG. 1 depicts in planta fungicidal activity of whole broths of *Paenibacillus* sp. strains against Tomato Late Blight (PHYTIN), Grey Mould (BOTRCI), and Wheat Leaf Rust (PUCCRT).
Figure 3:
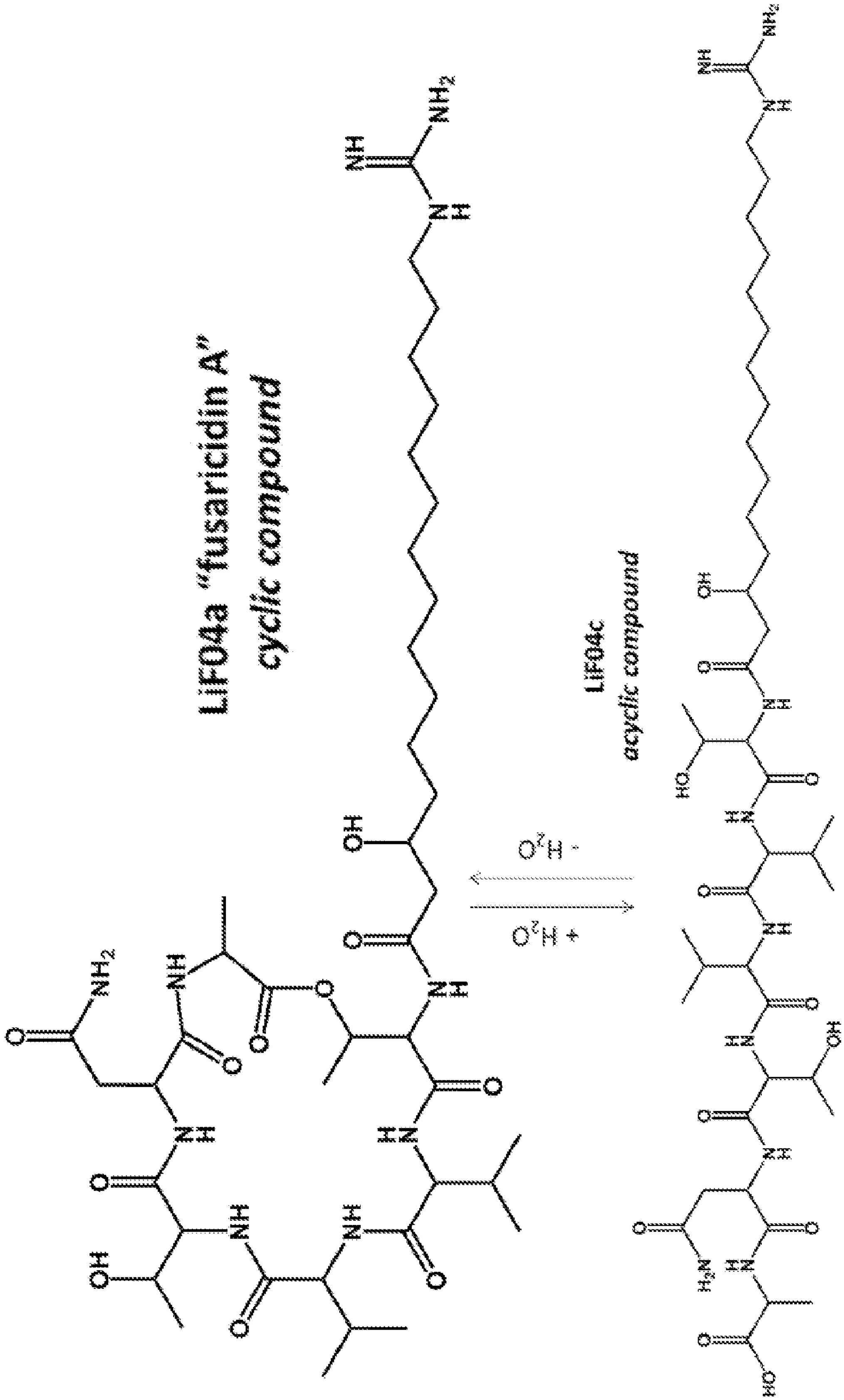
FIG. 3 shows the opening of the ring structure in LiF04a (also known as fusaricidin A) to produce the acyclic analog, LiF04c. Acyclic analogs of each of the fusaricidins and fusaricidin-like compounds occur in a similar manner.

The present invention provides the *Paenibacillus* sp. strain NRRL B-50972 or a fungicidal mutant (strain) derived therefrom. It has been found that the *Paenibacillus* sp. strain NRRL B-50972 has a broad spectrum of activity against phytopathogens.

The microorganisms and particular strains described herein, unless specifically noted otherwise, are all separated from nature and grown under artificial conditions such as in shake flask cultures or through scaled-up manufacturing processes, such as in bioreactors to maximize bioactive metabolite production, for example. Growth under such conditions leads to strain "domestication." Generally, such a "domesticated" strain differs from its counterparts found in nature in that it is cultured as a homogenous population that is not subject to the selection pressures found in the natural environment but rather to artificial selection pressures.

As used herein, the term "isolated" refers to a compound that has been enriched or concentrated in a whole broth or fermentation product or is partially or substantially purified from a whole broth or fermentation product.

In one embodiment, a mutant strain of the *Paenibacillus* sp. strain NRRL B-50972 is provided. The term "mutant" refers to a genetic variant derived from *Paenibacillus* sp. strain NRRL B-50972. In one embodiment, the mutant has one or more or all the identifying (functional) characteristics of *Paenibacillus* sp. strain NRRL B-50972. In a particular instance, the mutant or a fermentation product thereof controls (as an identifying functional characteristic) fungi, Oomycetes and/or bacteria at least as well as the parent

*Paenibacillus* sp. strain NRRL B-50972. Such mutants may be genetic variants having a genomic sequence that has greater than about 85%, greater than about 90%, greater than about 95%, greater than about 98%, or greater than about 99% sequence identity to *Paenibacillus* sp. strain NRRL B-50972. Mutants may be obtained by treating *Paenibacillus* sp. strain NRRL B-50972 cells with chemicals or irradiation or by selecting spontaneous mutants from a population of *Paenibacillus* sp. strain NRRL B-50972 cells (such as phage resistant or antibiotic resistant mutants) or by other means well known to those practiced in the art.

The *Paenibacillus* sp. strain NRRL B-50972 and mutants thereof have activity against a broad range of plant pathogens. In one aspect, the strain has activity against fungi, such as cucumber anthracnose, cucumber powdery mildew, wheat leaf rust, barley powdery mildew and *botrytis*; Oomycetes, such as tomato late blight, cucumber downy mildew and *brassica* downy mildew; and/or bacteria, such as *Pseudomonas, Xanthomonas*, and *Erwinia.*

In certain aspects, the *Paenibacillus* sp. strain comprises a DNA sequence exhibiting at least 75% sequence identity, at least 80% sequence identity, at least 90% sequence identity, at least 95% sequence identity, at least 96% sequence identity, at least 97% sequence identity, at least 98% sequence identity, or at least 99% sequence identity to SEQ ID NO: 10.

In certain aspects, the present invention is directed to a fermentation product comprising a *Paenibacillus* sp. strain, wherein the *Paenibacillus* sp. strain produces fusaricidins, Paeniserines, and/or Paeniprolixins. The fusaricidins are a family of depsipeptides with a 15-guanidino-3-hydroxypentadecanoic acid (GHPD) tail, as well as their linear counterparts. The specific conserved characteristics of fusaricidins are this GHPD tail, as well as three of the six amino acids in the sequence: (1) Threonine, (4) Threonine, and (6) Alanine.

Originally discovered but not characterized by Nakajima et al. (*J. Antibiot.* 1972, 25, 243-247) in the mid-70's, fusaricidins were described by Kurusu et al. (*J. Antibiot.,* 1987, 40, 1506-1514) in the late 1980's. They were further studied by Kajimura et al. (*J. Antibiot.,* 1996, 49, 129-135; *J. Antibiot.,* 1997 50, 220-228), Kuroda et al. (*Heterocycles,* 2000, 53, 1533-1549; *J. Mass Spectrom.,* 2001, 36, 30-37), and Beatty et al. (*Can. J. Microbiol.,* 2002, 48, 159-169) throughout the mid-1990's to the early 2000's. During this period of heavy investigation these compounds were renamed several times depending on the author (Fusaricidin A is also known as LiF04a, Gatavalin, or even KT-6291A). Though there are many publications on the topic, select compounds from the same group of 24 known fusaricidins is described each time.

After a somewhat quiet period on the topic, Vater et al. (J. Am. Soc. Mass Spectrom., 2015, 26, 1130-1141) described the structural elucidation of fusaricidins by mass spectrometry and described several analogs of the family. Vater et al. identified a new class of fusaricidin-like compounds with seven amino acids (i.e., an extra alanine connected to the (4) threonine residue in the peptide sequence). As used herein, the term "acyclic analog" refers to the compound that corresponds to the fusaricidin or fusaricidin-like compound (e.g., a Paeniserine or Paeniprolixin) but lacks the ester bond, resulting in a linear structure.

The amino acid chains of fusaricidins are linked together and modified by a non-ribosomal peptide synthetase (NRPS). The multi-domain NRPS consists of up to 15,000 amino acids and is therefore considered among the longest proteins in nature (Schwarzer et al., (2003) Nonribosomal Peptides: From Genes to Products. Nat. Prod. Rep. 20, 275-287). NRPS incorporation is not limited to the 21 standard amino acids translated by the ribosome, and this promiscuity contributes to the great structural diversity and biological activity of non-ribosomal peptides (Li and Jensen, (2008). Nonribosomal biosynthesis of fusaricidins by *Paenibacillus polymyxa* PKB1 involves direct activation of a d-amino acid. Chem. Biol. 15, 118-127).

In *P. polymyxa* E68, the fusaricidin biosynthetic gene cluster (fusGFEDCBA) has been characterized, and the NRPS coding sequence, the largest coding DNA sequence (CDS) in the cluster, was observed to encode a six-module peptide (Choi et al., Identification and Functional Analysis of the Fusaricidin Biosynthetic Gene of *Paenibacillus polymyxa* E681. Biochem. Biophys. Res. Commun. 365, 89-95; Li and Jensen, Identification and Functional Analysis of the Fusaricidin Biosynthetic Gene of *Paenibacillus polymyxa* E681. Biochem. Biophys. Res. Conunun. 365, 89-95; Li et al., (2013). Promoter Analysis and Transcription Regulation of fus Gene Cluster Responsible for Fusaricidin Synthesis of *Paenibacillus polymyxa* SQR-21. Appl. Microbiol. Biotechnol. 97, 9479-9489). The biosynthetic cluster includes other CDS responsible for biosynthesis of the lipid moiety but does not contain transporter genes (Li and Jensen, (2008). Nonribosomal Biosynthesis of Fusaricidins by *Paenibacillus polymyxa* PKB1 Involves Direct Activation of a d-amino acid. Chem. Biol. 15, 118-127). In *P. polymyxa*, a promoter for the fus operon was identified and shown to be bound by a transcriptional repressor (AbrB) which previous studies implicated as a regulator of sporulation; this is of interest since fusaricidin was observed to be synthesized during sporulation, thus coordinating the microbe's secondary metabolism with its life cycle (Li et al., (2013). Promoter Analysis and Transcription Regulation of fus Gene Cluster Responsible for Fusaricidin Synthesis of *Paenibacillus polymyxa* SQR-21. Appl. Microbiol. Biotechnol. 97, 9479-9489).

Allelic diversity is typically thought to be responsible for producing chemical diversity. However, an interesting feature of the fus cluster is that a diversity of fusaricidins, differing in their incorporated amino acids (Tyr, Val, Ile, allo-Ile, Phe), can be produced by a single allele of fusA; the underlying mechanism is that the NRPS A-domain, responsible for recognition of amino acids, has relaxed substrate specificity (Han et al., (2012). Site-Directed Modification of the Adenylation Domain of the Fusaricidin Nonribosomal Peptide Synthetase for Enhanced Production of Fusaricidin Analogs. Biotechnol. Lett. 34, 1327-1334; Mousa et al., (2015) Biodiversity of Genes Encoding Anti-Microbial Traits within Plant Associated Microbes, Front Plant Sci. 2015; 6: 231).

The structure of the A-domain, which is responsible for substrate recognition and activation in the fusA gene, has been determined from GrsA using X-ray crystallography, and the 10 amino acid residues that determine substrate specificity have been identified (Asp235, Ala236, Trp239, Thr278, Ile299, Ala301, Ala322, Ile330, Cys331, and Lys517) (Challis et al., (2000) Predictive, Structure-Based Model of Amino Acid Recognition by Nonribosomal Peptide Synthetase Adenylation Domains. Chem Biol 7:211-224; Stachelhaus et al., (1999) The Specificity Conferring Code of Adenylation Domains in Nonribosomal Peptide Synthetases. Chem Biol 6:493-505). These 10 signature residues can be classified into three subgroups based on their function within the substrate binding site. Asp235 and Lys517 interacted with the carboxyl and amino ends of the substrate, respectively, and sequence analysis revealed that their position in the A-domain of NRPSs was invariant. Ala236, Ala301 and Ile330 are moderately variable within the A-domains specific to the amino acid substrates having aliphatic side chain. Trp239, Thr278, Ile299, Ala322 and Cys331 are highly variable positions and are thought to be important in the discrimination and selection of different substrates (Challis et al., (2000) Predictive, Structure-Based Model of Amino Acid Recognition by Nonribosomal Peptide Synthetase Adenylation Domains. Chem Biol 7:211-224; Stachelhaus et al., (1999) The Specificity Conferring Code of Adenylation Domains in Nonribosomal Peptide Synthetases. Chem Biol 6:493-505). Ile299 was the most variable position of all within the sequence that confers substrate specificity (Stachelhaus et al., (1999) The Specificity Conferring Code of Adenylation Domains in Nonribosomal Peptide Synthetases. Chem Biol 6:493-505).

The 10 amino acid residues that determine substrate specificity in the fusaricidin synthetase are shown in Table 1. The adenylation domains (A domains) for each of the six modules in the synthetase are known as FusA-A1 for the first module, FusA-A2 for the second module, FusA-A3 for the third module, etc. These 10 amino acid residues are also identified in the multiple sequence alignment of FusA from various *Paenibacillus* sp. strains presented in FIG. 13.

TABLE 1

| A | Residue Positions Involved in Substrate Recognition | | | | | | | | | | Corresponding Residue in |
|---|---|---|---|---|---|---|---|---|---|---|---|
| Domain | 235 | 236 | 239 | 278 | 299 | 301 | 322 | 330 | 331 | 517 | Fusaricidin |
| FusA-A1 | D | F | W | N | I | G | M | V | H | K | L-Thr |
| FusA-A2 | D | A | F | W | L | G | C | T | F | K | D-Val, D-allo-Ile, or D-Ile |
| FusA-A3 | D | A | S | T | L | A | G | V | C | K | L-Tyr, L-Phe, L-Val, L-Ile, or L-allo-Ile |
| FusA-A4 | D | F | W | N | I | G | M | V | H | K | D-allo-Thr |
| FusA-A5 | D | L | T | K | I | G | E | V | G | K | D-Asn or D-Gln |
| FusA-A6 | D | F | P | N | F | C | I | V | Y | K | D-Ala |

In certain aspects, the fungicidal *Paenibacillus* sp. strain expresses a variant fusaricidin synthetase comprising a deletion of at least one, at least two, at least three, at least four, at least five, at least six, at least seven, at least eight, at least nine, or all ten of the amino acid residues that determine substrate specificity in FusA-A3. In other aspects, the fungicidal *Paenibacillus* sp. strain expresses a fusaricidin synthetase with a deletion in FusA-A3 of at least one amino acid residue selected from the group consisting of Asp235, Ala236, Ser239, Thr278, Leu299, Ala301, Ala/Gly322, Val330, Cys331, Lys517, and combinations thereof.

The deletions in FusA-A3 disclosed herein affect the ability of the fusaricidin synthetase to incorporate specific amino acids at amino acid position (3) of the peptide ring in the fusaricidin or fusaricidin-like compound. For example, *Paenibacillus* sp. strain NRRL B-50972 comprises deletions in FusA-A3 and cannot produce fusaricidin compounds with a tyrosine amino acid or phenylalanine amino acid at amino acid position (3). Without wishing to be bound to any theory, it may be that deletions in FusA-A3 shift metabolism away from biosynthesis of the classic fusaricidins and towards biosynthesis of fusaricidin-like compounds such as the Paeniserines and Paeniprolixins.

In certain embodiments, the present invention is directed to a composition comprising a biologically pure culture of a fungicidal *Paenibacillus* sp. strain comprising a variant fusaricidin synthetase lacking a functional adenylation domain in the third module (FusA-A3), further comprising at least one Paeniserine and at least one Paeniprolixin. In certain aspects, the at least one Paeniserine and at least one Paeniprolixin are isolated or enriched in the composition.

In some embodiments, the isolated compound or Paeniprolixin is (Ia)

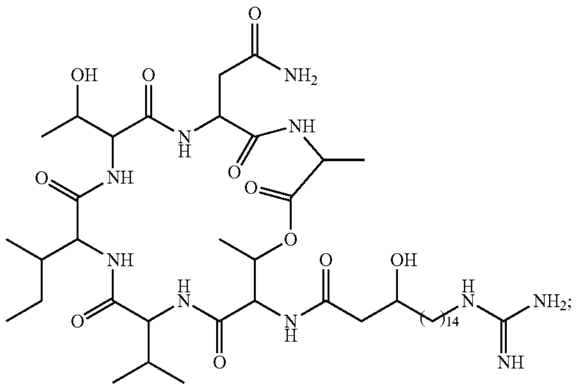

(Ib)

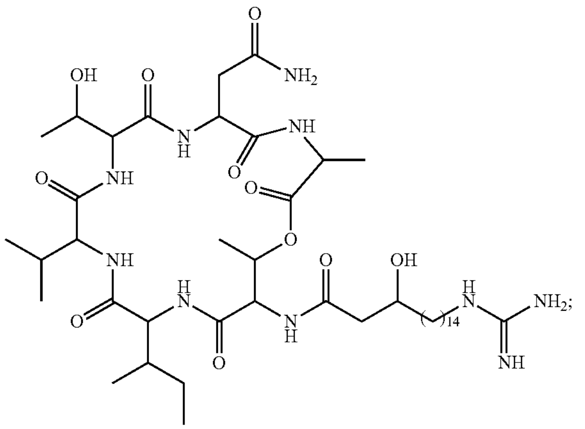

-continued
(Ic)
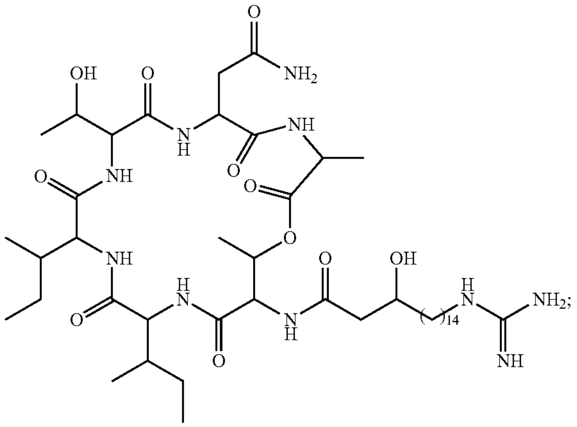
(Id)
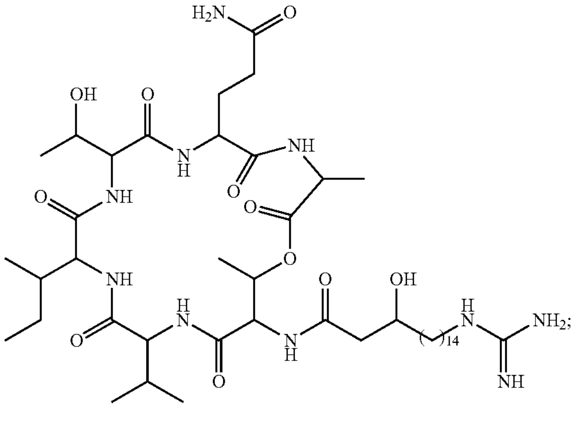
(Ie)
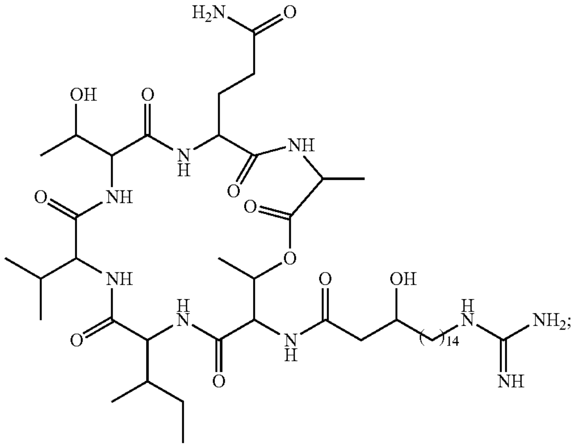
-continued
(If)
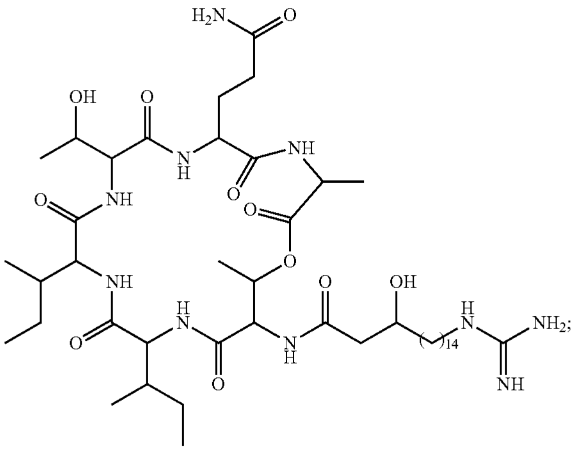
(Ig)
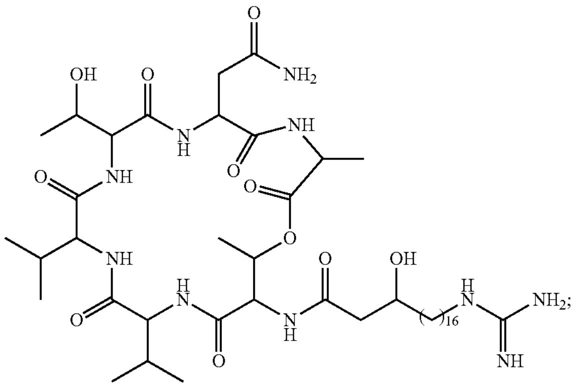
(Ih)
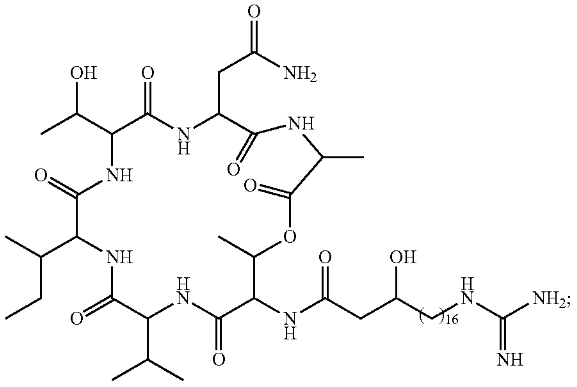

-continued
(Ii)
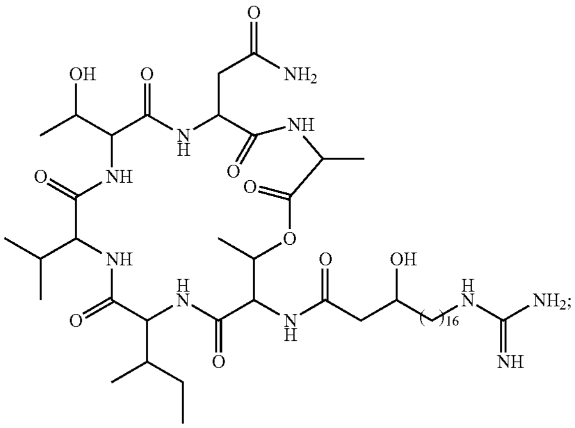
(Ij)
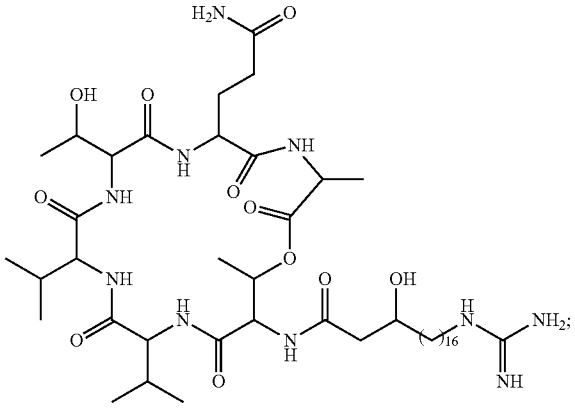
(Ik)
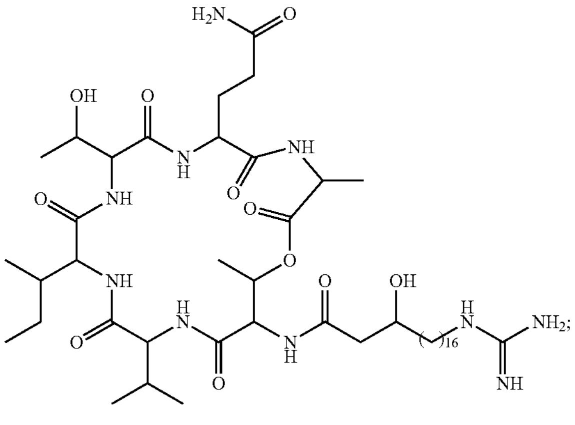
-continued
(Il)
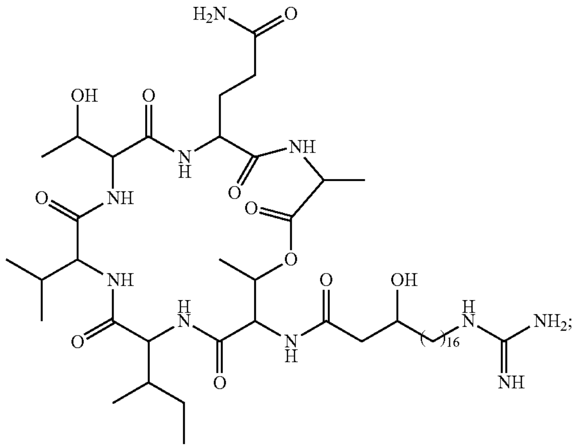
(Im)
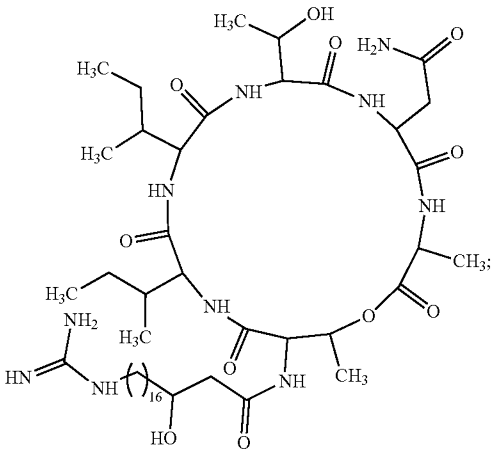
or
(In)
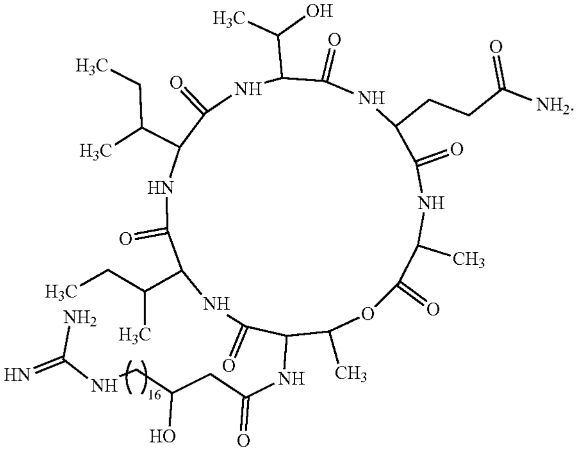

In some embodiments, the isolated compound or Paeniserine is
(IIa)
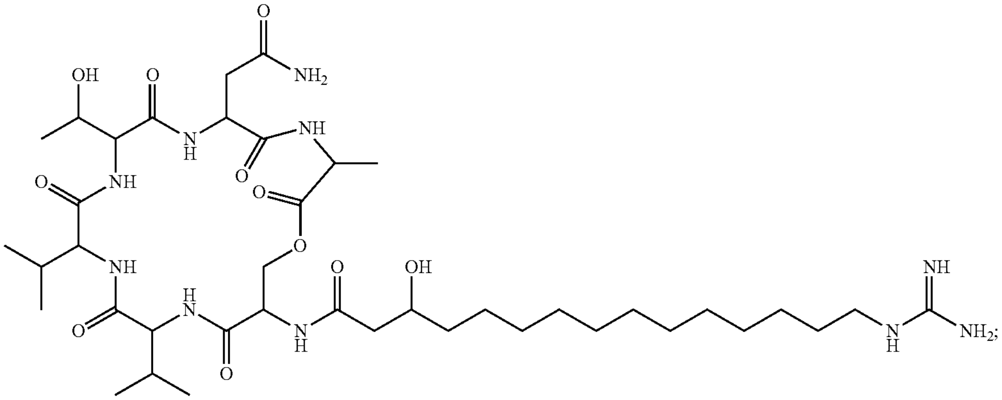
(IIb)
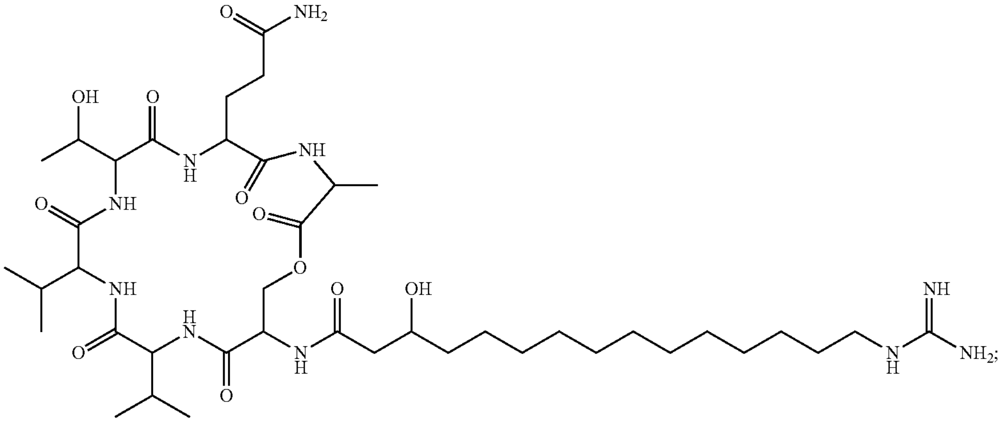
(IIc)
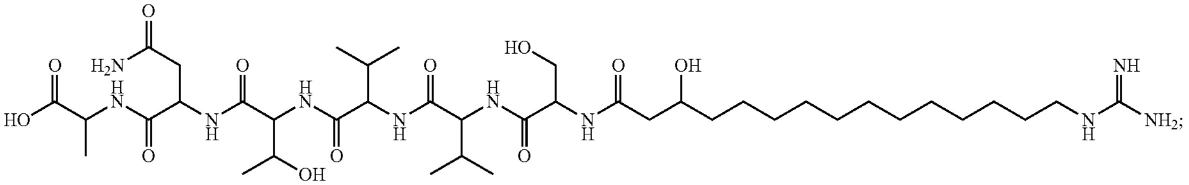
(IId)
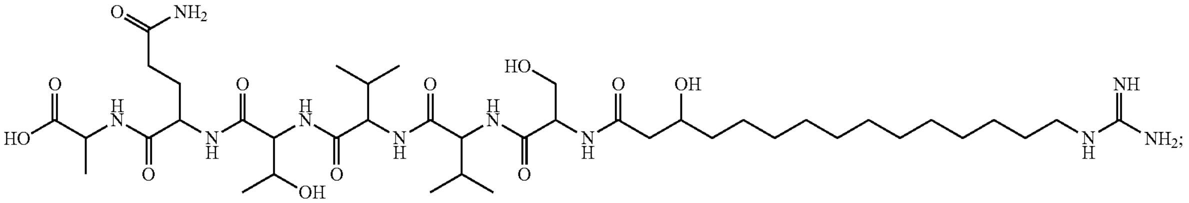

-continued
(IIe)
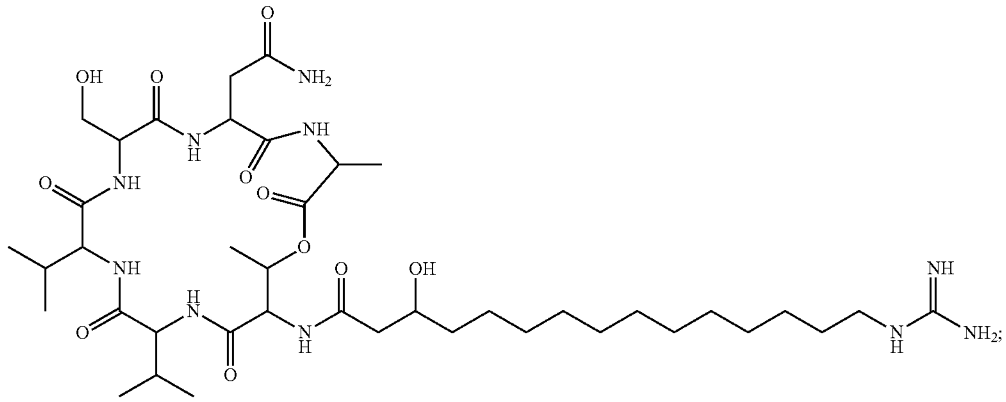
(IIf)
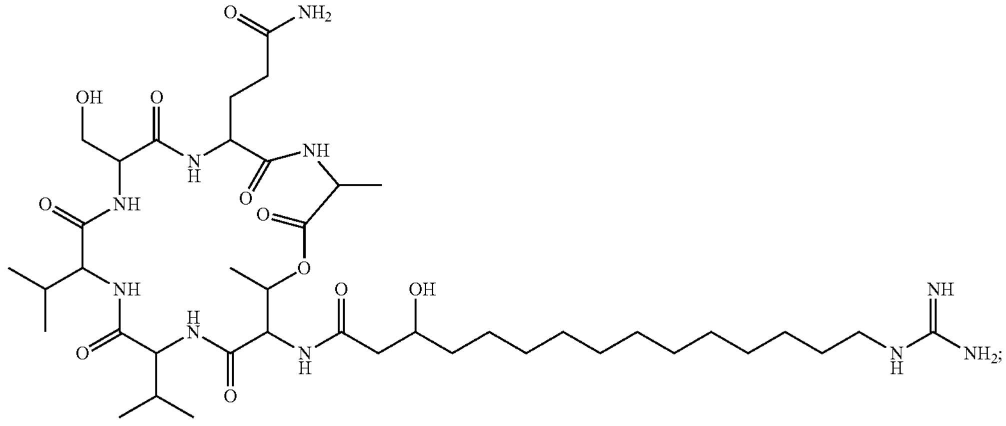
(IIg)
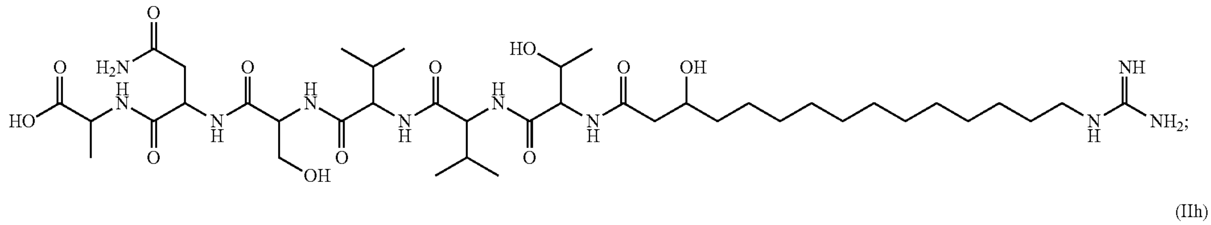
(IIh)
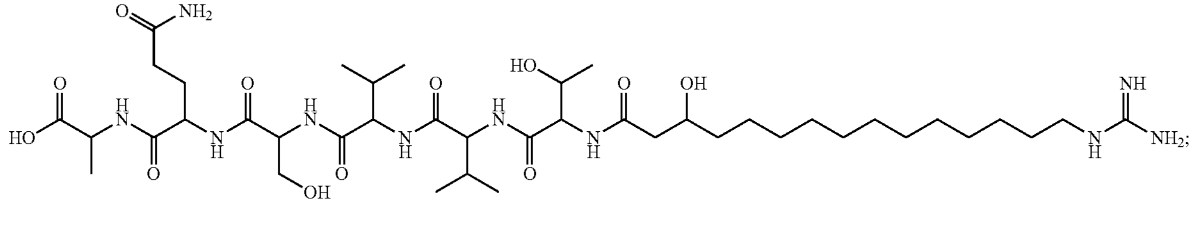

-continued (IIi)

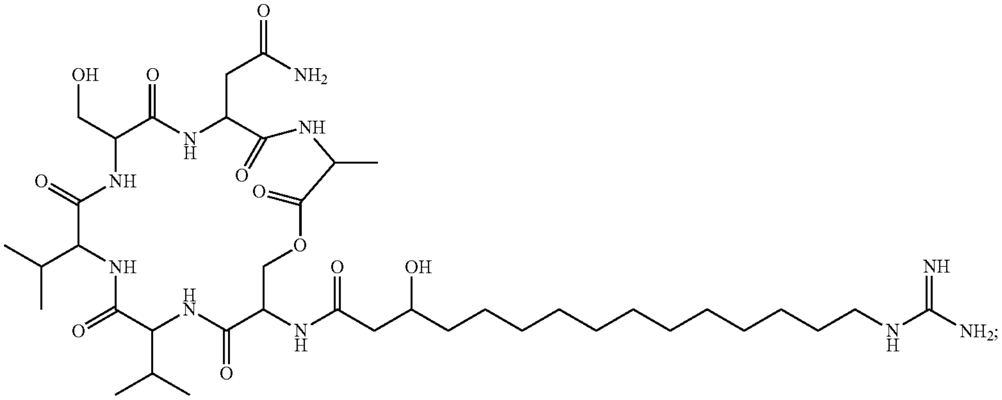

(IIj)

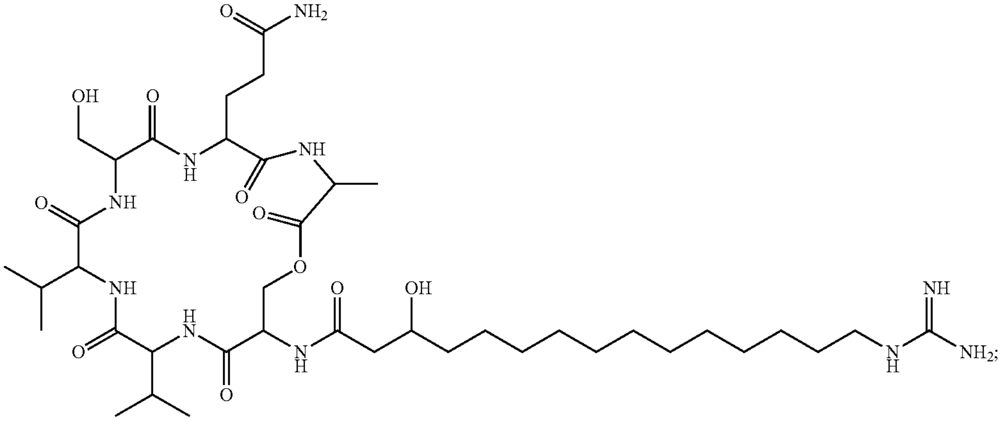

(IIk)

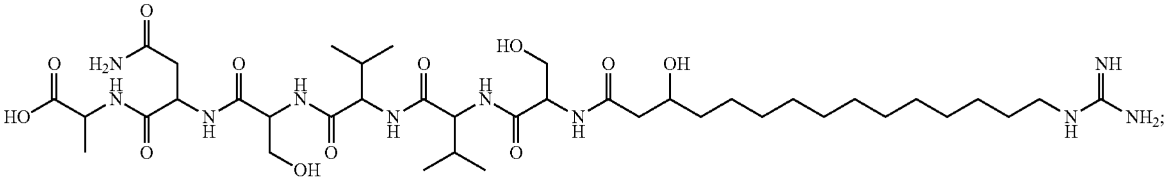

or (IIl)

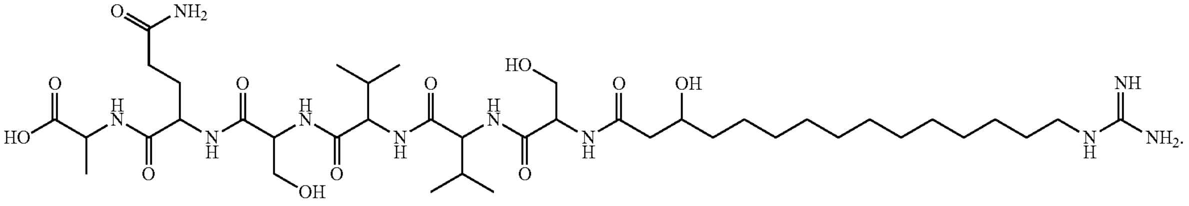

In other aspects, the present invention relates to a method of identifying a fungicidal *Paenibacillus* sp. strain and/or producing a corresponding fermentation product. The method comprises sequencing FusA-A3 in the *Paenibacillus* sp. strain to characterize a variant fusaricidin synthetase and assaying the fungicidal activity of the *Paenibacillus* sp. strain. In certain aspects, the FusA-A3 is sequenced using primers based on or more sequences shown in FIG. 13 (i.e., SEQ ID NOs: 1-11). In some embodiments, the screening is preceded by growing the cells and selecting the cells with one of more of the following characteristics: decreased or undetectable levels of fusaricidins with a tyrosine or a phenylalanine at amino acid residue (3) (e.g., LiF03a, LiF03b, LiF03c, LiF03d, LiF07a, LiF07b, LiF07c, and/or LiF07d) compared to fusaricidins quantified in a reference *Paenibacillus* sp. strain comprising a wild-type fusaricidin synthetase (i.e., expressing a functional FusA-A3); and/or increased levels of a Paeniserine (e.g., Paeniserine A1 and/or Paeniserine B1) and/or a Paeniprolixin compared to those quantified in a reference *Paenibacillus* sp. strain comprising a wild-type fusaricidin synthetase (i.e., expressing a functional FusA-A3).

In one aspect, the present invention encompasses a method for producing a fermentation product with broad spectrum antifungal activity, the method comprising culturing a *Paenibacillus* sp. strain with a variant fusaricidin synthetase to sporulation.

In another embodiment, the present invention relates to a method of identifying a fungicidal *Paenibacillus* sp. strain with broad spectrum antifungal activity, the method comprising: a) sequencing FusA-A3 in the *Paenibacillus* sp. strain to characterize a variant fusaricidin synthetase; b) assaying the fungicidal activity of the *Paenibacillus* sp. strain with the variant fusaricidin synthetase; and c) selecting the fungicidal *Paenibacillus* sp. strain as having broad spectrum antifungal activity if the *Paenibacillus* sp. strain comprises the variant fusaricidin synthetase and demonstrates increased fungicidal activity compared to a reference *Paenibacillus* sp. strain comprising a wild-type fusaricidin synthetase. The method may further comprise quantifying a Paeniserine and/or Paeniprolixin produced by the *Paenibacillus* sp. strain and selecting the *Paenibacillus* sp. strain as having broad spectrum antifungal activity if the *Paenibacillus* sp. strain produces increased levels of the Paeniserine and/or Paeniprolixin compared to the reference *Paenibacillus* sp. strain comprising a wild-type fusaricidin synthetase. In another aspect, the method further comprises culturing the fungicidal *Paenibacillus* sp. strain to produce a fungicidal fermentation product.

In one embodiment, the present invention is directed to a method of producing an antifungal fermentation comprising a fungicidal *Paenibacillus* sp. strain with broad spectrum antifungal activity, the method comprising: a) sequencing FusA-A3 in the *Paenibacillus* sp. strain to characterize a variant fusaricidin synthetase; b) assaying the fungicidal activity of the *Paenibacillus* sp. strain with the variant fusaricidin synthetase; c) selecting the fungicidal *Paenibacillus* sp. strain as having broad spectrum antifungal activity if the *Paenibacillus* sp. strain comprises the variant fusaricidin synthetase and demonstrates increased fungicidal activity compared to a reference *Paenibacillus* sp. strain comprising a wild-type fusaricidin synthetase; and d) culturing the fungicidal *Paenibacillus* sp. strain to produce a fungicidal fermentation product.

In some embodiments, the variant fusaricidin synthetase comprises a deletion of at least one, at least two, at least three, at least four, at least five, at least six, at least seven, at least eight, at least nine, or all ten of the amino acid residues that determine substrate specificity in FusA-A3. In other aspects, the variant fusaricidin synthetase comprises a deletion in FusA-A3 of at least one amino acid residue selected from the group consisting of Asp235, Ala236, Ser239, Thr278, Leu299, Ala301, Ala/Gly322, Val330, Cys331, Lys517, and combinations thereof.

The present invention also encompasses methods of treating a plant to control plant diseases by administering to a plant or a plant part, such as a leaf, stem, flowers, fruit, root, or seed or by applying to a locus on which plant or plant parts grow, such as soil, *Paenibacillus* sp. strain NRRL B-50972 or mutants thereof, or cell-free preparations thereof or metabolites thereof.

In a method according to the invention a composition containing *Paenibacillus* sp. strain NRRL B-50972 or a fungicidal mutant thereof can be applied to any plant or any part of any plant grown in any type of media used to grow plants (e.g., soil, vermiculite, shredded cardboard, and water) or applied to plants or the parts of plants grown aerially, such as orchids or staghorn ferns. The composition may for instance be applied by spraying, atomizing, vaporizing, scattering, dusting, watering, squirting, sprinkling, pouring or fumigating. As already indicated above, application may be carried out at any desired location where the plant of interest is positioned, such as agricultural, horticultural, forest, plantation, orchard, nursery, organically grown crops, turfgrass and urban environments.

Compositions of the present invention can be obtained by culturing *Paenibacillus* sp. strain NRRL B-50972 or a fungicidal mutant (strain) derived therefrom according to methods well known in the art, including by using the media and other methods described in the examples below. Conventional large-scale microbial culture processes include submerged fermentation, solid state fermentation, or liquid surface culture. Towards the end of fermentation, as nutrients are depleted, cells begin the transition from growth phase to sporulation phase, such that the final product of fermentation is largely spores, metabolites and residual fermentation medium. Sporulation is part of the natural life cycle of *Paenibacillus* and is generally initiated by the cell in response to nutrient limitation. Fermentation is configured to obtain high levels of colony forming units of and to promote sporulation. The bacterial cells, spores and metabolites in culture media resulting from fermentation may be used directly or concentrated by conventional industrial methods, such as centrifugation, tangential-flow filtration, depth filtration, and evaporation.

Compositions of the present invention include fermentation products. In some embodiments, the concentrated fermentation broth is washed, for example, via a diafiltration process, to remove residual fermentation broth and metabolites. The term “broth concentrate,” as used herein, refers to whole broth (fermentation broth) that has been concentrated by conventional industrial methods, as described above, but remains in liquid form. The term “fermentation solid,” as used herein, refers to the solid material that remains after the fermentation broth is dried. The term “fermentation product,” as used herein, refers to whole broth, broth concentrate and/or fermentation solids. Compositions of the present invention include fermentation products.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers, described below, may also be added post-drying.

Cell-free preparations of fermentation broth of the strains of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

In one embodiment, the fermentation product comprises at least about $1\times10^4$ colony forming units (CFU) of the microorganism (e.g., *Paenibacillus* sp. strain NRRL B-50972 or a fungicidal mutant strain thereof)/mL broth. In another embodiment, the fermentation product comprises at least about 1×10' colony forming units (CFU) of the microorganism (e.g., *Paenibacillus* sp. strain NRRL B-50972 or a fungicidal mutant strain thereof)/mL broth. In another embodiment, the fermentation product comprises at least about $1\times10^6$ CFU of the microorganism (e.g., *Paenibacillus* sp. strain NRRL B-50972 or a fungicidal mutant strain thereof)/mL broth. In yet another embodiment, the fermentation product comprises at least about $1\times10^7$ CFU of the microorganism (e.g., *Paenibacillus* sp. strain NRRL B-50972 or a fungicidal mutant strain thereof)/mL broth. In another embodiment, the fermentation product comprises at least about $1\times10^8$ CFU of the microorganism (e.g., *Paenibacillus* sp. strain NRRL B-50972 or a fungicidal mutant strain thereof)/mL broth. In another embodiment, the fermentation product comprises at least about $1\times10^9$ CFU of the microorganism (e.g., *Paenibacillus* sp. strain NRRL B-50972 or a fungicidal mutant strain thereof)/mL broth. In another embodiment, the fermentation product comprises at least about $1\times10^{10}$ CFU of the microorganism (e.g., *Paenibacillus* sp. strain NRRL B-50972 or a fungicidal mutant strain thereof)/mL broth. In another embodiment, the fermentation product comprises at least about $1\times10^{11}$ CFU of the microorganism (e.g., *Paenibacillus* sp. strain NRRL B-50972 or a fungicidal mutant strain thereof)/mL broth.

The inventive compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, oil dispersion, suspo-emulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

In some embodiments, the inventive compositions are liquid formulations. Non-limiting examples of liquid formulations include suspension concentrations and oil dispersions. In other embodiments, the inventive compositions are solid formulations. Non-limiting examples of liquid formulations include freeze-dried powders and spray-dried powders.

Compositions of the present invention may include formulation inerts added to compositions comprising cells, cell-free preparations or metabolites to improve efficacy, stability, and usability and/or to facilitate processing, packaging and end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, for example, Taylor, A. G., et al., "Concepts and Technologies of Selected Seed Treatments", Annu. Rev. Phytopathol. 28: 321-339 (1990). The stabilization agents may include anti-caking agents, anti-oxidation agents, desiccants, protectants or preservatives. The nutrients may include carbon, nitrogen, and phosphors sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, antifreeze agents or colorants. In some embodiments, the composition comprising cells, cell-free preparation or metabolites produced by fermentation can be used directly with or without water as the diluent without any other formulation preparation. In some embodiments, the formulation inerts are added after concentrating fermentation broth and during and/or after drying.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the fonn of varieties, races, biotypes and genotypes.

The treatment of the plants and plant parts with the compositions according to the invention is carried out directly or by acting on the environment, habitat or storage space using customary treatment methods, for example by dipping, spraying, atomizing, misting, evaporating, dusting, fogging, scattering, foaming, painting on, spreading, injecting, drenching, trickle irrigation and, in the case of propagation material, in particular in the case of seed, furthermore by the dry seed treatment method, the wet seed treatment method, the slurry treatment method, by encrusting, by coating with one or more coats and the like. It is furthermore possible to apply the active substances by the ultra-low volume method or to inject the active substance preparation or the active substance itself into the soil.

A preferred direct treatment of the plants is the leaf application treatment, i.e., compositions according to the invention are applied to the foliage, it being possible for the treatment frequency and the application rate to be matched to the infection pressure of the pathogen in question.

In the case of systemically active compounds, the compositions according to the invention reach the plants via the root system. In this case, the treatment of the plants is effected by allowing the compositions according to the invention to act on the environment of the plant. This can be done for example by drenching, incorporating in the soil or into the nutrient solution, i.e., the location of the plant (for example the soil or hydroponic systems) is impregnated with a liquid form of the compositions according to the invention, or by soil application, i.e., the compositions according to the invention are incorporated into the location of the plants in solid form (for example in the forn of granules). In the case of paddy rice cultures, this may also be done by metering the compositions according to the invention into a flooded paddy field in a solid use form (for example in the form of granules).

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term "useful plants" as used in the present context refers to crop plants which are employed as plants for obtaining foodstuffs, feedstuffs, fuels or for industrial purposes.

The useful plants which can be treated and/or improved with the compositions and methods of the present invention include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; *Lauraceae*, for example avocado, *Cinnamomum*, camphor, or else plants such as tobacco, nuts, coffee, aubergine, sugar cane, tea, pepper, grapevines, hops, bananas, latex plants and ornamentals, for example flowers, shrubs, deciduous trees and coniferous trees. This enumeration is no limitation.

The following plants are considered to be particularly suitable target crops for applying compositions and methods of the present invention: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., Acer sp., *Tsuga* sp., *Fraxinus* sp., *Sorbus* sp., *Betula* sp., *Crataegus* sp., *Ulmus* sp., *Quercus* sp., *Fagus* sp., Salix sp., *Populus* sp.

Preferred trees which can be improved in accordance with the method according to the invention are: from the tree species *Aesculus: A. hippocastanum, A. pariflora, A. carnea*; from the tree species *Platanus: P. acerilora, P. occidentalis, P. raceniosa*; from the tree species *Picea: P. abies*; from the tree species *Pinus: P. radiata, P. ponderosa, P. contorta, P. sylvestre, P. elliottii, P. montecola, P. albicaulis, P. resinosa, P. palustris, P. taeda, P. flexilis, P. jeffregi, P. baksiana, P. strobus*; from the tree species *Eucalyptus: E. grandis, E. globulus, E. camadentis, E. nitens, E. obliqua, E. regnans, E. pilularus.*

Especially preferred trees which can be improved in accordance with the method according to the invention are: from the tree species *Pinus: P. radiata, P. ponderosa, P. contorta, P. sylvestre, P. strobus*; from the tree species *Eucalyptus: E. grandis, E. globulus, E. camadentis.*

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha Gaudin*), wood bluegrass (*Poa nemoralis* L.) and bulbous bluegrass (*Poa bulbosa* L.); bentgrasses (*Agrostis* spp.) such as creeping bentgrass (Agrostispalustris Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.);

- fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (Festucu capillata Lam.), tall fescue (*Festuca arundinacea* Schreb.) and meadow fescue (*Festuca* elanor L.);
- ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);
- and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.)

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.)

Examples of warm-season turf grasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpetgrass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), blue grama (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turf grasses are generally preferred for the use according to the invention. Especially preferred are bluegrass, benchgrass and redtop, fescues and ryegrasses. Bentgrass is especially preferred.

The inventive compositions have potent microbicidal activity and can be used for control of unwanted microorganisms, such as fungi and bacteria, in crop protection and in the protection of materials.

The invention also relates to a method for controlling unwanted microorganisms, characterized in that the inventive compositions are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi *imperfecti*). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

- diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;*
- diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia recondite, P. triticina, P. graminis* or *P. striifornis; Uromyces* species, for example *Uromyces appendiculatus;*
- diseases caused by pathogens from the group of the Oomycetes, for example *Albugo* species, for example *Algubo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;*
- leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidia form: *Drechslera*, Syn: *Helminthosporium*), *Cochliobolus miyabeanus; Colletotrichum* species, for example *Colletotrichum lindemuthanium; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans, Leptosphaeria nodorum; Magnaporthe* species, for example *Magnaporthe grisea; Marssonia* species, for example *Marssonia coronaria; Microdochium* species, for example *Microdochium nivale; Mycosphaerella* species, for example *Mycosphaerella graminicola, M. arachidicola* and *M. fijiensis; Phaeosphaeria* species, for example *Phaeosphaeria nodorum; Pyrenophora* species, for example *Pyrenophora teres, Pyrenophora tritici* repentis; *Ramularia* species, for example *Ramularia collo-cygni, Ramularia areola; Rhynchosporium* species, for example *Rhynchosporium secalis; Septoria* species, for example *Septoria apii, Septoria lycopersii; Typhula* species, for example *Typhula incarnata; Venturia* species, for example *Venturia inaequalis;*
- root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, such as, for example *Rhizoctonia solani; Sarocladium* diseases caused for example by *Sarocladium oryzae; Sclerotium* diseases caused for example by *Sclerotium oryzae; Tapesia* species, for example *Tapesia acuformis; Thielaviopsis* species, for example *Thielaviopsis basicola;*
- ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum;*
- diseases caused by smut fungi, for example *Sphacelotheca* species, for example *Sphacelotheca reiliana; Tilletia* species, for example *Tilletia* caries, *T. controversa; Urocystis* species, for example *Urocystis occulta; Ustilago* species, for example *Ustilago nuda, U. nuda tritici;*
- fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum; Verticilium* species, for example *Verticilium alboatrum;*
- seed and soilborne decay, mould, wilt, rot and damping-off diseases caused, for example, by *Alternaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (Conidiaforn: *Drechslera, Bipolaris* Syn: *Helminthosporium*); *Colletotrichun* species, caused for example by *Colletotrichum coccodes; Fusarium species, caused for example by Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma lingam; Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia*

*oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii; Septoria* species, caused for example by *Septoria nodorum; Typhula* species, caused for example by *Typhula incarnata; Verticillium* species, caused for example by *Verticillium dahliae;* cancers, galls and witches' broom caused, for example, by *Nectria* species, for example *Nectria galligena;* wilt diseases caused, for example, by *Monilinia* species, for example *Monilinia laxa;* leaf blister or leaf curl diseases caused, for example, by *Exobasidium* species, for example *Exobasidium vexans;*

*Taphrina* species, for example *Taphrina deformans;* decline diseases of wooden plants caused, for example, by Esca disease, caused for example by *Phaemoniella clamydospora, Phaeoacremonium aleophilum* and *Fomitiporia mediterranea; Eutypa* dyeback, caused for example by *Eutypa lata; Ganoderma* diseases caused for example by *Ganoderma* boninense; *Rigidoporus* diseases caused for example by *Rigidoporus lignosus;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;*

Club root caused, for example, by *Plasmodiophora* species, for example *Plamodiophora brassicae;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora.*

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), phyllostica leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), *rhizoctonia* aerial, foliage, and web blight (*Rhizoctonia solani*), rust (*Phakopsora pachyrhizi, Phakopsora meibomiae*), scab (*Sphaceloma glycines*), *stemphylium* leaf blight (*Stemphylium botryosum*), target spot (*Corynespora cassiicola*).

Fungal diseases on roots and the stem base caused, for example, by black root rot (Calonectria *crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. caulivora), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* southern blight (*Sclerotinia rolfsii*), *thielaviopsis* root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive compositions, which are applied to the seed, the plant or plant parts, the fruit or the soil in which the plants grow.

The fact that the compositions are well tolerated by plants at the concentrations required for controlling plant diseases allows the treatment of above-ground parts of plants, of propagation stock and seeds, and of the soil.

According to the invention all plants and plant parts can be treated including cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods.

In certain aspects, the compositions of the present invention are applied at about $1\times10^8$ to about $1\times10^{14}$ colony forming units (CFU) of fungicidal *Paenibacillus* sp. strain NRRL B-50972 or fungicidal mutant strain thereof per hectare. In other aspects, the compositions of the present invention are applied at about $1\times10^9$ to about $1\times10^{13}$ colony forming units (CFU) of fungicidal *Paenibacillus* sp. strain NRRL B-50972 or fungicidal mutant strain thereof per hectare. In yet other aspects, the compositions of the present invention are applied at about $1\times10^{10}$ to about $1\times10^{12}$ colony forming units (CFU) of fungicidal *Paenibacillus* sp. strain NRRL B-50972 or fungicidal mutant strain thereof per hectare.

In some embodiments, the compositions of the present invention are applied at about 0.1 kg to about 10 kg fermentation solids per hectare. In other embodiments, the compositions of the present invention are applied at about 0.25 kg to about 7.5 kg fermentation solids per hectare. In yet other embodiments, the compositions of the present invention are applied at about 0.5 kg to about 5 kg fermentation solids per hectare. The compositions of the present invention may also be applied at about 1 kg or about 2 kg fermentation solids per hectare.

The inventive compositions, when they are well tolerated by plants, have favorable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g., canola, rapeseed), *Brassica rapa, B. juncea* (e.g., (field) mustard) and *Brassica carinata*, Arecaceae sp. (e.g., oilpalm, coconut), rice, wheat, sugar beet, sugar cane, oats, rye, barley, millet and sorghum, triticale, flax, nuts, grapes and vine and various fruit and vegetables from various botanic taxa, e.g., Rosaceae sp. (e.g., pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g., avocado, cinnamon, camphor), *Musaceae* sp. (e.g., banana trees and plantations), *Rubiaceae* sp. (e.g., coffee), *Theaceae* sp. (e.g., tea), *Sterculiceae* sp., *Rutaceae* sp. (e.g., lemons, oranges, mandarins and grapefruit); *Solanaceae* sp. (e.g., tomatoes, potatoes, peppers, *capsicum*, aubergines, tobacco), *Liliaceae* sp., *Compositae* sp. (e.g., lettuce, artichokes and chicory—including root chicory, endive or common chicory), *Umbelliferae* sp. (e.g., carrots, parsley, celery and celeriac), *Cucurbitaceae* sp. (e.g., cucumbers—including gherkins, pumpkins, watermelons, calabashes and melons), *Alliaceae* sp. (e.g., leeks and onions), *Cruciferae* sp. (e.g., white cabbage, red cabbage, broccoli, cauliflower, Brussels sprouts, pak choi, kohlrabi, radishes, horseradish, cress and chinese cabbage), *Leguminosae* sp. (e.g., peanuts, peas, lentils and beans—e.g., common beans and broad beans), *Chenopodiaceae* sp. (e.g. Swiss chard, fodder beet, spinach, beetroot), *Linaceae* sp. (e.g., hemp), *Cannabeacea* sp. (e.g., *cannabis*), *Malvaceae* sp. (e.g., okra, cocoa), Papaveraceae (e.g., poppy), Asparagaceae (e.g., asparagus); useful plants and ornamental plants in the garden and woods including turf, lawn, grass and *Stevia rebaudiana*; and in each case genetically modified types of these plants.

In certain aspects, the fermentation product further comprises a formulation ingredient. The formulation ingredient may be a wetting agent, extender, solvent, spontaneity promoter, emulsifier, dispersant, frost protectant, thickener, and/or an adjuvant. In one embodiment, the formulation ingredient is a wetting agent. In other aspects, the fermentation product is a freeze-dried powder or a spray-dried powder.

Compositions of the present invention may include formulation ingredients added to compositions of the present invention to improve recovery, efficacy, or physical properties and/or to aid in processing, packaging and administration. Such formulation ingredients may be added individually or in combination.

The formulation ingredients may be added to compositions comprising cells, cell-free preparations, isolated compounds, and/or metabolites to improve efficacy, stability, and physical properties, usability and/or to facilitate processing, packaging and end-use application. Such formulation ingredients may include agriculturally acceptable carriers, inerts, stabilization agents, preservatives, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the formulation ingredient is a binder, adjuvant, or adhesive that facilitates adherence of the composition to a plant part, such as leaves, seeds, or roots. See, for example, Taylor, A. G., et al., "Concepts and Technologies of Selected Seed Treatments," Annu. Rev. Phytopathol., 28: 321-339 (1990). The stabilization agents may include anti-caking agents, anti-oxidation agents, anti-settling agents, antifoaming agents, desiccants, protectants or preservatives. The nutrients may include carbon, nitrogen, and phosphorus sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, film-formers, hydrotropes, builders, antifreeze agents or colorants. In some embodiments, the composition comprising cells, cell-free preparation and/or metabolites produced by fermentation can be used directly with or without water as the diluent without any other formulation preparation. In a particular embodiment, a wetting agent, or a dispersant, is added to a fermentation solid, such as a freeze-dried or spray-dried powder. A wetting agent increases the spreading and penetrating properties, or a dispersant increases the dispersibility and solubility of the active ingredient (once diluted) when it is applied to surfaces. Exemplary wetting agents are known to those of skill in the art and include sulfosuccinates and derivatives, such as MULTIWET™ MO-70R (Croda Inc., Edison, NJ); siloxanes such as BREAK-THRU® (Evonik, Germany); nonionic compounds, such as ATLOX™ 4894 (Croda Inc., Edison, NJ); alkyl polyglucosides, such as TERWET® 3001 (Huntsman International LLC, The Woodlands, Texas); C12-C14 alcohol ethoxylate, such as TERGITOL® 15-S-15 (The Dow Chemical Company, Midland, Michigan); phosphate esters, such as RHODAFAC® BG-510 (Rhodia, Inc.); and alkyl ether carboxylates, such as EMULSOGEN™ LS (Clariant Corporation, North Carolina).

DEPOSIT INFORMATION

A sample of a *Paenibacillus* sp. strain of the invention has been deposited with the Agricultural Research Service Culture Collection located at the National Center for Agricultural Utilization Research, Agricultural Research Service, U.S. Department of Agriculture (NRRL), 1815 North University Street, Peoria, IL 61604, U.S.A., under the Budapest Treaty on Aug. 28, 2014, and has been assigned the following accession number: NRRL B-50972.

A sample of the *Paenibacillus* sp. strain derived from *Paenibacillus* sp. strain NRRL B-50972 that demonstrates a stable colony morphology has been deposited with the Agricultural Research Service Culture Collection located at the National Center for Agricultural Utilization Research, Agricultural Research Service, U.S. Department of Agriculture (NRRL), 1815 North University Street, Peoria, IL 61604, U.S.A., under the Budapest Treaty on Sep. 1, 2015 and has been assigned the following accession number: NRRL B-67129.

The *Paenibacillus* sp. strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. However, it should be understood that the availability of a deposit does not constitute a license to practice the subject invention in derogation of patent rights granted by governmental action.

The following examples are given for purely illustrative and non-limiting purposes of the present invention.

EXAMPLES

Example 1. Selection of *Paenibacillus* sp. NRRL B-50972

The genomes of several *Paenibacillus* sp. strains were sequenced. The genomic data was analyzed to identify strains with the fusaricidin biosynthesis gene cluster but lacking the polymyxin synthetase gene cluster. The gene cluster responsible for fusaricidin biosynthesis (fusA) had been identified and characterized previously as had the polymyxin synthetase gene cluster. See, e.g., Li et al., "Nonribosomal Biosynthesis of Fusaricidins by *Paenibacillus polymyxa* PKB1 Involves Direct Activation of a D-Amino Acid," Chemistry & Biology, 15:118-127 (2008); Li et al., "Promoter Analysis and Transcription Regulation of fus Gene Cluster Responsible for Fusaricidin Synthesis of *Paenibacillus polymyxa* SQR-21," Applied Microbiol Biotechnol, 97:9479-9489 (2013); and Choi et al., "Identification of a Polymyxin Synthetase Gene Cluster of *Paenibacillus polymyxa* and Heterologous Expression of the Gene in *Bacillus subtilis*," Journal of Bacteriology, 191(10):3350-3358 (2009).

The strains identified with this analysis were further evaluated to confirm fusaricidin production. Briefly, each strain was cultured in a soy-based medium and the lipophilic fraction of the whole broth was extracted. The whole broth extract was analyzed via high-performance liquid chromatography (HPLC) and the presence of fusaricidin A was identified based on the HPLC profile generated with a standard sample containing fusaricidin A.

Example 2. In Planta Antifungal Activity of *Paenibacillus* sp. Strains Whole Broths Selected *Paenibacillus* sp. strains including *Paenibacillus* sp. strain NRRL B-50972 were grown in a soy-based medium to produce whole broth cultures. Distilled water was added to each of the whole broths to make a final dilution of 10%.

The diluted whole broths were applied to the leaves of young plants that were subsequently exposed to a fungal inoculum of Tomato Late Blight (PHYTIN), Grey Mould (BOTRCI), or Wheat Leaf Rust (PUCCRT). An untreated control was included for purposes of comparison in each assay. Several days after exposure to the fungal inoculums, each plant was scored for percent control of the pathogen relative to the untreated control plants. Each treatment was evaluated with three replicates and the average percent control with each *Paenibacillus* sp. strain's whole broth shown in FIG. 1.

Of the 23 strains tested for antifungal activity against PHYTIN, BOTRCI, and PUCCRT *Paenibacillus* sp. strain NRRL B-50972 was one of the few strains that had a relatively high level of activity against all three fungal pathogens.

Example 3. In Vitro Biological Efficacy of *Paenibacillus* sp. Strain NRRL B-50972 Fusaricidin Extract Whole broth cultures of several *Paenibacillus* sp. strains, including *Paenibacillus* sp. NRRL B-50972, were prepared using a soy-based medium. Lipophilic fractions containing fusaricidins were extracted from the whole broths. Three separate fractions containing various fusaricidins and antifungal metabolites were made from the extract of the whole broth from the first *Paenibacillus* sp. strain (i.e., Fraction 1, Fraction 2, and Fraction 3). The extract from the *Paenibacillus* sp. strain NRRL B-50972 was not separated further.

The fusaricidin-containing fractions from each strain were tested against the following twelve fungal pathogens: *Alternaria alternata* (ALTEAL), *Botrytis cinerea* (BOTRCI), *Fusarium culmorum* (FUSACU), *Phaeosphaeria nodorum* (LEPTNO), *Zymoseptoria tritici* (SEPPTR), *Phytophthora cryptogea* (PHYTCR), *Phytophthora infestans* (PHYTIN), *Pythium ultimum* (PYTHUL), *Magnaporthe oryzae* (PYRIOR), *Thanatephorus cucumeris* (RHIZSO), *Ustilago segetum* var. *avenae* (USTIAV), and *Uromyces appendiculatus* (UROMAP). Inhibition of fungal cell growth by the different fractions was evaluated in a soy-based medium and compared to the growth of untreated controls. Eight doses of each fraction were tested ranging from 0.005 ppm to 100 ppm. The effective doses producing 50% inhibition ($ED_{50}$) and 80% inhibition ($ED_{80}$) are reported in the table in FIG. 2.

The *Paenibacillus* sp. strain NRRL B-50972 fusaricidin-containing fraction exhibited a broad spectrum of antifungal activity across the twelve assays that was not observed with the fractions from the other *Paenibacillus* sp. strain. The *Paenibacillus* sp. strain NRRL B-50972 fraction also demonstrated much greater activity in the assays than that observed with the fractions from the other *Paenibacillus* sp. strain (see FIG. 2).

Example 4. In Vivo Preventive Test on Tomatoes Infected with *Phytophthora*

In this plant pathogen greenhouse assay the fermentation product of *Paenibacillus* sp. strain NRRL B-50972 was tested in comparison to three other *Paenibacillus* sp. strains that had demonstrated relatively high antifungal activity in previous screening assays. To produce a suitable preparation of the compounds, 1 part by weight of the spray dried powder of whole broth from each strain cultured in a soy-based medium was mixed with water and 0.1 part by weight of emulsifier (alkylaryl polyglycol ether) and subsequently diluted with water to the desired concentration.

To test for preventive activity, young plants were sprayed with the compound preparation at the stated rate of application. After the spray coating dried on, the plants were inoculated with an aqueous spore suspension of *Phytophthora infestans*. The plants were then placed in an incubation cabinet at approximately 20° C. and a relative atmospheric humidity of 100%.

The test was evaluated 3 days after the inoculation. 0% means an efficacy which corresponds to that of the untreated control, while an efficacy of 100% means that no disease is observed.

TABLE 2

In Vivo Preventive Test on *Phytophthora* (Tomatoes)

| Compound | Rate of Application of Whole Broth in ppm | Efficacy in % |
|---|---|---|
| *Paenibacillus* sp. NRRL B-50972 | 10,000 | 70 |
| *Paenibacillus* sp. Strain X | 10,000 | 63 |
| *Paenibacillus* sp. Strain Y | 10,000 | 70 |
| *Paenibacillus* sp. Strain Z | 10,000 | 68 |

Example 5. In Vivo Preventive Test on Grapevines Infected with Plasmopara

In this plant pathogen greenhouse assay the fermentation product of *Paenibacillus* sp. strain NRRL B-50972 was tested in comparison to three other *Paenibacillus* sp. strains that had demonstrated relatively high antifungal activity in previous screening assays. To produce a suitable preparation of the compounds, 1 part by weight of the spray dried powder prepared as described in Example 5 was mixed with water and 0.1 part by weight of emulsifier (alkylaryl polyglycol ether) and subsequently diluted with water to the desired concentration.

To test for preventive activity, young plants were sprayed with the compound preparation at the stated rate of application. After the spray coating dried on, the plants were inoculated with an aqueous spore suspension of *Plasmopara viticola* and then remained for 1 day in an incubation cabinet at approximately 20° C. and a relative atmospheric humidity of 100%. The plants were subsequently placed for 4 days in a greenhouse at approximately 21° C. and a relative atmospheric humidity of approximately 90%. The plants were then misted and placed for 1 day in an incubation cabinet.

The test was evaluated 6 days after the inoculation. 0% means an efficacy which corresponds to that of the untreated control, while an efficacy of 100% means that no disease is observed.

TABLE 3

In Vivo Preventive Test on *Plasmopara* (Grapevines)

| Compound | Rate of Application of Whole Broth in ppm | Efficacy in % |
|---|---|---|
| *Paenibacillus* sp. NRRL B-50972 | 10,000 | 93 |
| *Paenibacillus* sp. Strain X | 10,000 | 46 |
| *Paenibacillus* sp. Strain Y | 10,000 | 62 |
| *Paenibacillus* sp. Strain Z | 10,000 | 78 |

Example 6. In Vivo Preventive Test on Beans Infected with *Uromyces*

In this plant pathogen greenhouse assay the fermentation product of *Paenibacillus* sp. strain NRRL B-50972 was tested in comparison to three other *Paenibacillus* sp. strains that had demonstrated relatively high antifungal activity in previous screening assays. To produce a suitable preparation of the compounds, 1 part by weight of the spray dried powder prepared as described in Example 5 was mixed with water and 0.1 part by weight of emulsifier (alkylaryl polyglycol ether) and subsequently diluted with water to the desired concentration.

To test for preventive activity, young plants were sprayed with the compound preparation at the stated rate of application. After the spray coating dried on, the plants were inoculated with an aqueous spore suspension of the causal agent of bean rust (*Uromyces appendiculatus*) and then remained for 1 day in an incubation cabinet at approximately 20° C. and a relative atmospheric humidity of 100%.

The plants were then placed in a greenhouse at approximately 21° C. and a relative atmospheric humidity of approximately 90%.

The test was evaluated 10 days after the inoculation. 0% means an efficacy which corresponds to that of the untreated control, while an efficacy of 100% means that no disease is observed.

TABLE 4

In Vivo Preventive Test on *Uromyces* (Beans)

| Compound | Rate of Application of Whole Broth in ppm | Efficacy in % |
|---|---|---|
| *Paenibacillus* sp. NRRL B-50972 | 10,000 | 85 |
| *Paenibacillus* sp. Strain X | 10,000 | 50 |
| *Paenibacillus* sp. Strain Y | 10,000 | 40 |
| *Paenibacillus* sp. Strain Z | 10,000 | 40 |

Example 7. Comparison of *Paenibacillus* Strains in a Zucchini Field Trial Infected with Powdery Mildew (*Sphaerotheca fuliginea*)

Two field trials with zucchini, artificially inoculated with *Sphaerotheca fuliginea*, were conducted. Five treatments with spray dried powder of whole broth from each *Paenibacillus* sp. strain cultured in a soy-based medium were resuspended in water in an application volume of 1000 L/ha and applied to plants between July 15 and August 8 at a growth stage of BBCH59 to BBCH72 in 4 to 8 days interval as outlined in Table 6. The percent disease control shown in Table 5 is the result of the last evaluation made 10 days after the final application, done by visual observation of disease symptoms. 0% means an efficacy which corresponds to that of the untreated control while an efficacy of 100% means that no disease was observed.

TABLE 5

| Product | Dosage kg/ha | Application Code | Disease Control in % Mean of 2 Trials |
|---|---|---|---|
| Untreated Control | | | 0 |
| *Paenibacillus* sp. NRRL B-50972 | 4 | ABCDE | 100 |
| *Paenibacillus* sp. NRRL B-50972 | 2 | ABCDE | 92 |
| *Paenibacillus* sp. Strain X | 4 | ABCDE | 59 |
| *Paenibacillus* sp. Strain X | 2 | ABCDE | 29 |
| *Paenibacillus* sp. Strain Y | 4 | ABCDE | 66 |
| *Paenibacillus* sp. Strain Y | 2 | ABCDE | 46 |
| *Paenibacillus* sp. Strain Z | 4 | ABCDE | 29 |
| *Paenibacillus* sp. Strain Z | 2 | ABCDE | 18 |

TABLE 6

| Application Code | Application Date | Growth Stage |
|---|---|---|
| A | July 15 | 59 |
| B | July 23 | 65 |
| C | July 30 | 71 |
| D | August 4 | 72 |
| E | August 8 | 72 |

The results in Table 4 clearly show that the observed activity of *Paenibacillus* sp. strain NRRL B-50972 is superior compared to the other strains tested in this field trial, which had demonstrated relatively high antifungal activity in previous screening assays.

Example 8. Comparison of *Paenibacillus* Strains in a Grapevine Field Trial Infected with Powdery Mildew (*Uncinula Necator*)

Two field trials with grapevine, naturally infected with *Uncinula necator*, were conducted. Six treatments with the spray dried powders described in Example 8 were resuspended in water in an application volume of 1000 L/ha and applied to plants between June 3 and July 1 at a growth stage of BBCH57 to BBCH75 in 5 to 7 days interval as outlined in Table 8. The percent disease control shown in Table 7 is the result of the last evaluation made 15 days after the final application, done by visual observation of disease symptoms. 0% means an efficacy which corresponds to that of the untreated control while an efficacy of 100% means that no disease was observed.

TABLE 7

| Product | Dosage kg/ha | Application Code | Disease Control in % Mean of 2 Trials |
|---|---|---|---|
| Untreated Control | | | 0 |
| *Paenibacillus* sp. NRRLB-50972 | 4 | ABCDEF | 100 |
| *Paenibacillus* sp. NRRLB-50972 | 2 | ABCDEF | 100 |
| *Paenibacillus* sp. Strain X | 4 | ABCDEF | 45 |
| *Paenibacillus* sp. Strain X | 2 | ABCDEF | 28 |
| *Paenibacillus* sp. Strain Y | 4 | ABCDEF | 66 |
| *Paenibacillus* sp. Strain Y | 2 | ABCDEF | 60 |
| *Paenibacillus* sp. Strain Z | 4 | ABCDEF | 36 |
| *Paenibacillus* sp. Strain Z | 2 | ABCDEF | 25 |

TABLE 8

| Application Code | Application Date | Growth Stage |
|---|---|---|
| A | June 3 | 57 |
| B | June 10 | 60 |
| C | June 16 | 64 |
| D | June 21 | 71 |
| E | June 26 | 73 |
| F | July 1 | 75 |

The results in Table 7 clearly show that the observed activity of *Paenibacillus* sp. strain NRRL B-50972 is superior compared to the other strains tested in this field trial, which had demonstrated relatively high antifungal activity in previous screening assays.

Example 9. Comparison of *Paenibacillus* Strains in a Tomato Field Trial Infected with Early Blight (*Alternaria Solani*)

Two field trials with tomato plants, artificially inoculated with *Alternaria solani*, were conducted. Three treatments with the spray dried powders described in Example 8 were resuspended in water in an application volume of 1000 L/ha and applied to plants between June 26 and July 10 at a growth stage of BBCH51 to BBCH59 in 6 to 8 days interval as outlined in Table 10. The percent disease control shown in Table 9 is the result of the last evaluation made 8 days after the final application, done by visual observation of disease symptoms. 0% means an efficacy which corresponds to that of the untreated control while an efficacy of 100% means that no disease was observed.

TABLE 9

| Product | Dosage kg/ha | Application Code | Disease Control in % Mean of 2 Trials |
|---|---|---|---|
| Untreated Control | | | 0 |
| *Paenibacillus* sp. NRRL B-50972 | 4 | ABC | 84 |
| *Paenibacillus* sp. NRRL B-50972 | 2 | ABC | 68 |
| *Paenibacillus* sp. Strain X | 4 | ABC | 36 |
| *Paenibacillus* sp. Strain X | 2 | ABC | 20 |
| *Paenibacillus* sp. Strain Y | 4 | ABC | 44 |
| *Paenibacillus* sp. Strain Y | 2 | ABC | 19 |
| *Paenibacillus* sp. Strain Z | 4 | ABC | 40 |
| *Paenibacillus* sp. Strain Z | 2 | ABC | 11 |

TABLE 10

| Application Code | Application Date | Growth Stage |
|---|---|---|
| A | Jun. 26 | 51 |
| B | Jul. 2 | 53 |
| C | Jul. 10 | 59 |

The results in Table 9 clearly show that the observed activity of *Paenibacillus* sp. strain NRRL B-50972 is superior compared to the other strains tested in this field trial, which had demonstrated relatively high antifungal activity in previous screening assays.

Example 10. Comparison of *Paenibacillus* Strains in a Potato Field Trial Infected with Early Blight (*Alternaria solani*)

A field trial with potato plants, artificially inoculated with *Alternaria solani*, was conducted. Five treatments with the spray dried powders described in Example 8 were resuspended in water in an application volume of 500 L/ha and applied to plants between June 26 and July 19 at a growth stage of BBCH37 to BBCH55 in 4 to 8 days interval as outlined in Table 12. The percent disease control shown in Table 11 is the result of the last evaluation made 6 days after the final application, done by visual observation of disease symptoms. 0% means an efficacy which corresponds to that of the untreated control while an efficacy of 100% means that no disease was observed.

TABLE 11

| Product | Dosage kg/ha | Application Code | Disease Control in % |
|---|---|---|---|
| Untreated Control | | | 0 |
| *Paenibacillus* sp. NRRL B-50972 | 4 | ABCDE | 80 |
| *Paenibacillus* sp. NRRL B-50972 | 2 | ABCDE | 71 |
| *Paenibacillus* sp. Strain X | 4 | ABCDE | 71 |
| *Paenibacillus* sp. Strain X | 2 | ABCDE | 41 |
| *Paenibacillus* sp. Strain Y | 4 | ABCDE | 61 |
| *Paenibacillus* sp. Strain Y | 2 | ABCDE | 41 |
| *Paenibacillus* sp. Strain Z | 4 | ABCDE | 41 |
| *Paenibacillus* sp. Strain Z | 2 | ABCDE | 32 |

TABLE 12

| Application Code | Application Date | Growth Stage |
|---|---|---|
| A | Jun. 26 | 37 |
| B | Jul. 2 | 47 |
| C | Jul. 10 | 51 |
| D | Jul. 15 | 55 |
| E | Jul. 19 | 55 |

The results in Table 11 clearly show that the observed activity of *Paenibacillus* sp. strain NRRL B-50972 is superior compared to the other strains tested in this field trial, which had demonstrated relatively high antifungal activity in previous screening assays.

Example 11. Comparison of *Paenibacillus* Strains in a Potato Field Trial Infected with Early Blight (*Alternaria solani*)

A field trial with potato plants, artificially inoculated with *Alternaria solani*, was conducted. Three treatments with the spray dried powders described in Example 8 were resuspended in water in an application volume of 500 L/ha and applied to plants between July 24 and August 5 at a growth stage of BBCH37 to BBCH51 in 6 days interval as outlined in Table 14. The percent disease control shown in Table 13 is the result of the last evaluation made 6 days after the final application, done by visual observation of disease symptoms. 0% means an efficacy which corresponds to that of the untreated control while an efficacy of 100% means that no disease was observed.

TABLE 13

| Product | Dosage kg/ha | Application Code | Disease Control in % |
|---|---|---|---|
| Untreated Control | | | 0 |
| *Paenibacillus* sp. NRRL B-50972 | 4 | ABC | 100 |
| *Paenibacillus* sp. NRRL B-50972 | 2 | ABC | 100 |
| *Paenibacillus* sp. Strain X | 4 | ABC | 74 |
| *Paenibacillus* sp. Strain X | 2 | ABC | 48 |
| *Paenibacillus* sp. Strain Y | 4 | ABC | 74 |
| *Paenibacillus* sp. Strain Y | 2 | ABC | 61 |
| *Paenibacillus* sp. Strain Z | 4 | ABC | 74 |
| *Paenibacillus* sp. Strain Z | 2 | ABC | 61 |

TABLE 14

| Application Code | Application Date | Growth Stage |
|---|---|---|
| A | Jul. 24 | 37 |
| B | Jul. 30 | 40 |
| C | Aug. 5 | 51 |

The results in Table 13 clearly show that the observed activity of *Paenibacillus* sp. strain NRRL B-50972 is superior compared to the other strains tested in this field trial, which had demonstrated relatively high antifungal activity in previous screening assays.

Example 12. Identification of fusA Variation in *Paenibacillus* sp. Strain NRRL B-50972

To further characterize *Paenibacillus* sp. strain NRRL B-50972 the genomic sequence of the fusA gene encoding the FusA fusaricidin synthetase was determined with standard sequencing methods, and the related amino acid sequence was identified. The amino acid sequence from FusA expressed by *Paenibacillus* sp. strain NRRL B-50972 was compared to that of several other *Paenibacillus* strains including those described in the following publications:

Li S., et al., (2014). "Complete Genome Sequence of *Paenibacillus polymyxa* SQR-21, a Plant Growth-Promoting Rhizobacterium with Antifungal Activity and Rhizosphere Colonization Ability," *Genome Announc,* 2(2):HASH(0x743db288);

Niu B., et al., (2011). "The Genome of the Plant Growth-Promoting Rhizobacterium *Paenibacillus polymyxa* M-1 Contains Nine Sites Dedicated to Nonribosomal Synthesis of Lipopeptides and Polyketides," *J. Bacteriol.* 193(20):5862-3;

Ma M., et al., (2011) "Complete Genome Sequence of *Paenibacillus polymyxa* SC2, A Strain of Plant Growth-Promoting Rhizobacterium with Broad-Spectrum Antimicrobial Activity," *J. Bacteriol.* 193(1):311-2; and Li and Jensen, (2008). Nonribosomal Biosynthesis of Fusaricidins by *Paenibacillus polymyxa* PKB1 Involves Direct Activation of a d-amino Acid. Chem. Biol. 15, 118-127.

The alignment shown in FIG. 13 revealed significant deletions in the variant FusA fusaricidin synthetase expressed by *Paenibacillus* sp. NRRL B-50972. A first deletion extends from position 3009 to position 3037 of the corresponding sequence in *Paenibacillus* sp. strain A (SEQ ID NO: 11). A second deletion extends from position 3047 to position 3317 of the corresponding sequence in *Paenibacillus* sp. strain A (SEQ ID NO: 11). Both deletions fall within the A domain of the third module of the FusA fusaricidin synthetase (i.e., FusA-A3).

As explained above, each of the A domains contains ten conserved amino acid residues responsible for substrate recognition and activation (see Table 1). These conserved amino acid residues are outlined in the alignment shown in FIG. 13. The deletions identified in the variant FusA fusaricidin synthetase expressed by *Paenibacillus* sp. strain NRRL B-50972 remove all but the last conserved amino acid residue (i.e., Lys517 located at position 3486 of SEQ ID NO: 11).

These two deletions in the variant FusA fusaricidin synthetase are present in the strains derived from *Paenibacillus* sp. strain NRRL B-50972 including the variant strain with a stable colony morphology designated herein as *Paenibacillus* sp. strain NRRL B-67129. Random mutant strains derived from *Paenibacillus* sp. strain NRRL B-50972 will generally maintain the deletions in the variant FusA-A3 as reversion to the wild-type FusA-A3 is extremely unlikely due to the extensive nature of the deletions.

Example 13. Comparison of Fusaricidin Production in *Paenibacillus* sp. Strain NRRL B-50972 And *Paenibacillus* sp. Strain A To determine the effect of the variant FusA-A3 a panel of fusaricidins and Paeniserines was quantified in *Paenibacillus* sp. strain NRRL B-50972 (expressing the variant FusA-A3) and *Paenibacillus* sp. strain A (expressing the wild-type FusA-A3) using the method described in Example 14. The identity of each compound was determined by its unique retention time and mass. The relative signal intensities of each peak in the spectra are presented in Table 15. Absolute quantification was not possible in the absence of purified standards. However, similar amounts of each cell extract were injected and relative amounts of the compounds can be estimated from the resulting signal intensities.

TABLE 15

| Compound | RT | Mass | NRRL B-50972 | Strain A |
|---|---|---|---|---|
| Fusaricidin C | 10.35 | 946.6 | 0 | 226457229 |
| Fusaricidin D | 10.43 | 960.6 | 0 | 116424723 |
| Paeniserine A1 | 11.00 | 868.5 | 208029 | 0 |
| Paeniserine B1 | 11.22 | 868.5 | 871001 | 317056 |
| Fusaricidin B | 13.23 | 896.6 | 9840703 | 461022017 |
| Fusaricidin A | 13.27 | 882.6 | 28024006 | 794055383 |
| LiF05b | 16.56 | 910.6 | 9978253 | 145941253 |

TABLE 15-continued

| Compound | RT | Mass | NRRL B-50972 | Strain A |
|---|---|---|---|---|
| LiF05a | 16.64 | 896.6 | 33071793 | 280586192 |
| LiF06a | 17.96 | 896.6 | 6594451 | 11862306 |
| LiF06b | 17.99 | 910.6 | 1600867 | 7441646 |
| LiF07b | 18.10 | 944.6 | 0 | 263137626 |
| LiF07a | 18.12 | 930.6 | 0 | 522229025 |
| LiF08b | 19.68 | 924.6 | 3546312 | 47167630 |
| LiF08a | 19.71 | 910.6 | 20378028 | 75820378 |

Figure 14:
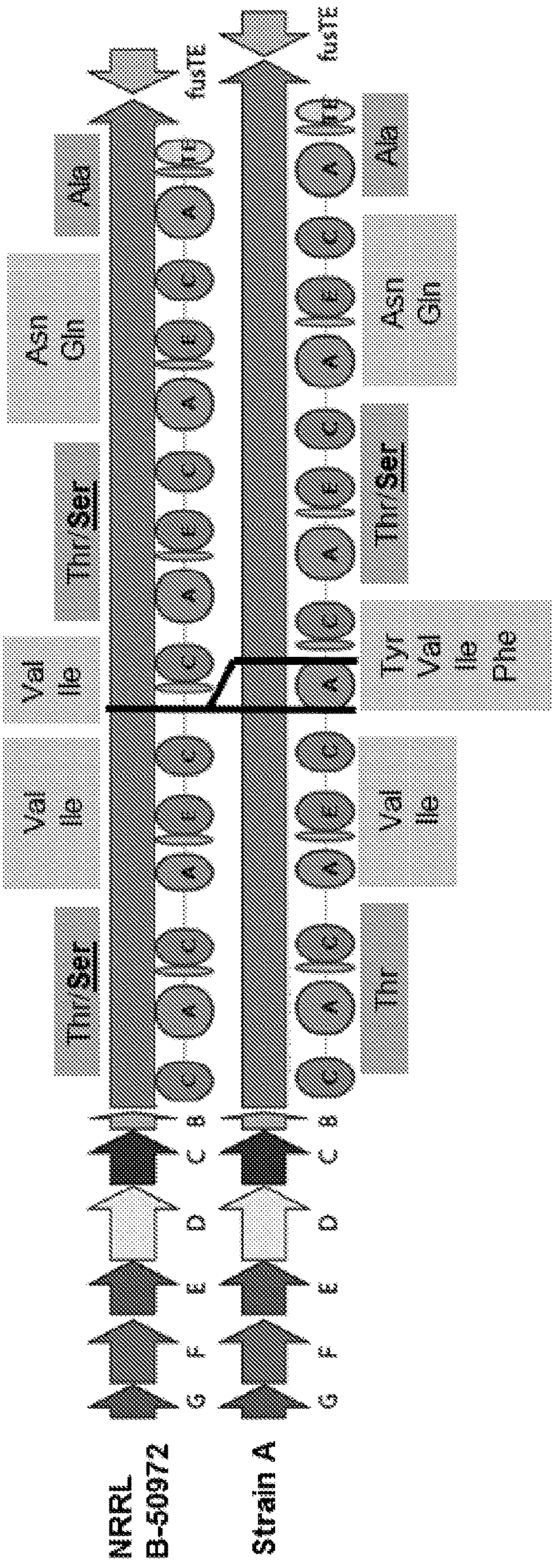
FIG. 14 depicts the fusaricidin gene cluster in *Paenibacillus* sp. strain NRRL B-50972 and *Paenibacillus* sp. strain A ("Strain A"). The arrows represent individual genes within the cluster (i.e.,fusG is represented by the "G" arrow, fusF is represented by the "F" arrow, etc.). The largest arrow represents thefusA fusaricidin synthetase gene with the following abbreviations and symbols: A=adenylation domain (substrate recognition and activation); C=condensation domain (peptide bond formation); E=epimerization domain (substrate racemization); TE=thioesterase domain (product release); oval without a letter=thiolation (T) domain (peptide carrier protein). The fusA gene has six modules responsible for incorporating the amino acids indicated in the boxes above or below each gene cluster. Strain A has a typical fusaricidin gene cluster whereas the *Paenibacillus* sp. strain NRRL B-50972 fusaricidin gene cluster is missing a functional A domain in module 3. As a result, the fusaricidins produced by *Paenibacillus* sp. strain NRRL B-50972 lack tyrosine and phenylalanine at position (3) and only incorporate valine or isoleucine.

In the wild-type FusA fusaricidin synthetase, FusA-A3 is responsible for incorporating L-Tyr, L-Phe, L-Val, L-Ile, or L-allo-Ile into the fusaricidin compound at amino acid position (3) (see Table 1). The variant FusA-A3 in *Paenibacillus* sp. strain NRRL B-50972 resulted in an extract without any detectable fusaricidin C, fusaricidin D, LiF07a, or LiF07b. Fusaricidin C and fusaricidin D both have a tyrosine at amino acid position (3) while LiF07a and LiF07b both have a phenylalanine at amino acid position (3). These experimental data demonstrate that the genetic variation in FusA-A3 expressed by *Paenibacillus* sp. strain NRRL B-50972 inhibits the biosynthesis of fusaricidins with a tyrosine or a phenylalanine at amino acid position (3) (see FIG. 14).

Thus, *Paenibacillus* sp. strain NRRL B-50972 and mutant strains derived from *Paenibacillus* sp. strain NRRL B-50972 are not capable of producing detectable amounts of fusaricidins or fusaricidin-like compounds with a tyrosine or phenylalanine at amino acid position (3) (e.g., Fusaricidins C and D or LiF07a and LiF07b). The analysis of the variant FusA-A3 in *Paenibacillus* sp. strain NRRL B-50972 indicates that this strain and its mutants are genetically incapable of producing fusaricidins or fusaricidin analogues with peptide rings comprising a tyrosine amino acid or phenylalanine amino acid at amino acid position (3).

Of the two Paeniserines analyzed, there was only one detectable in *Paenibacillus* sp. strain A, and its signal intensity was less than half of the corresponding signal intensity observed with the *Paenibacillus* sp. strain NRRL B-50972 extract. Without wishing to be bound to any theory, it appears that one or more of the first nine conserved amino acids in FusA-A3 (i.e., Asp235, Ala236, Ser239, Thr278, Leu299, Ala30l, Ala/Gly322, Val330, and Cys331) are responsible for recognition and activation of tyrosine and phenylalanine at position (3) in the fusaricidin compounds. Moreover, the variant FusA-A3 expressed by *Paenibacillus* sp. strain NRRL B-50972 may shift metabolic intermediates away from production of certain fusaricidins towards biosynthesis of a broader range of fusaricidin-like compounds (e.g., the Paeniserines).

Example 14. Comparison of Bioactivity of *Paenibacillus* sp. Strain NRRL B-50972 and *Paenibacillus* sp. Strain A

*Paenibacillus* sp. strain NRRL B-50972 (expressing the variant FusA-A3) and *Paenibacillus* sp. strain A (expressing the wild-type FusA-A3) were cultured in a soy-based medium to produce whole broths. The whole broths were diluted in a mixture of water and organic solvent to concentrations of 10%, 5%, 2.5%, and 1.25%. The diluted whole broths were applied to young plants which were subsequently exposed to an inoculum of *Puccinia* triticina (PUCCRT), *Botrytis cinerea* (BOTRCI), or *Phytophthora infestans* (PHYTIN). Several days after exposure to the inoculum of plant pathogen, each plant was scored for percent control of the pathogen relative to the untreated control plants. Each treatment was evaluated with three replicates and the average percent control reported (see Tables 16-18).

In each of the assays, *Paenibacillus* sp. strain NRRL B-50972 demonstrated, superior control over *Paenibacillus* sp. strain A. These experimental data suggest that the variant fusaricidin synthetase and the resulting changes in the biosynthesis of fusaricidins and fusaricidin-like compounds result in enhanced control of plant pathogens with *Paenibacillus* sp. NRRL B-50972.

TABLE 16

Control of *Puccinia triticina* (PUCCRT) achieved with *Paenibacillus* sp. strain NRRL B-50972 and *Paenibacillus* sp. strain A at dilution rates of 10%, 5%, 2.5%, and 1.25%.

| Treatment | Application Rate | Average Percent Control |
|---|---|---|
| *Paenibacillus* sp. NRRL B-50972 | 10% | 98 |
| | 5% | 88 |
| | 2.5% | 58 |
| | 1.25% | 0 |
| *Paenibacillus* sp. strain A | 10% | 82 |
| | 5% | 33 |
| | 2.5% | 0 |
| | 1.25% | 0 |

TABLE 17

Control of *Botrytis cinerea* (BOTRCI) achieved with *Paenibacillus* sp. strain NRRL B-50972 and *Paenibacillus* sp. strain A at dilution rates of 10%, 5%, 2.5%, and 1.25%.

| Treatment | Application Rate | Average Percent Control |
|---|---|---|
| *Paenibacillus* sp. NRRL B-50972 | 10% | 100 |
| | 5% | 100 |
| | 2.5% | 98 |
| | 1.25% | 42 |
| *Paenibacillus* sp. strain A | 10% | 97 |
| | 5% | 83 |
| | 2.5% | 17 |
| | 1.25% | 0 |

TABLE 18

Control of *Phytophthora infestans* (PHYTIN) achieved with *Paenibacillus* sp. strain NRRL B-50972 and *Paenibacillus* sp. strain A at dilution rates of 10%, 5%, 2.5%, and 1.25%.

| Treatment | Application Rate | Average Percent Control |
|---|---|---|
| *Paenibacillus* sp. NRRL B-50972 | 10% | 100 |
| | 5% | 99 |
| | 2.5% | 99 |
| | 1.25% | 90 |
| *Paenibacillus* sp. strain A | 10% | 97 |
| | 5% | 87 |
| | 2.5% | 67 |
| | 1.25% | 33 |

Example 15. Identification of Fusaricidins in *Paenibacillus* sp. Cell Extract

*Paenibacillus* sp. strain NRRL B-50972 and/or strains derived therefrom were grown in a soy-based medium until they reached stationary phase at which time the whole broth culture was harvested and extracted with organic solvent to produce a cell extract.

A chromatographic method using high-performance liquid chromatography/mass spectrometry time-of-flight (HPLC/MS TOF) was developed to separate the many fusaricidin-like molecules from the cell extract: Column: YMC™ Basic 4.6×250 mm, Spm; Water (0.1% FA) and Acetonitrile (0.1% formic acid (FA)); Gradient (% B): 0-9 min 28-30%; 9-14 min 30-33%; 14-34 min 33-50%; Wash.

Figure 4A:
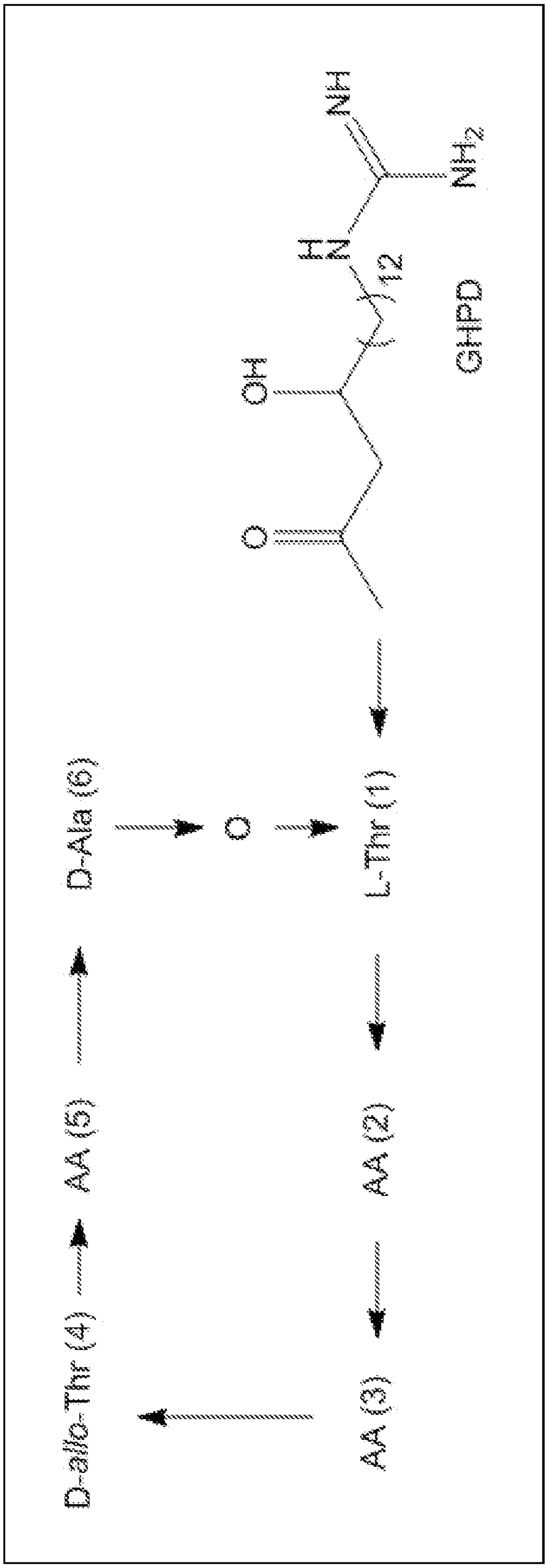
FIG. 4A presents a diagram outlining the structure of the known fusaricidins with conserved amino acids at positions (1), (4), and (6) identified and amino acids that vary indicated as AA (amino acid). The 15-guanidino-3-hydroxypentadecanoic acid (GHPD) tail forms an amide bond with the N-terminus of the L-threonine at position (1). The C-terminus of D-alanine at position (6) forms an ester linkage with the hydroxyl group of L-threonine at position (1) indicated with arrows pointing to an "O".
Figure 4B:
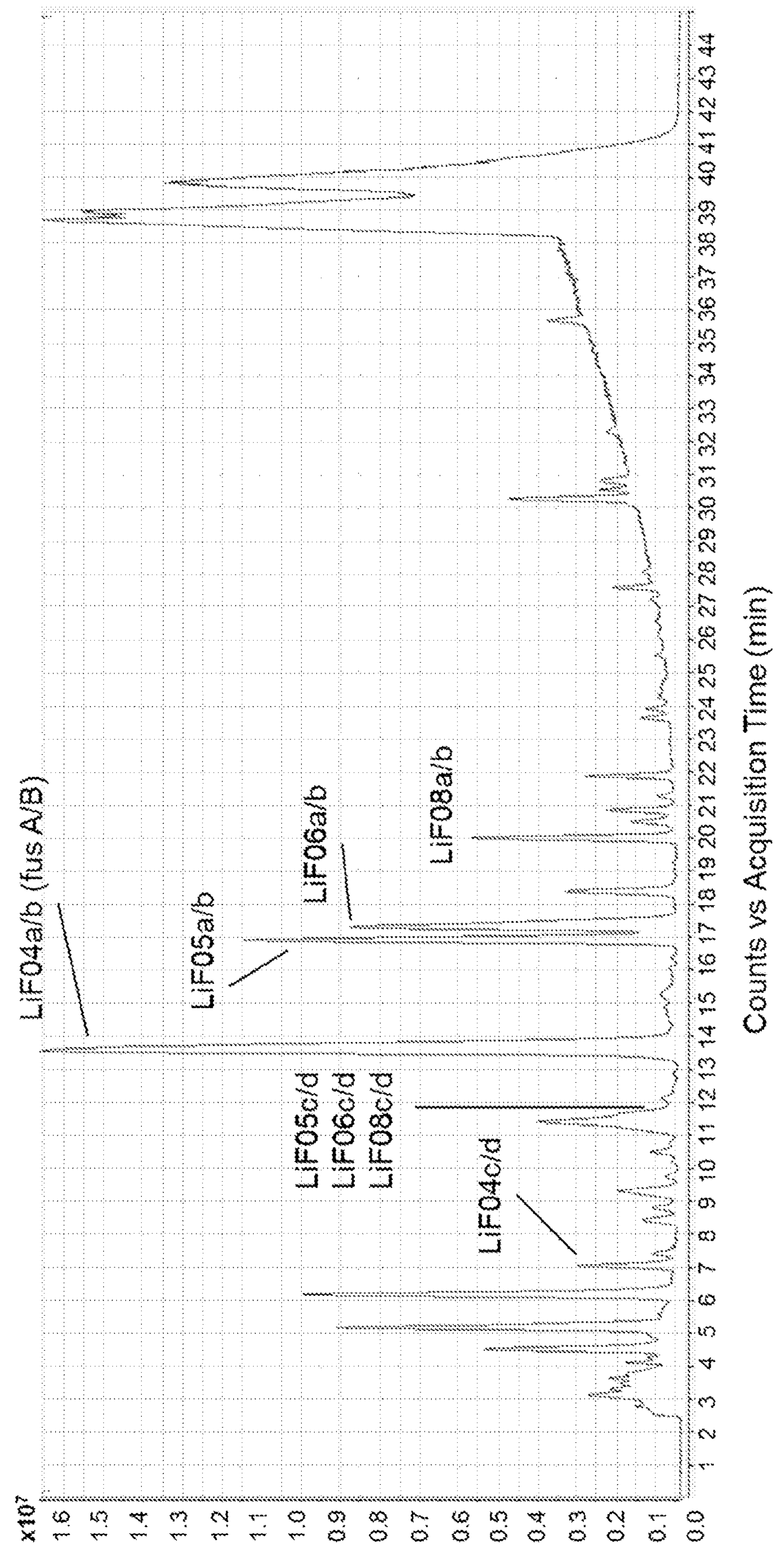
FIG. 4B shows an HPLC/MS TOF chromatogram from a *Paenibacillus* sp. cell extract in which the known fusaricidins are identified.

A chromatogram from the cell extract in which the known fusaricidins are identified is shown in FIG. 4B. The general structure of the fusaricidins is presented in FIG. 4A. Each cyclic fusaricidin has a corresponding acyclic analog.

All detectable fusaricidins in the cell extract were identified based on their retention times and m/z values (see FIG. 4C). Interestingly, fusaricidins C and D and other fusaricidins in which the amino acid at position (3) is a tyrosine or a phenylalanine were not detectable in the cell extract.

Example 16. Characterization of Paeniserines in *Paenibacillus* sp. Cell Extract To identify other compounds in the cell extract of *Paenibacillus* sp. strain NRRL B-50972 and/or strains derived therefrom a chromatographic method using ultra performance liquid chromatography/mass spectrometry triple time of flight (UPLC/MS Triple TOF) was developed to fragment the many fusaricidin-like molecules: Column: ZORBAX™ Eclipse Plus, 2.1×100 mm, 1.8 μm; Water (0.1% FA) and acetonitrile (0.1% FA); Gradient (% B): 0-5 min 10-95%; Wash.

With this method Applicant characterized a new Paeniserine family of fusaricidins by examining the mass fragmentation patterns obtained from an AB SCIEX TRIPLE TOF® mass spectrometer as well as by comparing spectra with published literature. Applicant named this new family the Paeniserines. Representative UPLC/MS Triple TOF fragmentation patterns and the corresponding chemical structures for Paeniserine A1 and Paeniserine B1 are shown in FIGS. 5 and 6, respectively. A similar analysis was performed for each of the Paeniserines detected in the cell extract.

Figure 5A:
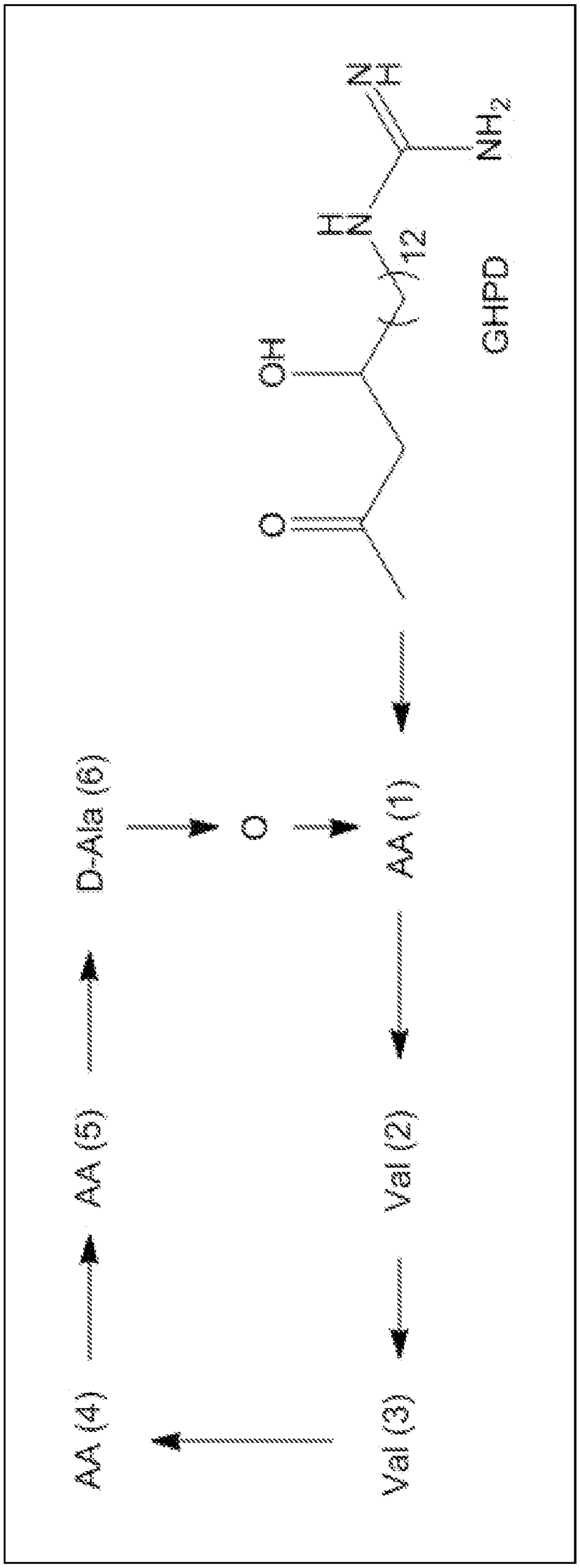
FIG. 5A presents a diagram outlining the structure of the Paeniserines. This class of compounds is similar to the fusaricidins except that one or both of the conserved threonines at positions (1) and (4) are substituted with a serine.
Figure 5B:
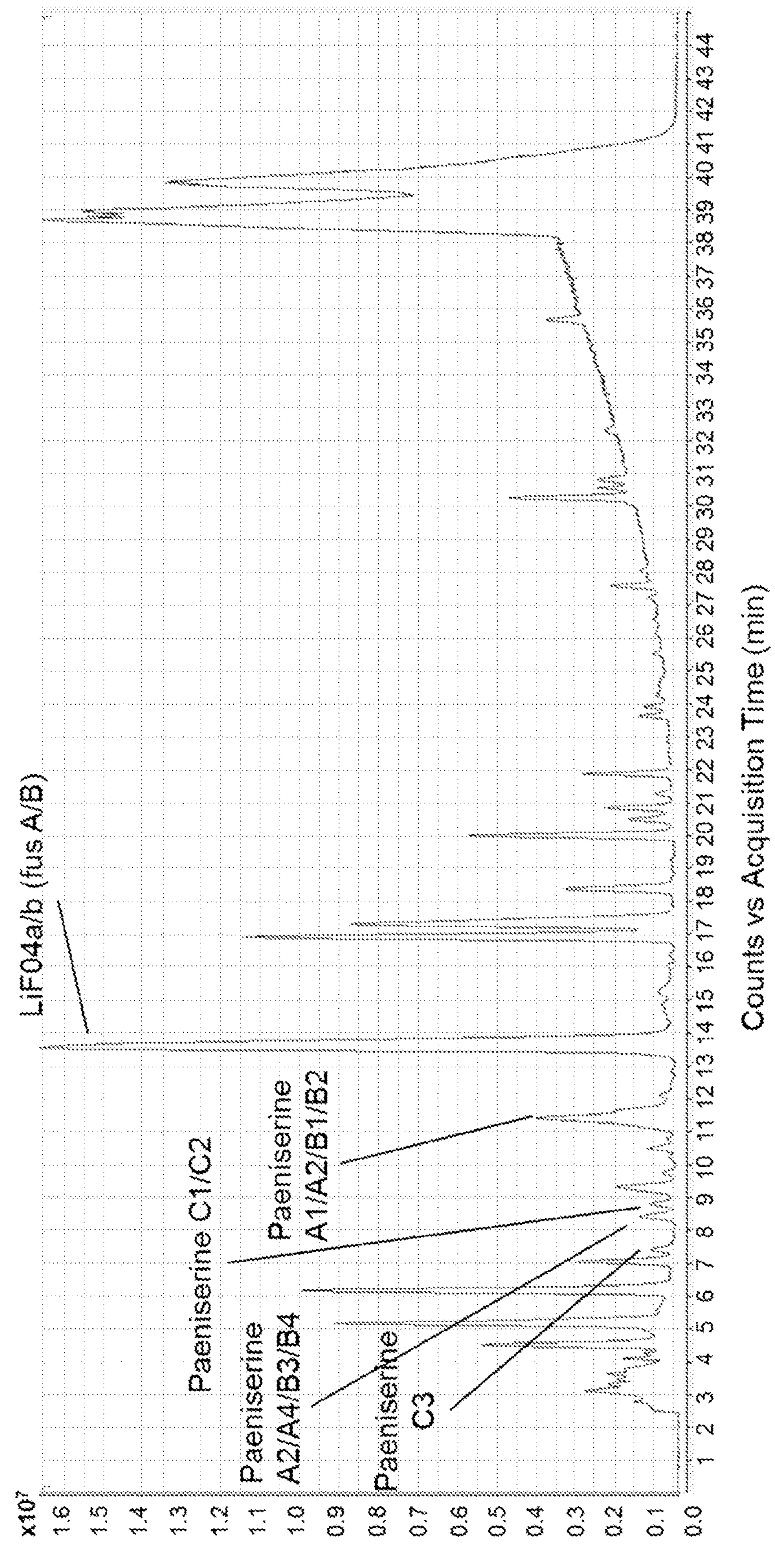
FIG. 5B shows an HPLC/MS TOF chromatogram of a cell extract from *Paenibacillus* sp. strain NRRL B-50972 and/or strains derived therefrom in which the Paeniserines are identified.
Figure 6A:
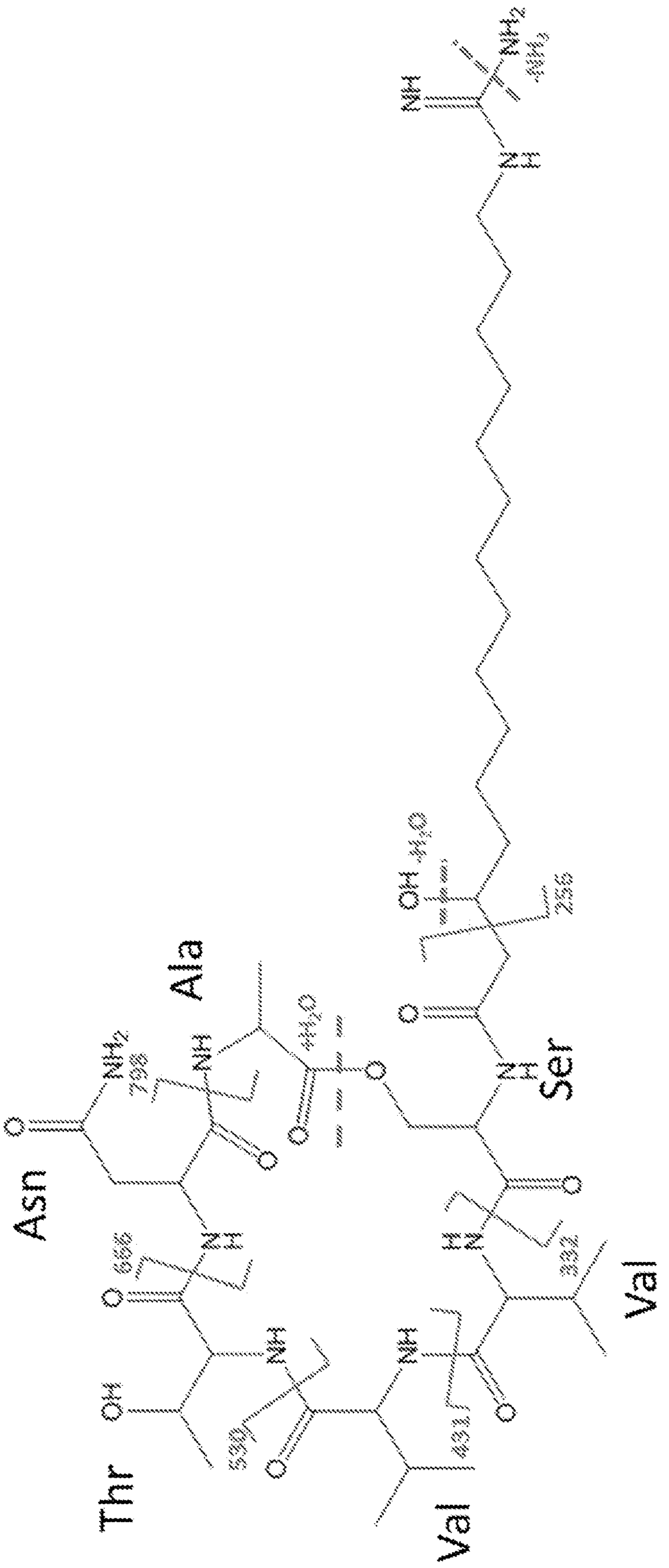
FIG. 6A depicts the chemical structure of Paeniserine A1 derived from the UPLC/MS Triple TOF spectrum shown in FIG. 6B.
Figure 6B:
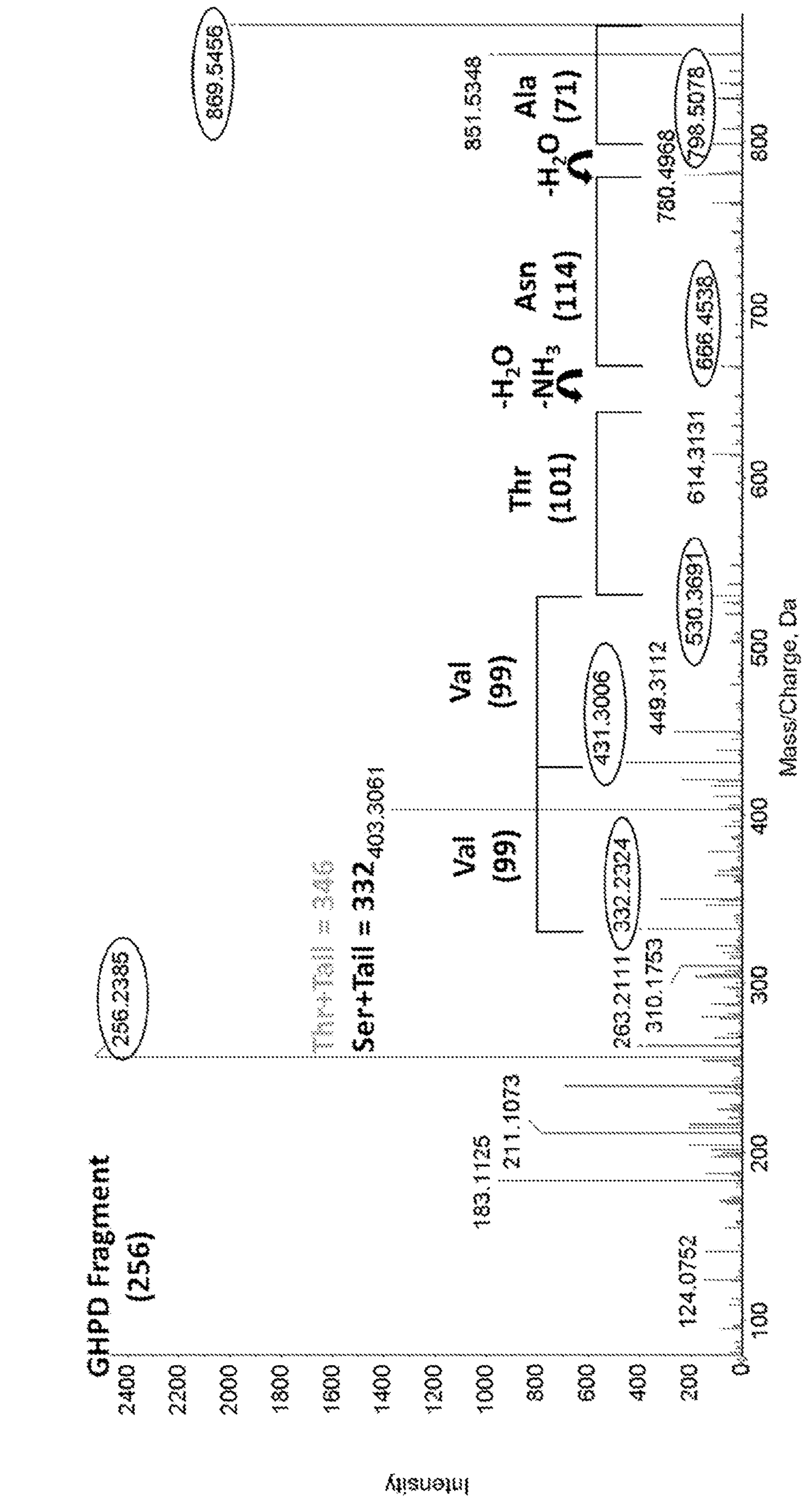
Figure 7A:
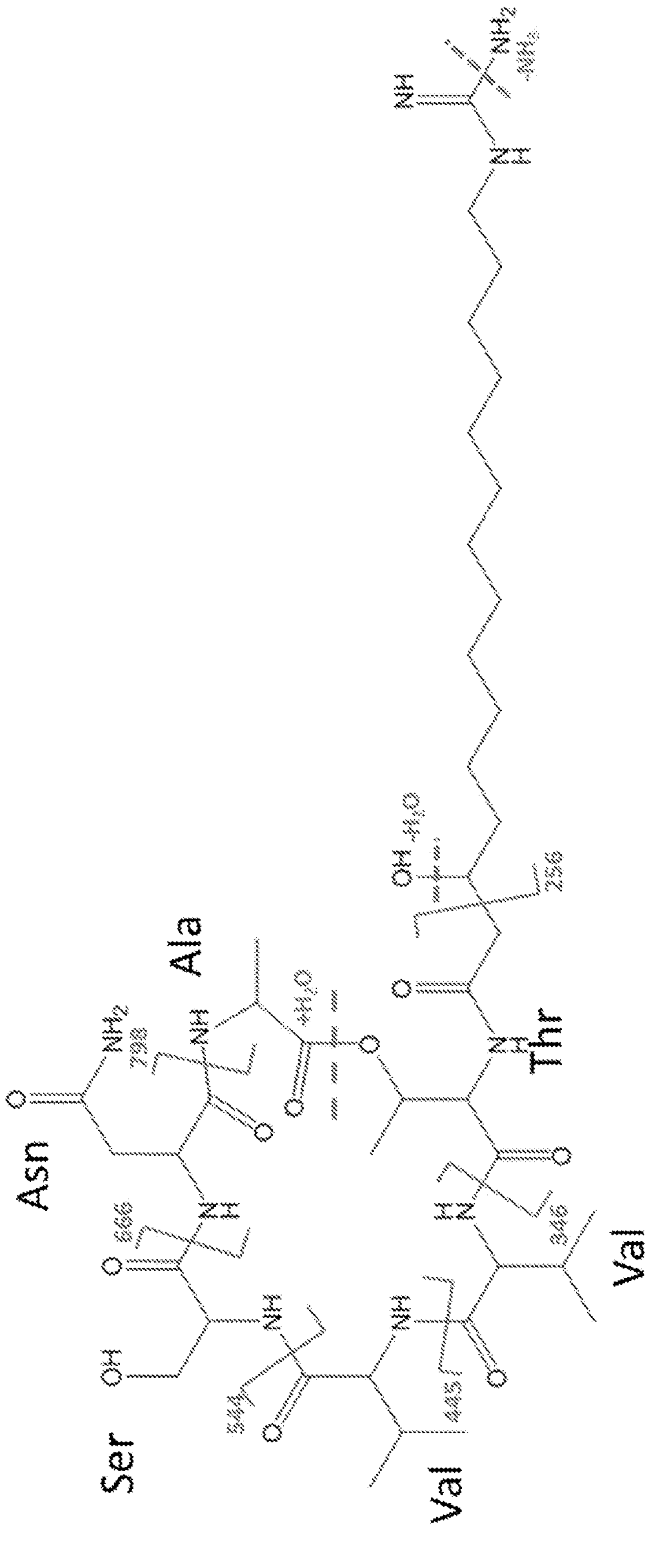
FIG. 7A depicts the chemical structure of Paeniserine B1 derived from the UPLC/MS Triple TOF spectrum shown in FIG. 7B.
Figure 7B:
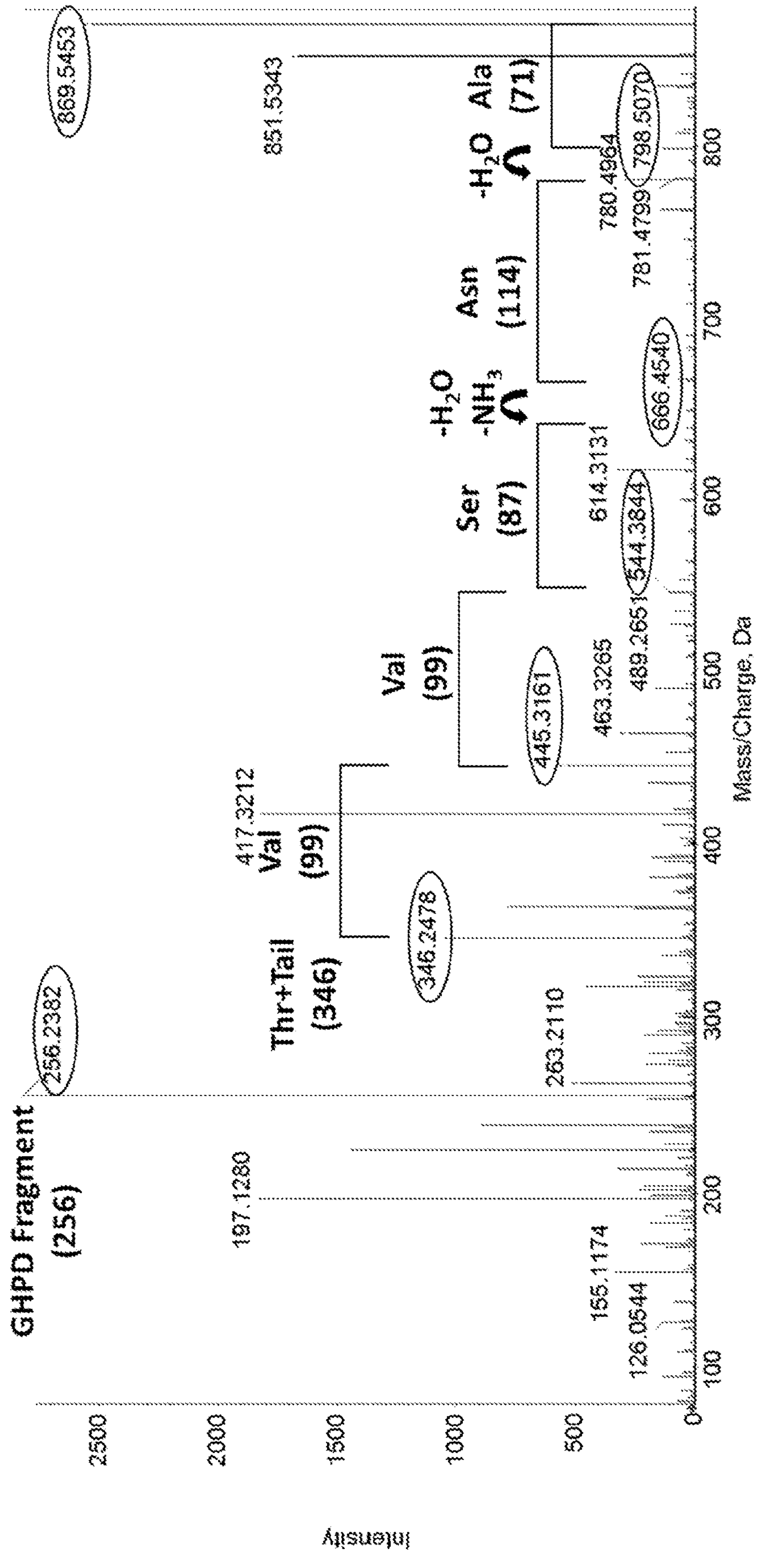

The Paeniserines were named as such due to the important departure from the fusaricidin skeleton with one or more serine substitutions (see FIG. 5A). Historically, to be considered a fusaricidin the peptide sequence contained three conserved amino acids: (1) threonine, (4) threonine, and (6) alanine. However, the Paeniserines show new substitutions with one or both of the (1) and (4) threonine residues replaced with a serine. The amino acids at positions (2) and (3) are both valine in the Paeniserines that Applicant characterized. A chromatogram in which the peaks corresponding to the Paeniserines are identified is shown in FIG. 5B.

Applicant also characterized this family of serine-substituted fusaricidin-like-compounds in the cell extract based on their retention times and m/z values (see FIG. 5C). Although Paeniserine C4 was not detectable it is reasonable to expect that it is produced based on the structures of the previously characterized fusaricidins. As with the fusaricidins, each cyclic Paeniserine has a corresponding acyclic analog.

It is important to note that although the Paeniserines that Applicant characterized had a valine amino acid in the (2) and (3) residues there likely exist compounds with variations in those positions. These potential variations would be similar to the Fusaricidin/LiF analogs with amino acids such as isoleucine, phenylalanine, and tyrosine as the (2) and (3) residues. In addition, although the GHPD tail is described above, it is likely that there exist compounds with variations in tail lengths similar to the Paeniprolixin family (see Example 17).

Figure 8A:
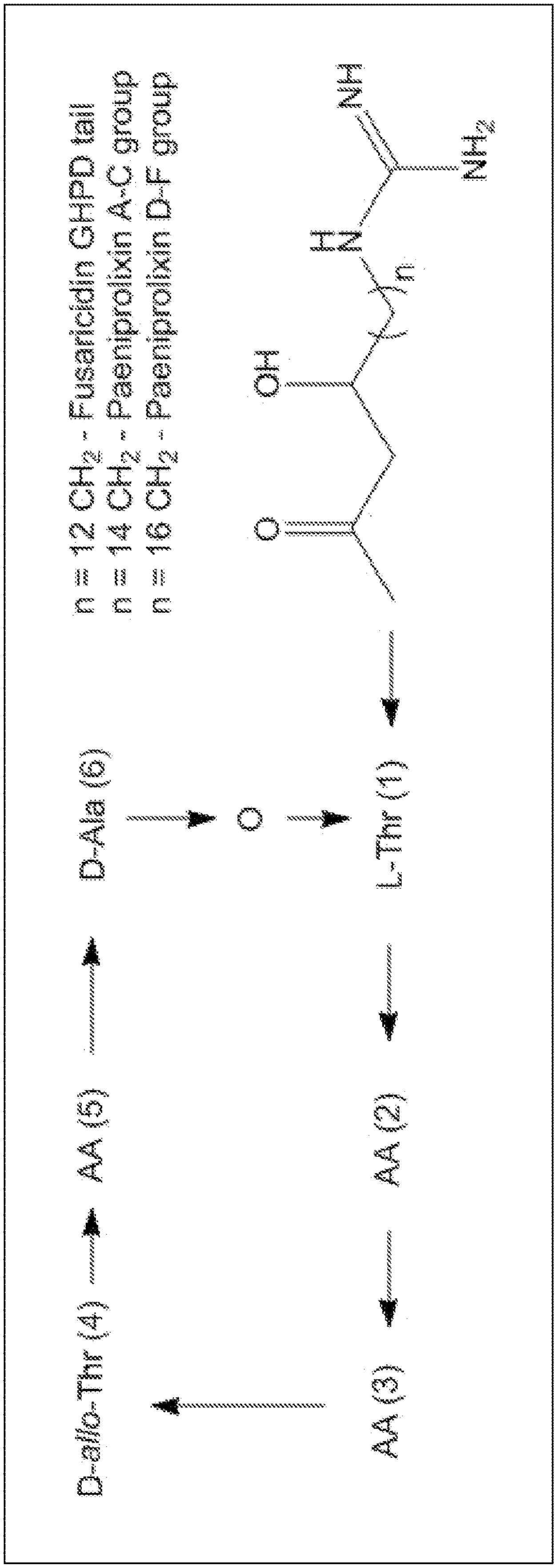
FIG. 8A presents a diagram outlining the structure of the Paeniprolixins. This class of compounds is similar to the fusaricidins except that the length of the GHPD tail is extended from $—(CH_2)_{12}—$ to $—(CH_2)_{14}—$ or $—(CH_2)_{16}—$.

Example 17. Characterization of Paeniprolixins in *Paenibacillus* sp. Cell Extract The cell extract of *Paenibacillus* sp. strain NRRL B-50972 and/or strains derived therefrom was analyzed further with the chromatographic method described in Example 14. A new family of fusaricidins was characterized by examining the mass fragmentation patterns obtained from an AB SCIEX TRIPLE TOF® mass spectrometer as well as by comparing spectra with published literature. Applicant named this new family the Paeniprolixins. Representative UPLC/MS Triple TOF fragmentation patterns and the corresponding chemical structures for Paeniprolixin C1 and Paeniprolixin D1 are shown in FIGS. 8 and 9, respectively. A similar analysis was performed for each of the Paeniprolixins detected in the cell extract.

The Paeniprolixins were named from the Latin word prolix (meaning lengthy) due to another important departure from the fusaricidin skeleton in the aliphatic tail, namely, the Paeniprolixins have a longer tail than the fusaricidins. Historically, fusaricidins have only been observed to have the specific GHPD tail. This has been shown to be consistent even in the most recent publication on the matter (i.e., Vater et al., J. Am. Soc. Mass Spectrom., 2015, 26, 1130-1141) in which the authors claim, "This finding [GHPD tail strictly conserved] is in contrast to many other lipopeptides reported in literature, where the fatty acid part is a major target of structural variation [such as in] the surfactins, iturins, and fengycins." Applicant identified a family of longer tailed (i.e., 17-guanidino-3-hydroxyheptadecanoic acid or GHPD+$2CH_2$ and 19-guanidino-3-hydroxynonadecanoic acid or GHPD+$4CH_2$) fusaricidin-like compounds (see FIG. 8A) in the cell extract of *Paenibacillus* sp. NRRL B-50972. Unlike the Paeniserines, the Paeniprolixins maintain the conserved amino acid residues of L-threonine at position (1) and D-allo-threonine at position (4).

It is important to note that although the Paeniprolixins that Applicant characterized had either valine or isoleucine amino acids in the (2) and (3) residues there likely exist compounds with variations in those positions. These potential variations would be similar to the Fusaricidin/LiF analogs such as other combinations of valine, isoleucine, or other amino acids such as phenylalanine, and tyrosine as the (2) and (3) residues. In addition, there are likely to exist hybrid combinations with Paeniserines described above that have longer tail lengths.

Figure 8B:
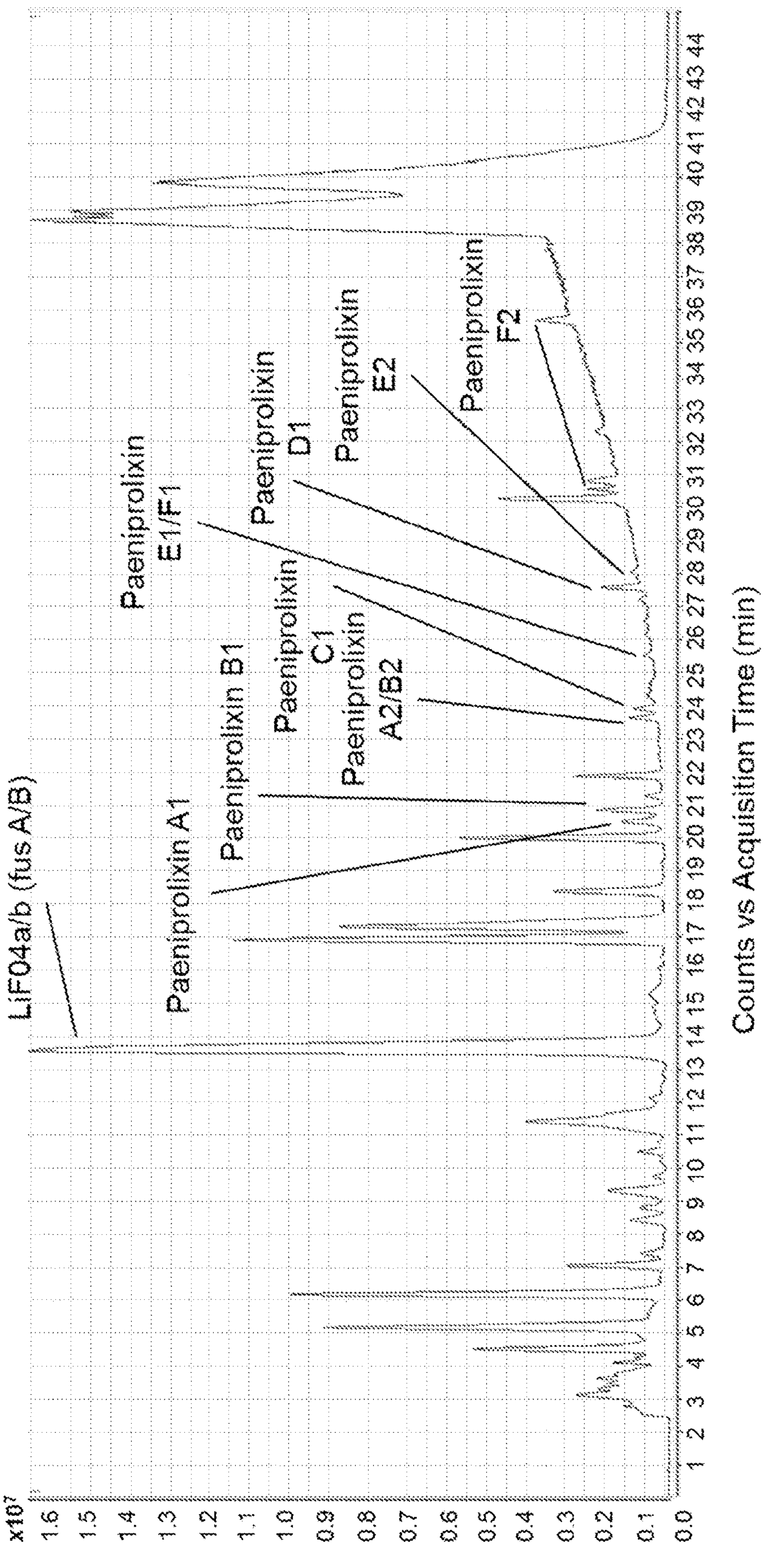
FIG. 8B shows an HPLC/MS TOF chromatogram of a cell extract from *Paenibacillus* sp. strain NRRL B-50972 and/or strains derived therefrom in which the Paeniprolixins are identified.
Figure 9A:
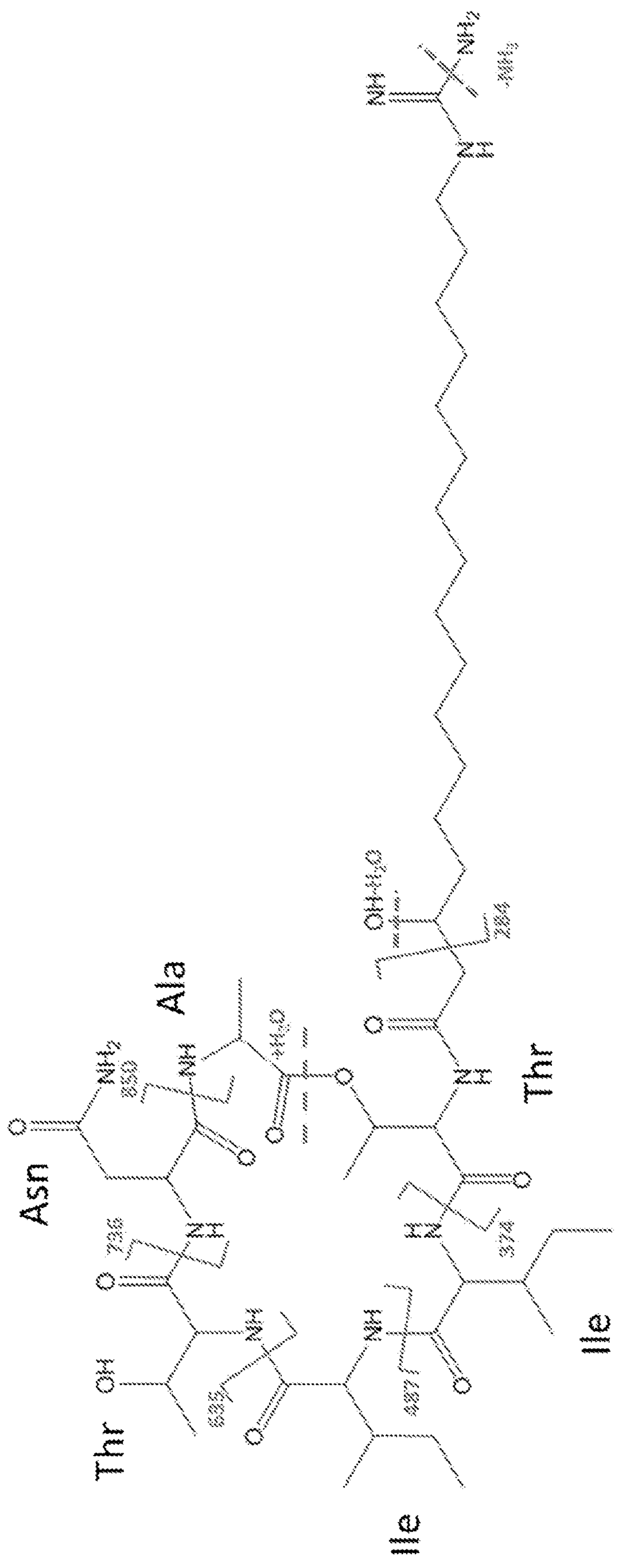
FIG. 9A depicts the chemical structure of Paeniprolixin C1 derived from the UPLC/MS Triple TOF spectrum shown in FIG. 9B.
Figure 9B:
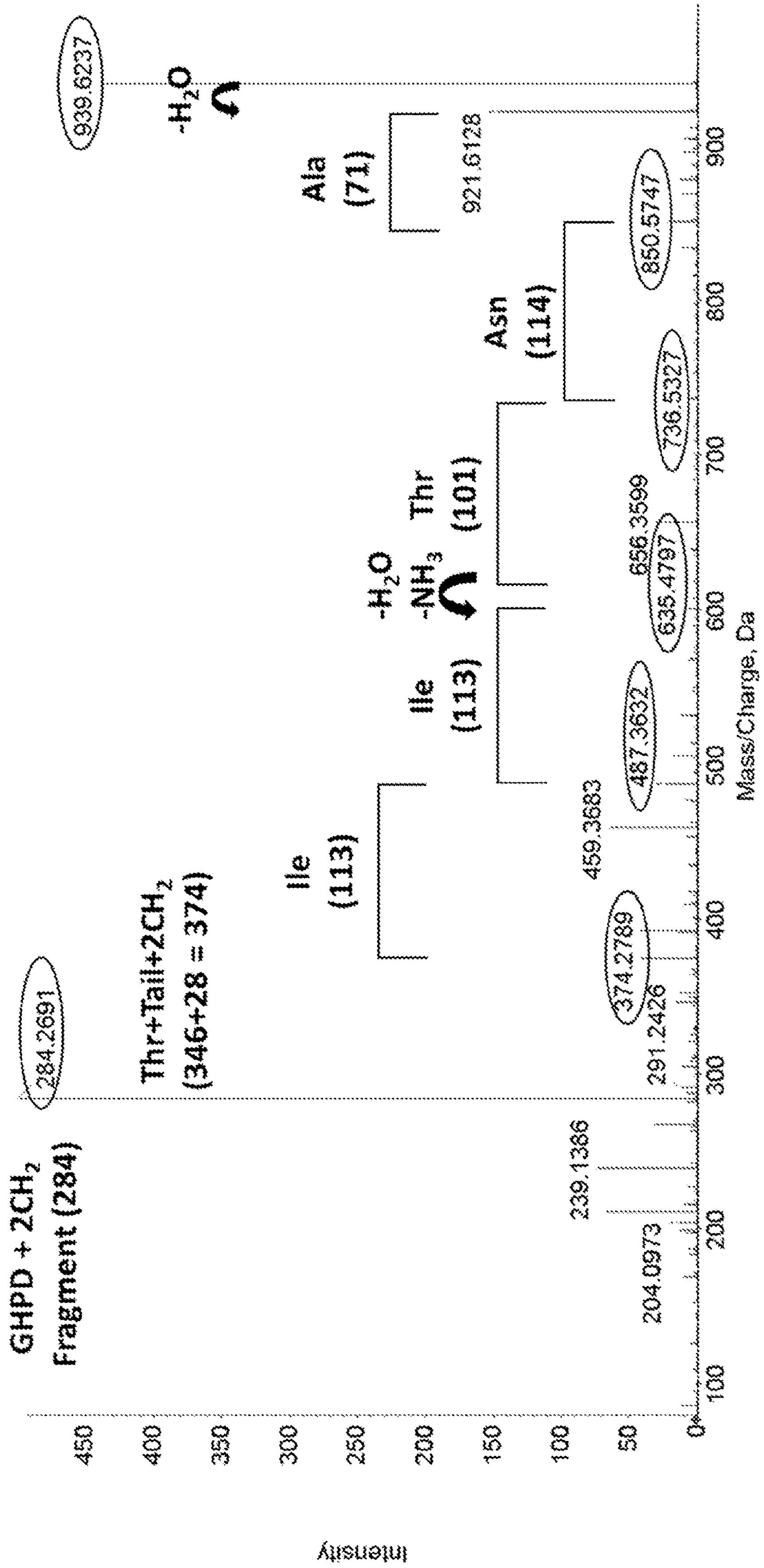
Figure 10A:
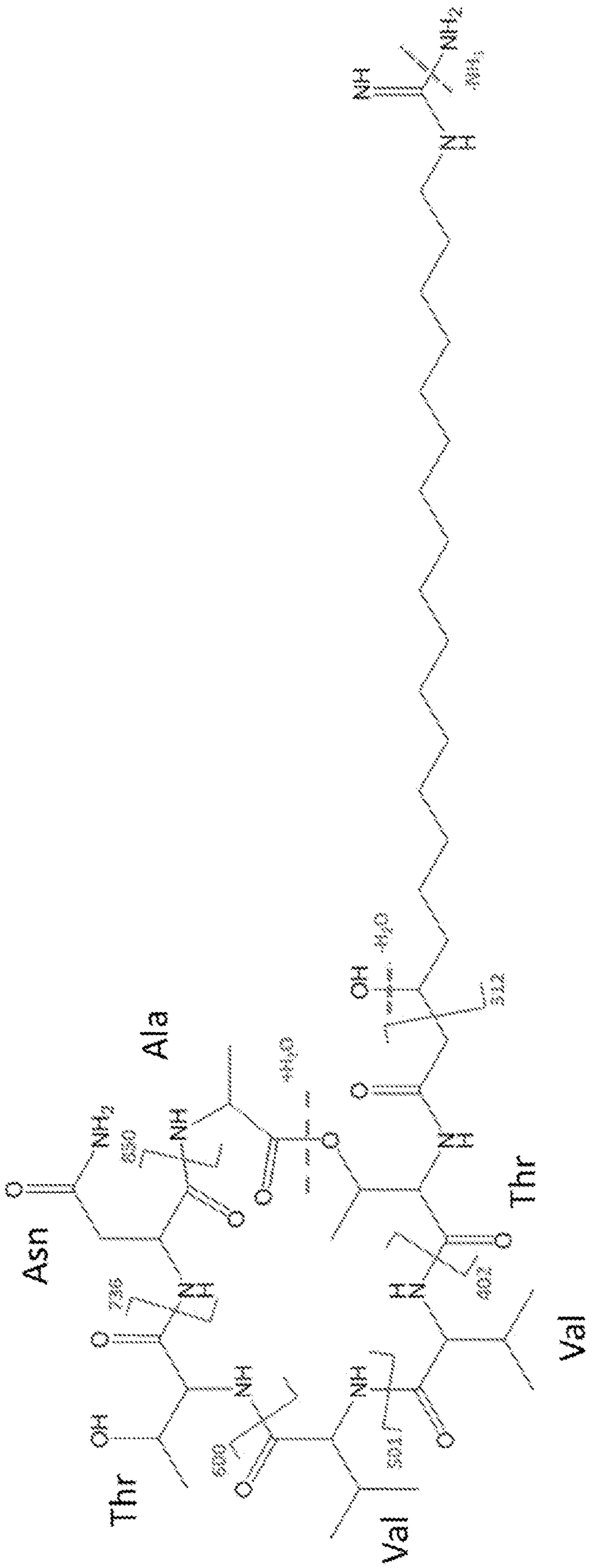
FIG. 10A depicts the chemical structure of Paeniprolixin D1 derived from the UPLC/MS Triple TOF spectrum shown in FIG. 10B.
Figure 10B:
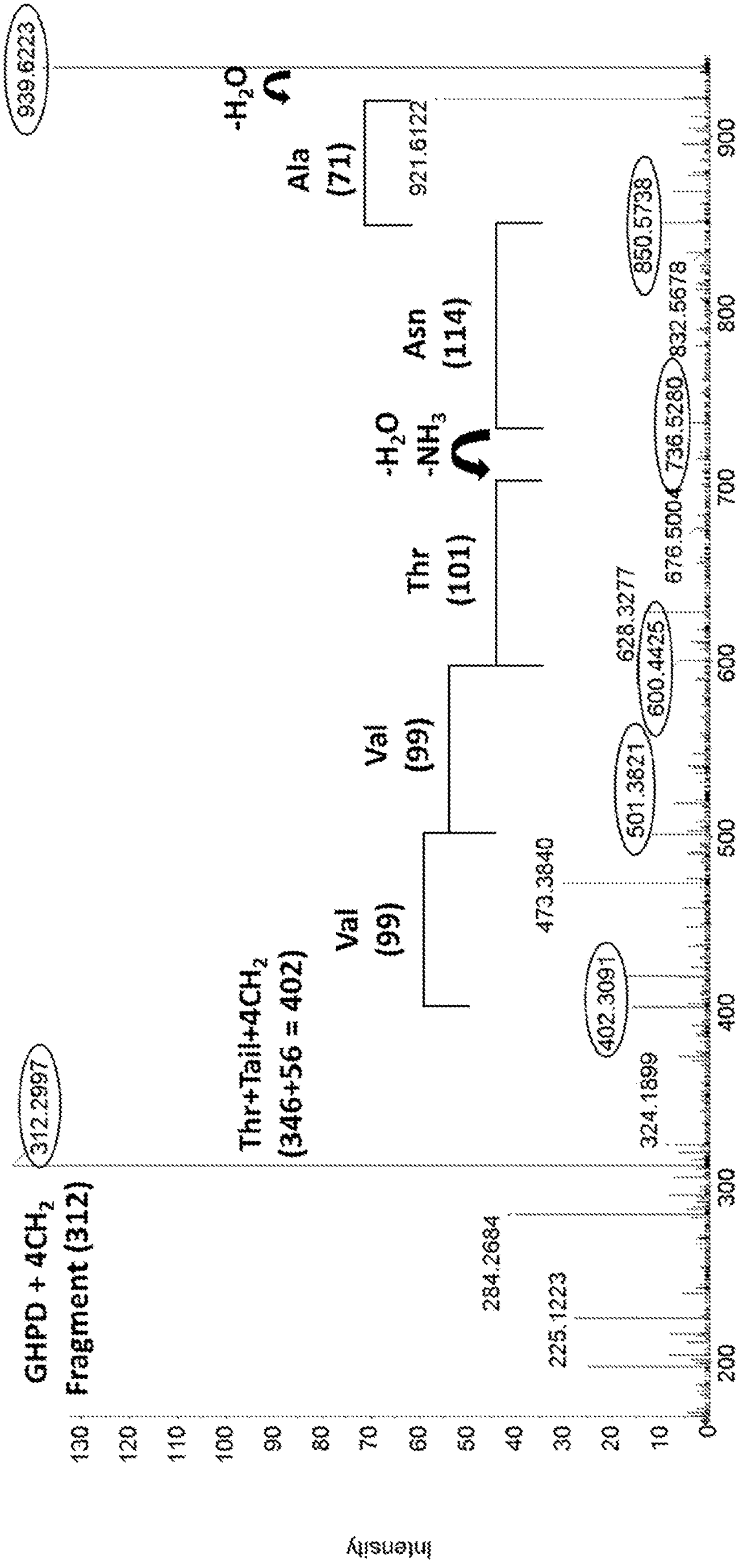

A chromatogram in which the peaks corresponding to the Paeniprolixins are identified is shown in FIG. 8B. This family of fusaricidin-like compounds with longer GHPD tails was also characterized based on their retention times and m/z values (see FIG. 8C). Although Paeniprolixins C2 and D2 were not detectable it is reasonable to expect that they are produced based on the structures of the previously characterized fusaricidins. As with the fusaricidins, each cyclic Paeniprolixin has a corresponding acyclic analog.

Example 18. Antifungal Bioactivity Profiles of the Paeniserines, Paeniprolixins, and Other Fusaricidins The samples shown in Table 19 were isolated from a *Paenibacillus* sp. cells. The fermentation whole broth was centrifuged to remove the supernatant. The pellet obtained was then extracted in methanol. The resulting extract was fractionated using reversed phase medium pressure liquid chromatography. The fractions were then further purified using reversed phase preparatory high pressure liquid chromatography.

TABLE 19

| Sample Code | Name | Description |
|---|---|---|
| Sample 1 | Paeniserines | Paeniserines A1, A2, B1, and B2 |
| Sample 2 | Fusaricidin A | Fusaricidin A (LiF04a), 85+% Pure |
| Sample 3 | LiF Asn Analogs | LiF05a and LiF06a |
| Sample 4 | LiF Asn/Gln Combo | LiF05a, LiF06a, LiF05b, and LiF06b |
| Sample 5 | LiF08s | LiF08a and LiF08b |
| Sample 6 | Paeniprolixins | Paeniprolixin A1, A2, B1, B2, E1 and F1 |

The in vitro antifungal 96-well plate assay utilizes the resazurin-based cell viability reagent PRESTOBLUE® as an indicator for fungal growth. Starting from fungal spores, the assay measures the potency of a sample to inhibit the germination of fungal spores and/or the growth of fungal cells. The assay was prepared with three agricultural-relevant fungal diseases: *Alternaria solani* (ALTESO), *Colletotrichum lagenarium* (COLLLA), and *Botrytis cinerea* (BOTRCI).

All the samples outlined in Table 19 proved to be active against the agriculturally-relevant fungal diseases (see the Minimum Inhibitory Concentration for 80% (MIC80) values given in units of parts per million (ppm) for each sample in Table 20). Interestingly, certain compounds seem to have varying activity against specific diseases. For example while the asparagine analogs in Sample 3-seems to be important in controlling ALTESO, the glutamine counterparts of the same type of compound in Sample 4 were more involved in the control of COLLLA. The longer-tailed analogs in Sample 6 were the most potent inhibitors of COLLLA. This suggests that while all are active in their own right, a combination of these chemistries is important to the final potency and spectrum of disease control of the final product.

TABLE 20

| | | MIC80 (in ppm) | | |
|---|---|---|---|---|
| Sample Code | Name | ALTESO | BOTRCI | COLLLA |
| Sample 1 | Paeniserines | 75 | 38 | 49 |
| Sample 2 | Fusaricidin A | 1.6 | 1.5 | 6.3 |
| Sample 3 | LiF Asn Analogs | 6.3 | 2.5 | 37 |
| Sample 4 | LiF Asn/Gln Combo | 55 | 19 | 9.3 |
| Sample 5 | LiF08s | 3.0 | 9.4 | 9.4 |
| Sample 6 | Paeniprolixins | 75 | 80 | 5.0 |

Example 19. Antibacterial Bioactivity Profiles of the Paeniserines, Paeniprolixins, and Other Fusaricidins The in vitro antibacterial 96-well plate assay uses absorbance as an indicator for bacterial growth. The assay measures the potency of a sample to inhibit bacterial growth by comparing the absorbance of the untreated wells to the sample wells. The last dilution/concentration that inhibits the growth of the bacteria is called the MIC (minimum inhibitory concentration) and this value can be used to compare the efficacy of different samples. The assay was evaluated with three agricultural-relevant bacterial diseases: *Xanthomonas campestris* (XANTAV), *Pseudomonas syringae* (PSDMTM), and *Erwinia carotovora* (ERWICA).

The samples outlined in Table 19 were applied in the antibacterial assays to determine the MIC80 values with each bacterial pathogen. The results of the assays are presented in Table 21. Samples 1-5 proved to be active against the agriculturally-relevant bacterial diseases. Interestingly, certain compounds seem to have varying activity against specific diseases. For example the Paeniserines complement well Fusaricidin A in that they are able to control PSDMTM, a weakness of Fusaricidin A. On the other hand, Fusaricidin A makes up for the weakness in controlling ERWICA observed with the Paeniserines. As with the fungal assays, this suggests that while all are active in their own right, a combination of these chemistries is important to the final potency and spectrum of disease control of the final product.

TABLE 21

| | | MIC80 (in ppm) | | |
|---|---|---|---|---|
| Sample Code | Name | PSDMTM | XANTAV | ERWICA |
| Sample 1 | Paeniserines | 99 | 44 | NDR* |
| Sample 2 | Fusaricidin A | NDR* | 24 | 75 |
| Sample 3 | LiF Asn Analogs | 101 | 12.4 | 62.5 |
| Sample 4 | LiF Asn/Gln Combo | 88 | 44 | 150 |
| Sample 5 | LiF08s | 125 | 23 | 49 |
| Sample 6 | Paeniprolixins | —** | —** | —** |

*NDR: no detectable result (i.e., no inhibition of bacterial growth at the highest concentrations tested)
**The sample was insoluble in the microbial media and was not able to be tested.

Figure 11:
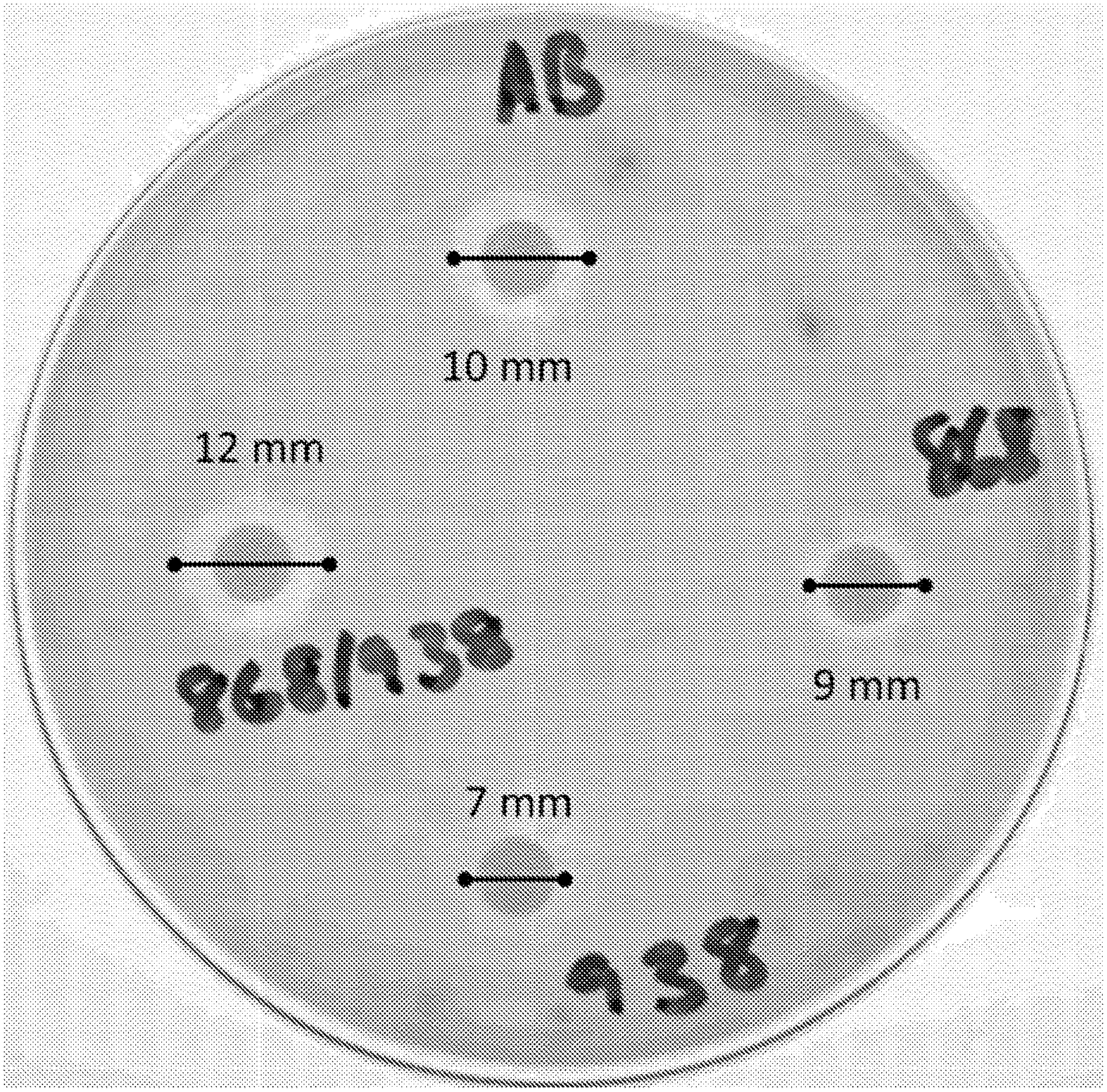
FIG. 11 depicts a Kirby-Bauer antibiotic disk diffusion assay with fusaricidins A and B ("AB"), Paeniserines A1 and B1 ("868"), Paeniprolixins A2 and B2 ("938"), or a combination of 868 and 938 applied to a lawn of spores of *Colletotrichum lagenarium* (COLLLA) on an agar plate. The diameter of each disk with its zone of inhibition of fungal growth is indicated in millimeters.

Example 20. Indication of Synergy with Kirby-Bauer Antibiotic Disk Diffusion Assay To gain an initial assessment of synergy between the various classes of fusaricidin-like compounds a bioassay was performed using the plant pathogen COLLLA. The bioassay was the classical Kirby-Bauer antibiotic disk diffusion assay on agar (Bauer, A. W., et al., 1966 Am. J. Clin. Pathol. 36:493-496). Briefly, blank sterile disks loaded with similar amounts of the various samples were placed on a Petri dish inoculated with a lawn of COLLLA spores. The Petri dish was incubated and the activity was recorded as the size of the diameter of the zone of inhibition exhibited around each disk. The results are illustrated in FIG. 11.

The results from this preliminary assay suggest a synergistic effect results when certain Paeniserines and Paeniprolixins are applied together. The Paeniserines A1 and B1 ("868") or the Paeniprolixins A2 and B2 ("938") applied separately show relatively small zones of inhibition in this assay. However, their combination ("868/938") shows the largest and cleanest zone of inhibition exceeding the results obtained with application of 868, 938, or fusaricidins A and B ("AB"). About 0.1 mg total material was applied to each sterile disk for the AB, 868, and 938 samples. The disk containing both 868 and 938 samples contained about 0.05 mg of each sample so that the total amount of material on the 868/938 disk was about 0.1 mg.

A limitation of this assay is the requirement that the fusaricidin compounds must diffuse through the agar to inhibit fungal growth. This initial indication of a synergistic effect will be further evaluated utilizing in vitro antifungal assays in liquid media.

Figure 12B:
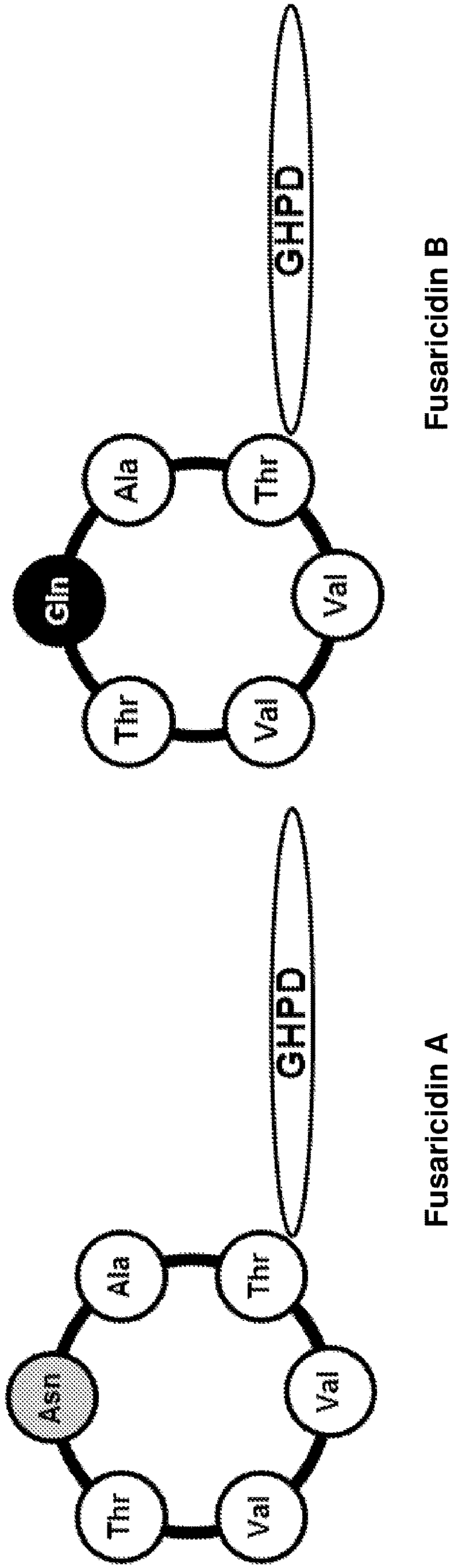
Figure 12C:
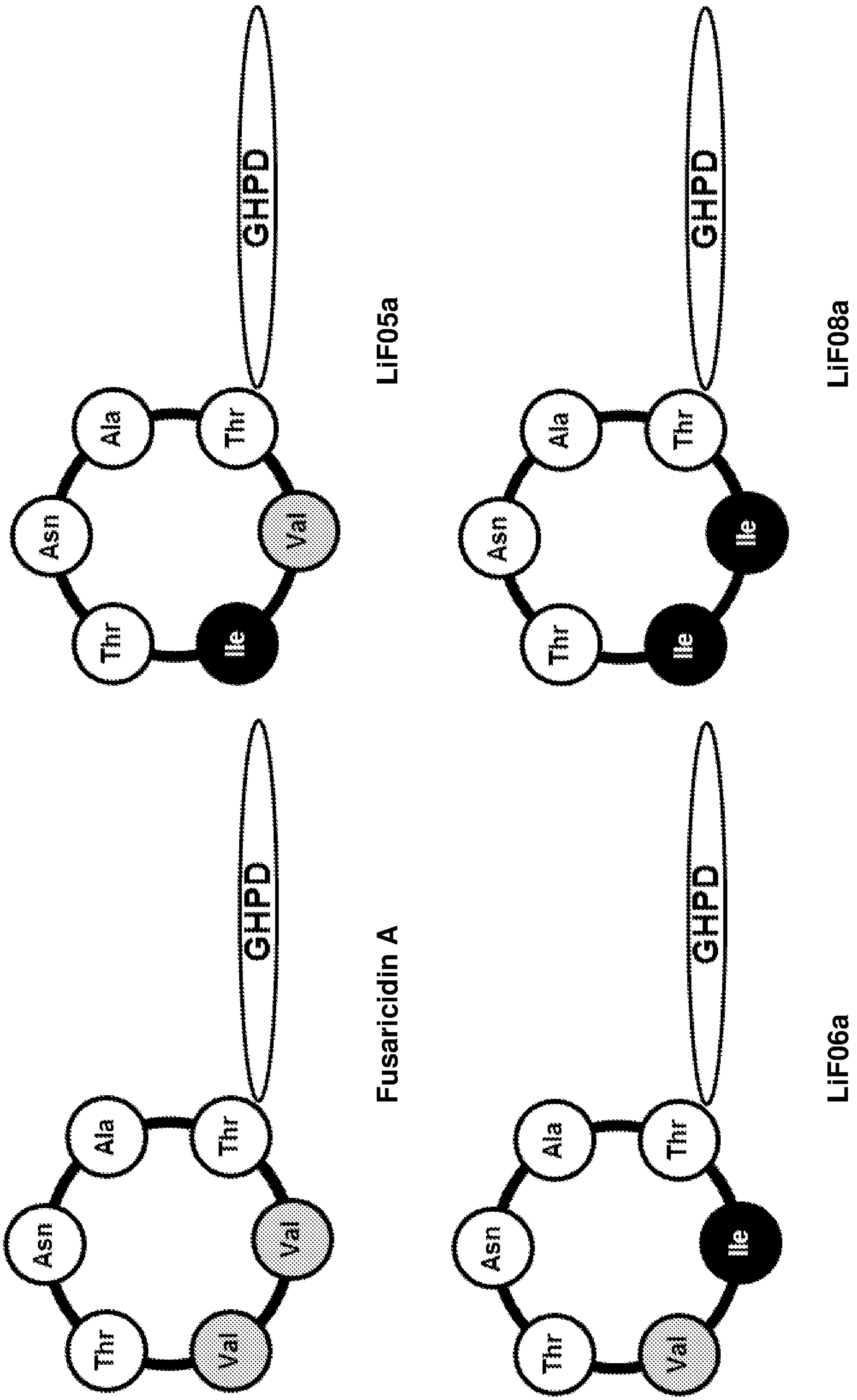
Figure 12D:
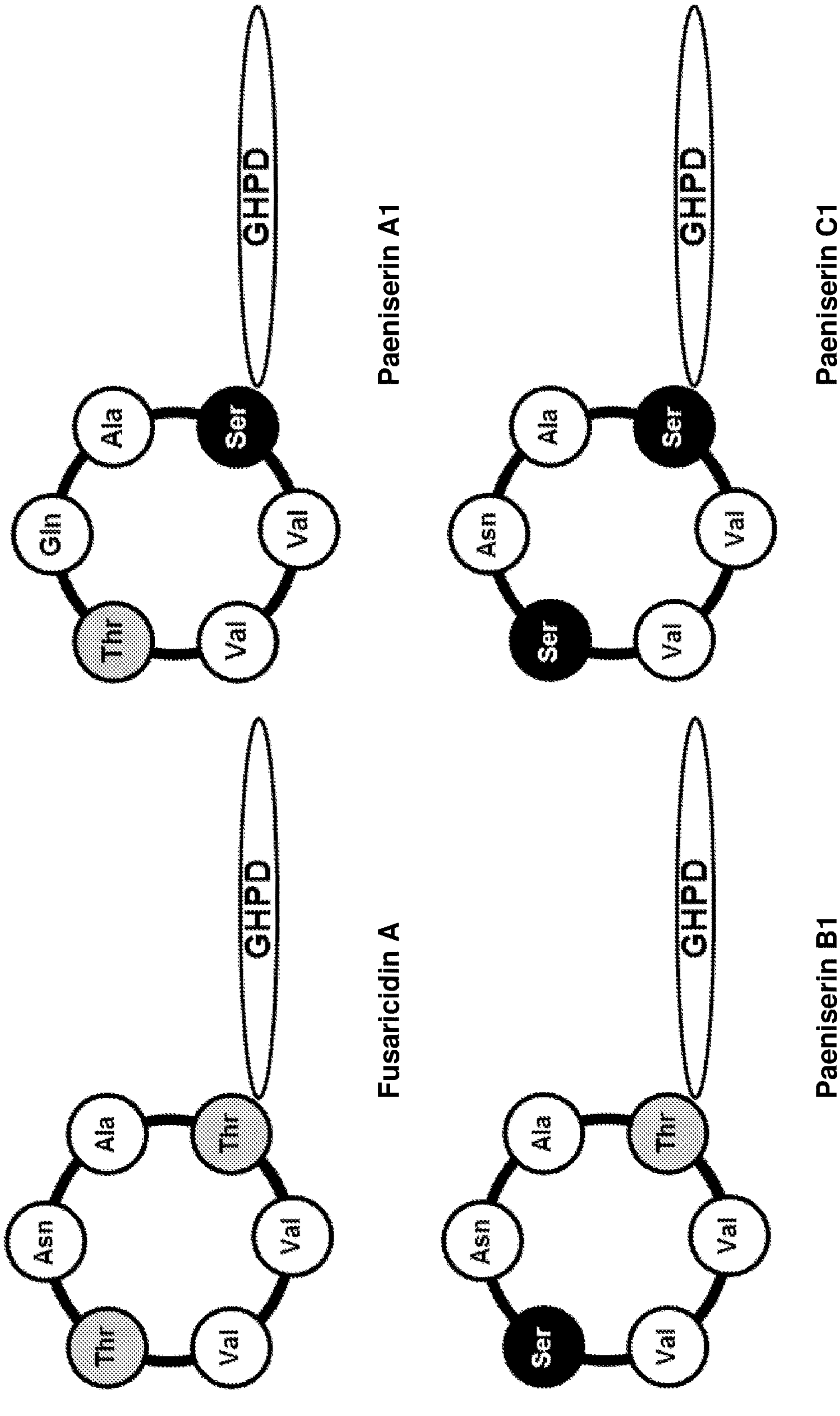

Example 21. In Vitro Antifungal Assays to Demonstrate Synergy of Fusaricidin Combinations In addition to the combinations of fusaricidins outlined in Example 17, in vitro antifungal assays in liquid media will be performed to demonstrate the proposed synergy resulting from application of combinations of fusaricidins and/or fusaricidin-like compounds shown in FIG. 12. Each of the groups shown in FIG. 12 will be evaluated individually to first assess structural characteristics and then in combinations to address synergy. Both binary and ternary mixtures will be assessed.

While the individual compounds may exhibit weaknesses with regard to the fungicidal activity, the combinations will have an activity which exceeds a simple addition of activities.

A synergistic effect of fungicides is always present when the fungicidal activity of the active compound combinations exceeds the total of the activities of the active compounds when applied individually.

The expected activity for a given combination of two or three active compounds can be calculated as follows (cf. Colby, S. R., "Calculating Synergistic and Antagonistic Responses of Herbicide Combinations, *Weeds* 1967, 15, 20-22):

If

X is the efficacy when active compound A is applied at an application rate of m ppm (or g/ha), Y is the efficacy when active compound B is applied at an application rate of n ppm (or g/ha), Z is the efficacy when active compound B is applied at an application rate of r ppm (or g/ha), $E_1$ is the efficacy when the active compounds A and B are applied at application rates of m and n ppm (or g/ha), respectively, $E_2$ is the efficacy when the active compounds A, B and C are applied at application rates of m, n and r ppm (or g/ha), respectively, then for a binary mixture:

$$E_1 = X + Y - \frac{X \cdot Y}{100}$$

and for a ternary mixture:

$$E_2 = X + Y + Z - \left(\frac{X \cdot Y + X \cdot Z + Y \cdot Z}{100}\right) + \frac{X \cdot Y \cdot Z}{10000}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, A Graphic Representation of Synergism in Pesticides" in Neth. *J. Plant Path.*, 1964, 70, 73-80).

Example 22. Selection of Variant Strain of *Paenibacillus* sp. Strain NRRL B-50972

Under standard laboratory conditions *Paenibacillus* sp. strain NRRL B-50972 produces multiple colony morphologies on solid agar medium. Several morphologically distinct colonies were identified and stored as glycerol stocks at −80° C. Liquid medium cultures were inoculated using stocks derived from the different colony phenotypes, and after several rounds of growth in liquid medium, re-inoculated onto solid agar medium. From here, one isolate was identified as having a stable colony phenotype under the tested conditions, while still capable of producing heat-resistant spores and fusaricidin chemistry. An isolate with a stable colony morphology is desirable for further strain improvement (see Example 23). This isolate was deposited with the NRRL on Sep. 1, 2015, and has been assigned the following accession number: NRRL B-67129.

Example 23. Random Mutagenesis to Generate Improved *Paenibacillus* sp. Mutants

Chemical Mutagenesis

In order to create a pool of genetically diverse isolates of *Paenibacillus* sp. strain NRRL B-67129, a liquid-grown culture of the strain was pelleted by centrifugation, and resuspended in buffer containing 1-methyl-3-nitro-1-nitroguanidine (NTG) at a final concentration of 400 μg/mL. As a reference, a second sample without NTG was prepared. The samples were incubated for 1 hour at 30° C. and 220 rpm. After 1 hour, the samples were pelleted by centrifugation, washed with buffer containing no NTG, and finally resuspended in the same volume of fresh buffer. Aliquots of the undiluted culture were frozen as glycerol stocks at −80° C. The samples were diluted and plated on agar plates to determine the colony-forming units, and a kill percentage was determined as a reference for the degree of mutations per genome. Improved isolates selected from a first round of screening were subjected to one or more subsequent rounds of NTG treatment as described above and screened for further improvements in fusaricidin production. Fusaricidin production was determined by the relative amounts of several compounds including fusaricidin A (also known as LiF04a or "Fus A"); LiF08a; Paeniserines A1 and B1 (also known as "M868" or "868"); and Paeniprolixins A2 and B2 (also known as "M938" or "938").

High Throughput Screening and Isolate Characterization

NTG-treated samples were diluted and plated on agar plates to obtain single colonies. Single colonies were inoculated into 96-well deep well blocks containing seed medium, which were incubated with shaking for 2 days at 30° C. From here, new 96-well deep well blocks containing a soy-based production medium were inoculated and incubated with shaking for 5 days at 30° C. After 5 days, glycerol stocks were prepared from each sample in an individual well and stored at −80° C., and a sample was subjected to chemical analysis of the four fusaricidin biomarkers identified above. In this primary screen, individual isolates were considered as hits if their "total Fusaricidin value" (i.e., the sum of the four analyzed fusaricidin biomarkers relative to the mean of the wild type values) was higher than the mean of the wild type values plus 3× the standard deviation of the wild type values. 8 replicates of each isolate selected based on this criterion were grown up and analyzed as described above. Confirmed fusaricidin overproducers were next scaled up into 50 mL volumes in 250 mL shake flasks, and characterized for sporulation, fusaricidin production, and bioactivity. Prioritized isolates were further scaled up into bioreactors and again characterized for sporulation, viscosity, fusaricidin production, and bioactivity. Several mutant strains were obtained from the second round of NTG-treatment and screening and found to have superior fusaricidin biomarker production and bioactivity.

Example 24. Characterization of Antibiotic Sensitivity of *Paenibacillus* sp. Strain NRRL B-50972

*Paenibacillus* sp. strain NRRL B-50972 was inoculated on solid sLB agar medium and sLB agar medium supplemented with antibiotics at typical concentrations. Agar plates were incubated at 30° C., and growth was assessed after 24, 48, and 72 hours. The sensitivity of *Paenibacillus* sp. strain NRRL B-50972 to each of the antibiotics tested is shown in Table 22.

TABLE 22

Antibiotic sensitivity of *Paenibacillus* sp. strain NRRL B-50972.

| Antibiotic (Final Concentration) | Sensitive/Resistant |
|---|---|
| Chloramphenicol (5 μg/mL) | Resistant |
| Erythromycin (5 μg/mL) | Sensitive |
| Kanamycin (10 μg/mL) | Sensitive |
| Lincomycin (25 μg/mL) | Resistant |
| Nalidixic acid (25 μg/mL) | Sensitive |
| Polymyxin B (10 μg/mL) | Resistant |
| Spectinomycin (100-250 μg/mL) | Resistant (growth, albeit reduced, after 48 and 72 incubation) |
| Tetracyclin (5 μg/mL) | Sensitive |

Example 25. Characterization of spo0A in *Paenibacillus* sp. Strain NRRL B-50972 and *Paenibacillus* sp. Strain NRRL B-67129

The genomes of *Paenibacillus* sp. strain NRRL B-50972 and *Paenibacillus* sp. strain NRRL B-67129 were sequenced. A comparison of the two genome sequences identified a characteristic difference in the spo0A gene in the two strains. As shown in the sequence alignment in FIG. 15, *Paenibacillus* sp. strain NRRL B-50972 and *Paenibacillus* sp. strain NRRL B-67129 differ in one nucleotide towards the 3'-end of the spo0A gene. A single nucleotide difference was identified and is indicated by a red arrow below the sequence in FIG. 15. Nucleotide numbers relative to the first nucleotide of the spo0A gene are indicated above the sequences.

Figure 16:
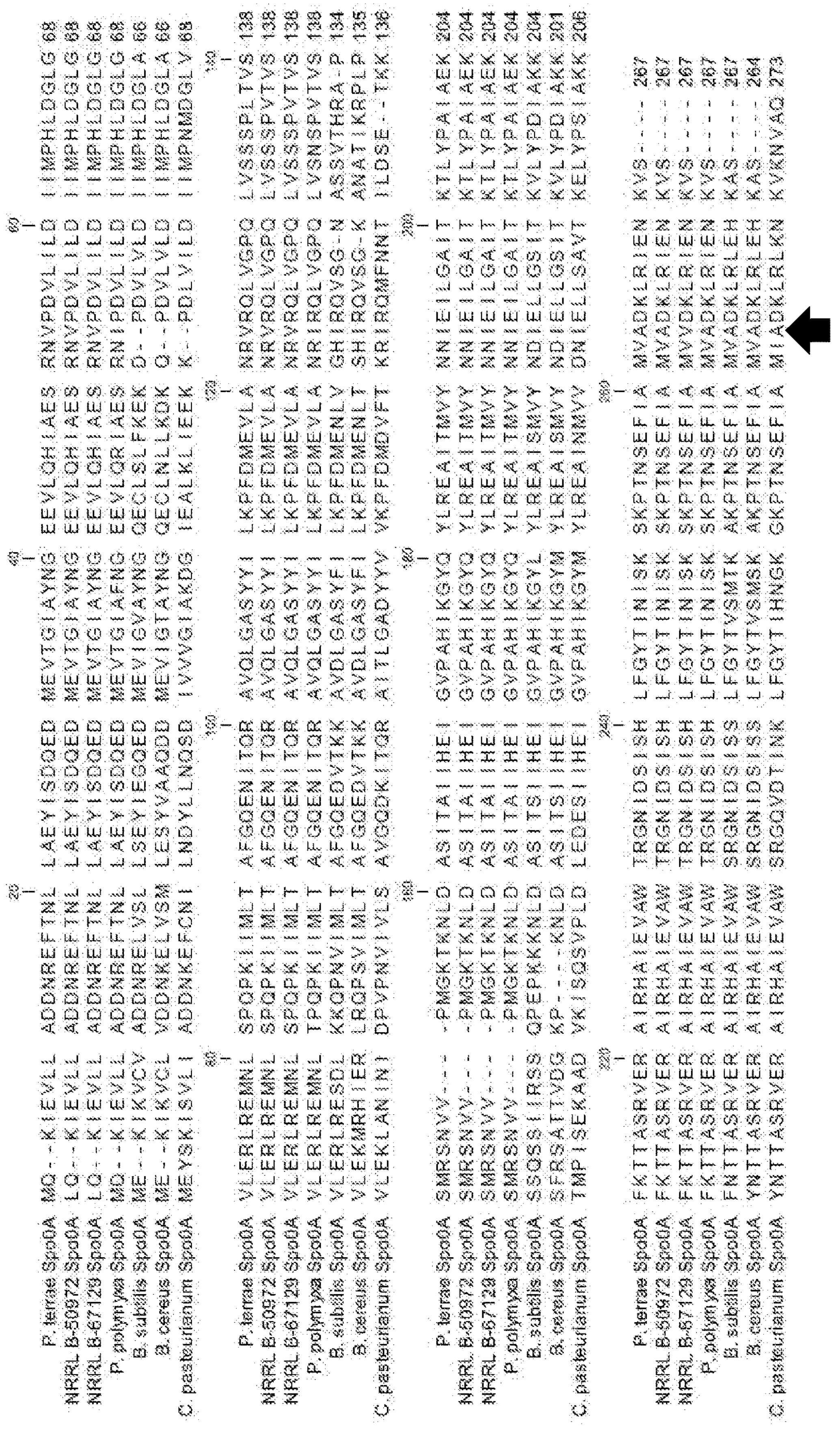
FIG. 16 depicts a sequence alignment of Spo0A orthologs from endospore-forming bacteria indicating the nucleotide change in the *Paenibacillus* sp. strain NRRL B-67129 coding sequence results in a single amino acid substitution in a conserved region. The aligned Spo0A ortholog sequences are: *Paenibacillus terrae* Spo0A (SEQ ID NO: 14), *Paenibacillus* sp. strain NRRL B-50972 Spo0A (SEQ ID NO: 15), *Paenibacillus* sp. strain NRRL B-67129 Spo0A (SEQ ID NO: 16), *Paenibacillus polymyxa* Spo0A (SEQ ID NO: 17), *Bacillus subtilis* Spo0A (SEQ ID NO: 18), *Bacillus cereus* Spo0A (SEQ ID NO: 19), and *Clostridium pasteurianum* Spo0A (SEQ ID NO: 20).

An alignment of Spo0A orthologs from endospore-forming bacteria indicated that the nucleotide change in the *Paenibacillus* sp. strain NRRL B-67129 coding sequence results in a single amino acid substitution in a conserved region (see FIG. 16). The Spo0A amino acid sequences from *Paenibacillus terrae* (NCBI Reference Sequence: WP_044647644.1), *Paenibacillus polymyxa* SQR-21 (GenBank: AHM66630.1), *Bacillus subtilis* subsp. *subtilis* str. 168 (NCBI Reference Sequence: NP_390302.1), *Bacillus cereus* E33L (GenBank: AJI26924.1), and *Clostridium pasteurianum* DSM 525 (GenBank: AAA18883.1) were aligned with the Spo0A amino acid sequences from *Paenibacillus* sp. strain NRRL B-50972 and *Paenibacillus* sp. strain NRRL B-67129. An arrow in FIG. 16 indicates a single amino acid substitution in Spo0A from *Paenibacillus* sp. strain NRRL B-67129.

Figure 17:
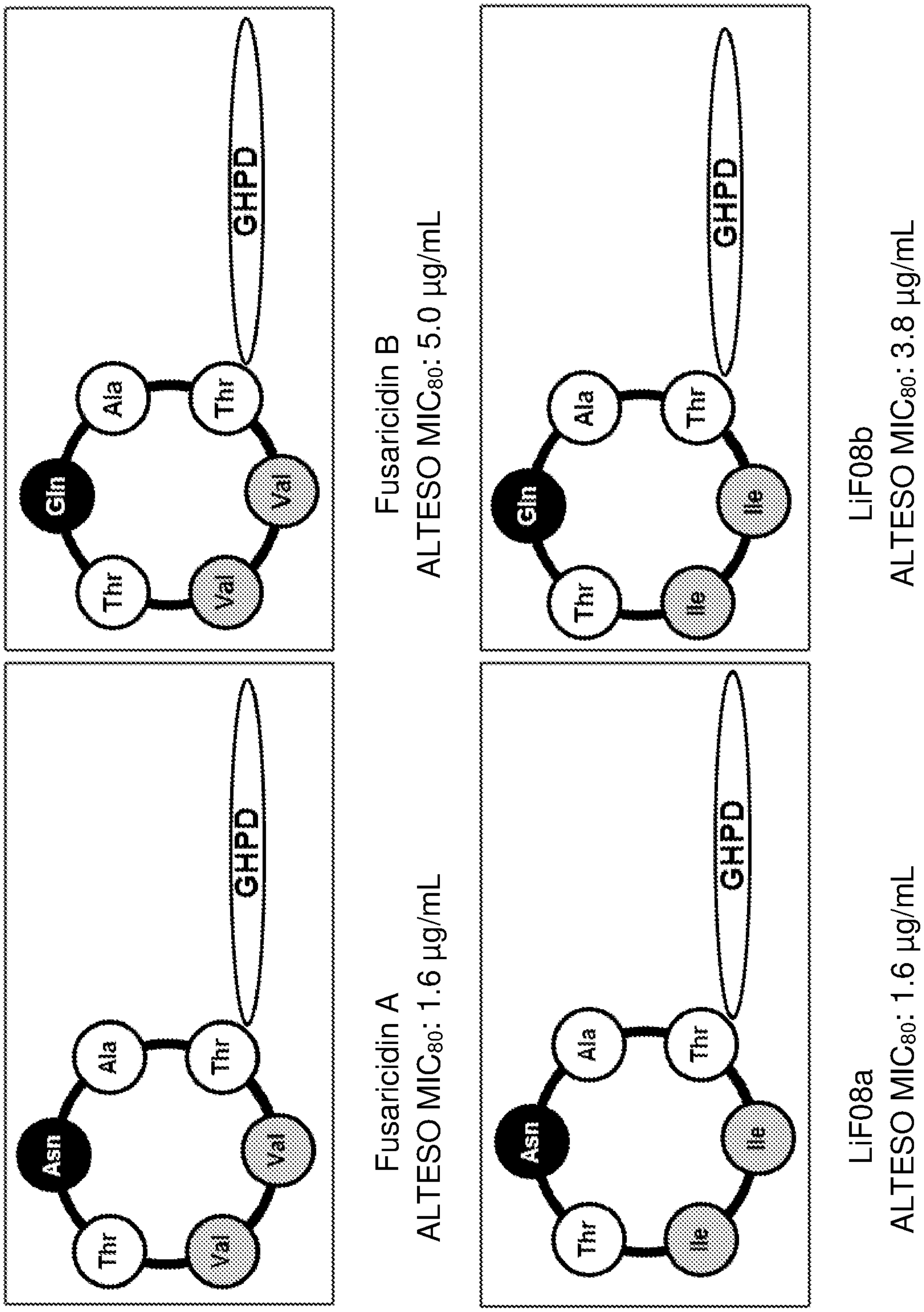
FIG. 17 depicts the Minimum Inhibitory Concentrations for 80% (MIC80) values of several fusaricidins, Paeniserines, and Paeniprolixins with the fungal pathogens *Alternaria solani* (ALTESO) and *Colletotrichum lagenarium* (COLLLA).
Figure 17:
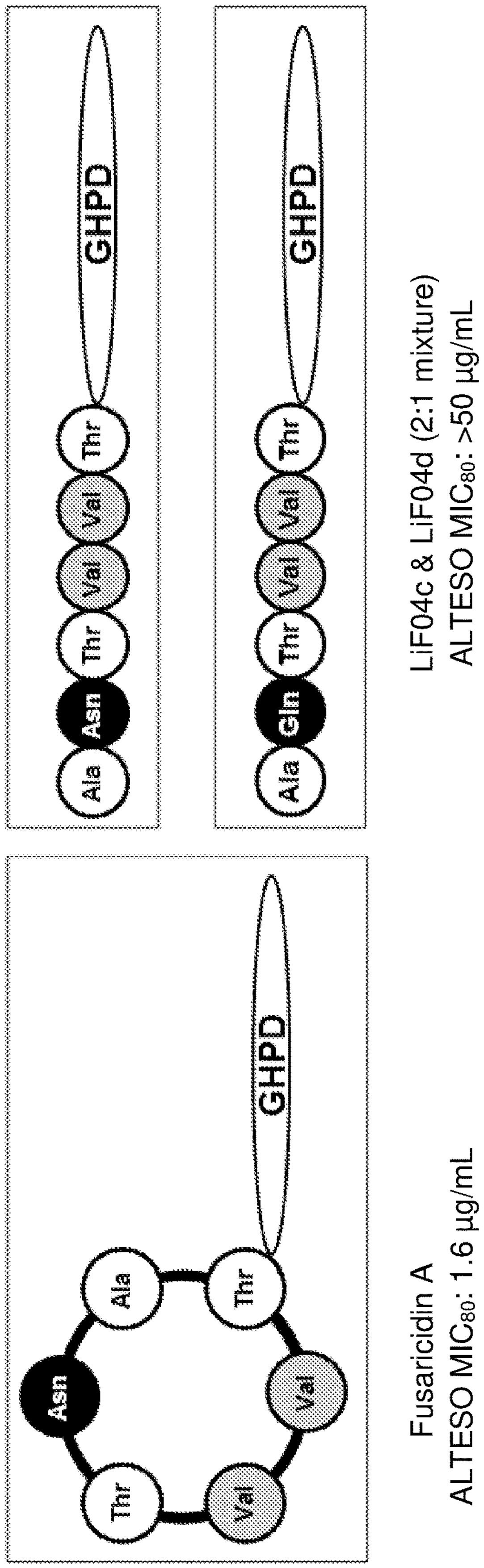
Figure 17:
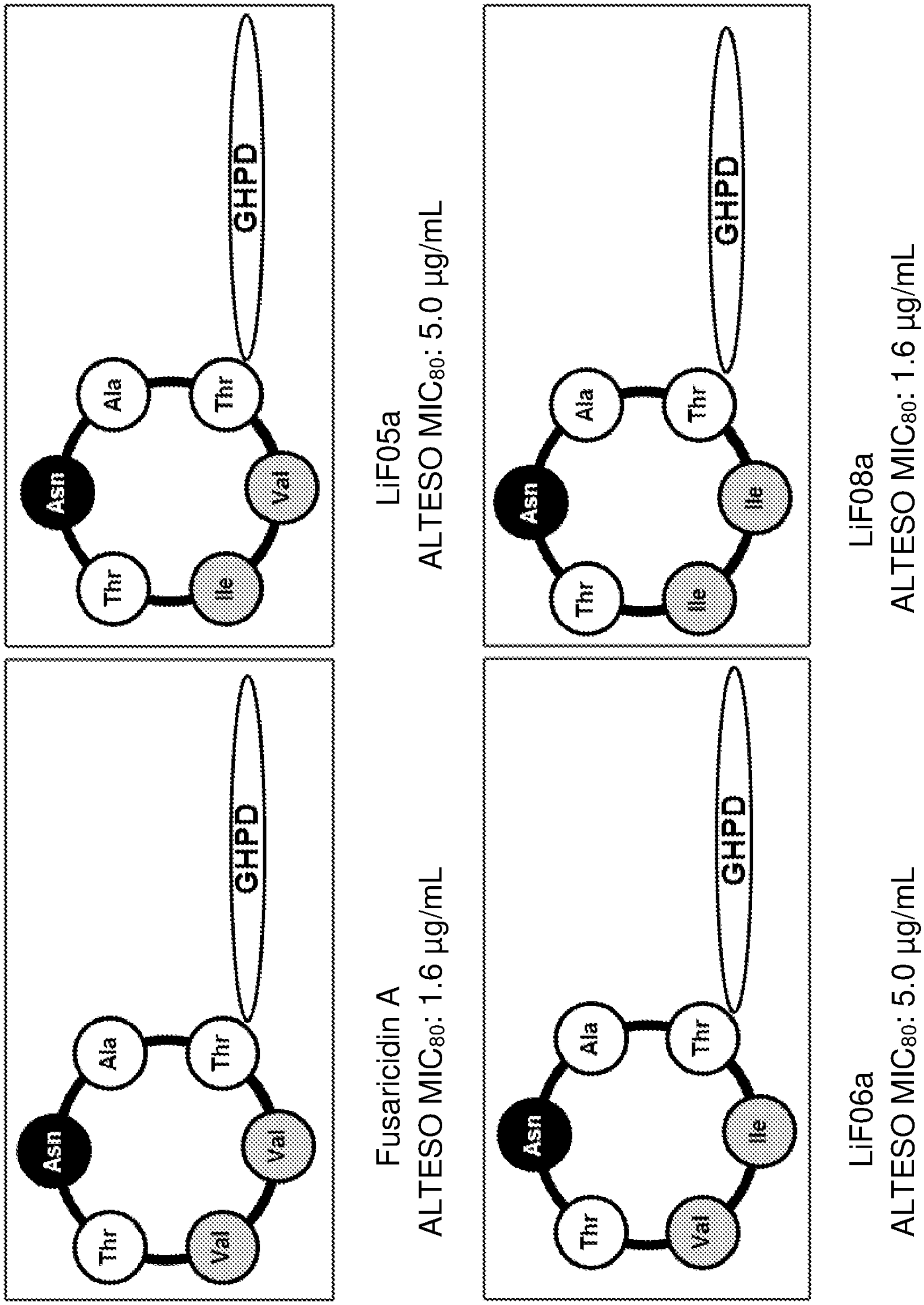
Figure 17:
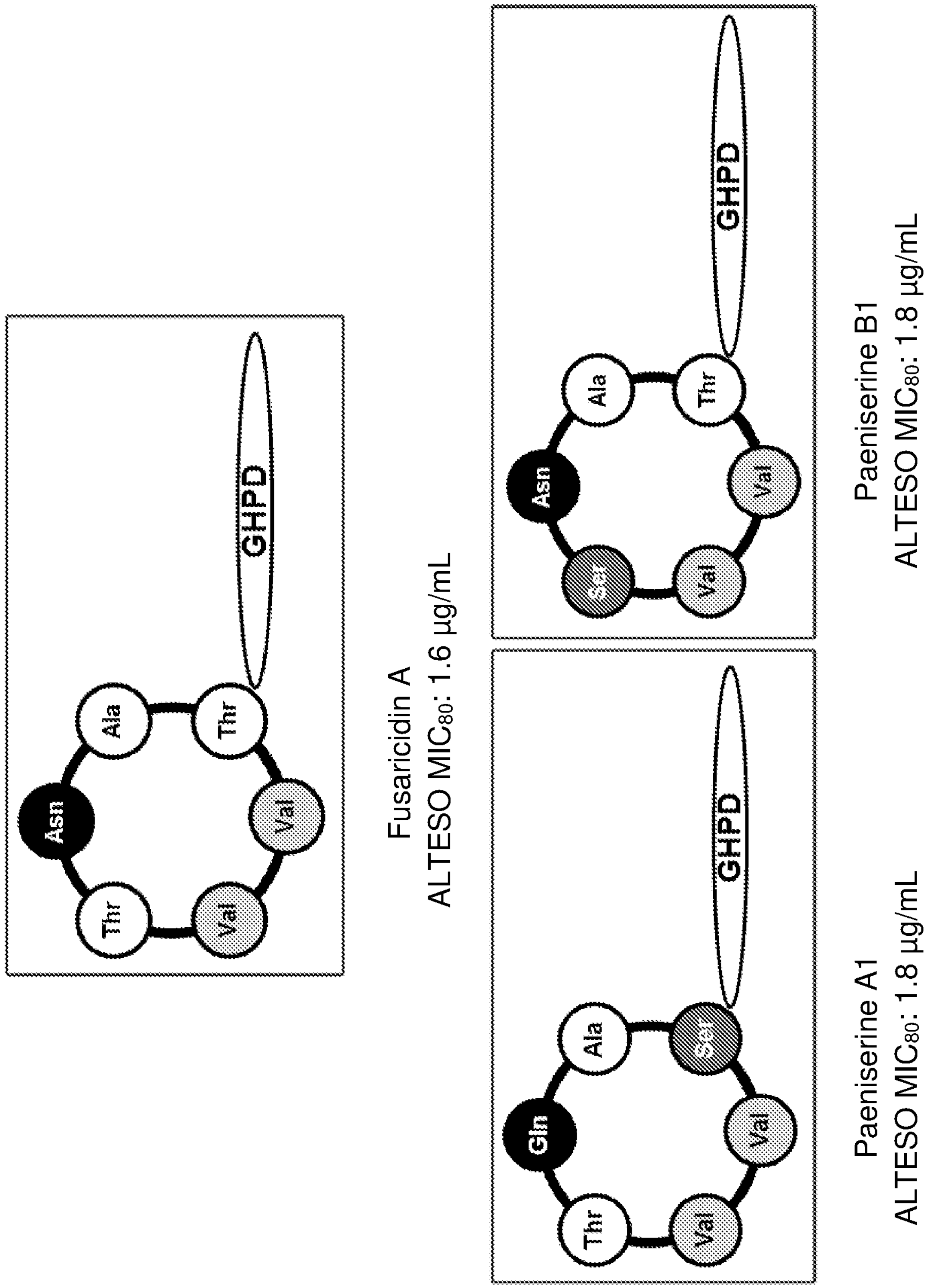

Example 26. Structure Activity Relationship Studies with Fusaricidins, Paeniserines, and Paeniprolixins The structure activity relationship of several purified fusaricidins, Paeniserines, and Paeniprolixins was investigated using the in vitro assay described in Example 16. In a first experiment, the most common pairs of fusaricidins were compared. A variation in these fusaricidins occurs at amino acid position (5) of the ring/chain with either asparagine or glutamine. In this study Fusaricidin A was compared to Fusaricidin B, and LiF08a was compared to LiF08b against the plant pathogen *Alternaria solani* (ALTESO). In both cases the asparagine analogue was over twice more potent than its glutamine counterpart (see FIG. 17).

In another experiment, cyclic versus acyclic forms of fusaricidins were compared. It is unclear if the acyclic forms of fusaricidins are a precursor or degradation product of the final compound; however they are ubiquitous in the fermentation broth of *Paenibacillus* sp. strain NRRL B-50972 and a common contaminant of purified fusaricidins from this fermentation broth. The antifungal activity of fusaricidin A was compared to a mixture of LiF04c and LiF04d (acyclic analogues of Fusaricidin A and B) in the in vitro assay with the plant pathogen ALTESO. There is a significant impact of the peptide ring opening at the ester bond. Acyclic analogues were inactive at the highest concentrations tested (see FIG. 17). This is important in regards to structural information and to demonstrate that these compounds that typically make up the impurities in otherwise purified fusaricidins likely do not contribute to antifungal activity.

The amino acid substitutions in the amino acid positions (2) and (3) of the ring/chain were also investigated. The analogues Fusaricidin A, LiF05a, LiF06a, and LiF08a differ in those positions with either valine or isoleucine combinations. They were tested in the in vitro assay with the plant pathogen ALTESO. The two most potent analogues were Fusaricidin A (valine/valine) and LiF08a (isoleucine/isoleucine). The other two analogues, comprising of a mixture of valine/isoleucine, were over three times less potent (see FIG. 17).

The differences in antifungal activity with the novel Paeniserines were also investigated. Again testing against ALTESO, the differences in the amino acid positions (1) and (4) of the ring/chain were evaluated. Classical fusaricidins are restricted to threonine in those positions while Paeniserines can alternate between threonine and serine. The Paeniserines demonstrated similar antifungal activity to fusaricidin A in this assay (see FIG. 17).

The antifungal activity of the Paeniprolixins (i.e., analogues with different side chain lengths) was also investigated with in vitro assays against the fungal pathogens ALTESO and *Colletotrichum lagenarium* (COLLLA). The classical fusaricidin comprises a 15-guanidino-3-hydroxypentadecanoic acid side chain. The Paeniprolixins have been shown to have 2 of 4 additional methylene groups in the chain. Side chain length demonstrated a pronounced effect on the bioactivity and exhibited differences with distinct fungal pathogens. Against ALTESO the unaltered length of GHPD was the most potent, decreasing with each additional methylene group. Against COLLLA, the most potent length was GHPD+2$CH_2$ (see FIG. 17).

Example 27. Synergistic Antifungal Activity with Mixtures of Fusaricidin A with Paeniserine A1 or Paeniprolixin C1

The in vitro antifungal 96-well plate assay with the resazurin-based cell viability reagent PRESTOBLUE® (see Example 18) was used to evaluate the antifungal activity of fusaricidins, Paeniserines, and Paeniprolixins alone and in two-way combinations. Antifungal activity was calculated in relation to untreated control values with the following equation:

Efficacy=(100−Relative Growth of Untreated Control)

A 100% efficacy indicated no fungal growth compared to the untreated control, and a 0% efficacy indicated no inhibition of fungal growth compared to the untreated control.

Tables 23 and 24 clearly shows that the observed activity of the active compound combinations according to the invention was greater than the calculated activity, i.e. a synergistic effect was present.

TABLE 23

Antifungal Activity against *Alternaria solani* of Fusaricidin A alone, Paeniserine A1 alone, and Fusaricidin A + Paeniserine A1

| Active Compounds | Application Rate of Active Compound in mg/mL | Efficacy in % found* | Efficacy in % calc.** |
|---|---|---|---|
| Fusaricidin A | 0.25 | 39.0 | |
| Paeniserine A1 | 0.0083 | 0.5 | |
| Fusaricidin A + Paeniserine A1 | 0.25 + 0.0083 | 48.2 | 39.3 |

*found = activity found
**calc. = activity calculated using Colby's formula

TABLE 24

Antifungal Activity against *Alternaria solani* of Fusaricidin A alone, Paeniprolixin alone, and Fusaricidin A + Paeniprolixin C1

| Active Compounds | Application Rate of Active Compound in mg/mL | Efficacy in % found* | Efficacy in % calc.** |
|---|---|---|---|
| Fusaricidin A | 0.25 | 42.0 | |
| Paeniprolixin C1 | 0.0083 | 25.4 | |
| Fusaricidin A + Paeniprolixin C1 | 0.25 + 0.025 | 68.1 | 56.7 |

*found = activity found
**calc. = activity calculated using Colby's formula

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method of identifying a fungicidal *Paenibacillus* sp. strain with broad spectrum antifungal activity, the method comprising:

a) sequencing FusA-A3 in the *Paenibacillus* sp. strain to characterize a variant fusaricidin synthetase;

b) assaying the fungicidal activity of the *Paenibacillus* sp. strain with the variant fusaricidin synthetase;

c) selecting the fungicidal *Paenibacillus* sp. strain as having broad spectrum antifungal activity if the *Paenibacillus* sp. strain comprises the variant fusaricidin synthetase and demonstrates increased fungicidal activity compared to a reference *Paenibacillus* sp. strain comprising a wild-type fusaricidin synthetase, and d) culturing the fungicidal *Paenibacillus* sp. strain to produce a fungicidal fermentation product, wherein the variant fusaricidin synthetase comprises a deletion in FusA-A3 of amino acid residues that correspond to positions Asp254, Ala255, Ser258, Thr297, Leu318, Ala320, Gly341, Ile349 and Cys350 of SEQ ID NO: 11 or Asp254, Ala255, Ser258, Thr297, Leu318, Ala320, Ala341, Val349, and Cys350 of SEQ ID NO: 9 or Asp254, Ala255, Ser258, Thr297, Leu318, Ala320, Gly341, Val349 and Cys350 of SEQ ID NO: 1.

2. The method of claim 1, further comprising quantifying a Paeniserine and/or Paeniprolixin produced by the *Paenibacillus* sp. strain and selecting the *Paenibacillus* sp. strain as having broad spectrum antifungal activity if the *Paenibacillus* sp. strain produces increased levels of the Paeniserine and/or Paeniprolixin compared to the reference *Paenibacillus* sp. strain comprising a wild-type fusaricidin synthetase.

* * * * *